(12) United States Patent
Hwang et al.

(10) Patent No.: US 9,593,144 B2
(45) Date of Patent: Mar. 14, 2017

(54) FPR1 ANTAGONIST DERIVATIVES AND USE THEREOF

(71) Applicant: CHANG GUNG UNIVERSITY, Tao-Yuan (TW)

(72) Inventors: Tsong-Long Hwang, Tao-Yuan (TW); Pei-Wen Hsieh, Tao-Yuan (TW); Yin-Ting Huang, Tao-Yuan (TW); Chih-Hao Hung, Tao-Yuan (TW)

(73) Assignee: CHANG GUNG UNIVERSITY, Kwei-Shan, Tao-Yuan (TW)

( * ) Notice: Subject to any disclaimer, the term of this patent is extended or adjusted under 35 U.S.C. 154(b) by 0 days.

(21) Appl. No.: 14/792,147

(22) Filed: Jul. 6, 2015

(65) Prior Publication Data
US 2015/0307548 A1   Oct. 29, 2015

Related U.S. Application Data

(62) Division of application No. 14/248,649, filed on Apr. 9, 2014.

(51) Int. Cl.
| C07K 5/065 | (2006.01) |
| C07D 209/20 | (2006.01) |
| C07K 5/078 | (2006.01) |
| A61K 38/00 | (2006.01) |

(52) U.S. Cl.
CPC ........ C07K 5/06078 (2013.01); C07D 209/20 (2013.01); C07K 5/06156 (2013.01); A61K 38/00 (2013.01)

(58) Field of Classification Search
CPC .................... C07K 5/06156; C07K 5/06078
See application file for complete search history.

(56) References Cited

U.S. PATENT DOCUMENTS

| 8,440,684 B2 | 5/2013 | Beard et al. |
| 2011/0319454 A1 | 12/2011 | Beard et al. |
| 2012/0238628 A1 | 9/2012 | Vuligonda et al. |
| 2013/0109866 A1 | 5/2013 | Beard et al. |

FOREIGN PATENT DOCUMENTS

| EP | 2490021 A1 | 8/2012 |
| WO | 2012074785 A1 | 6/2012 |
| WO | 2012109544 A1 | 8/2012 |
| WO | 2012112048 A1 | 8/2012 |
| WO | 2013009543 A1 | 1/2013 |
| WO | 2013062947 A1 | 5/2013 |
| WO | 2013070600 A1 | 5/2013 |

OTHER PUBLICATIONS

Hwang et al. ("Design and synthesis of tryptophan containing dipeptide derivatives as formyl peptide receptor 1 antagonist," Org. Biomol. Chem., 2013, 11, 3742-3755 published online Apr. 11, 2013).*

Charlotta Movitz, et al., "The Annexin I Sequence Gln-Ala-Trp-Phe Is a Core Structure for Interaction with the Formyl Peptide Receptor 1", J. Biol. Chem, 2010, 14338-45.

* cited by examiner

Primary Examiner — Christina Bradley
(74) Attorney, Agent, or Firm — Muncy, Geissler, Olds & Lowe, P.C.

(57) ABSTRACT

A dipeptide derivative as formyl peptide receptor 1 (FPR1) antagonist is provided. The dipeptide derivative is represented by formula (I),

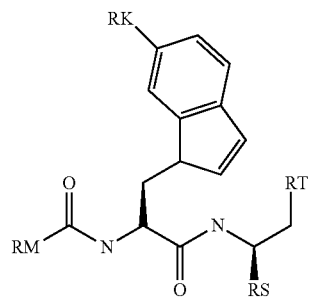

formula (I)

wherein:
the chiral centers in formula (I) are S and R configurations respectively;
each of RK and RT is selected from a group consisting of a hydrogen, a hydroxyl group, a $C_1$-$C_4$ alkyl-substituted hydroxyl group, a $C_1$-$C_4$ alkoxyl group, a carboxylic acid group, a $C_1$-$C_4$ alkyl nitrile-substituted, $C_1$-$C_4$ alkyl-substituted or $C_1$-$C_4$ alkoxyl-substituted amido group, a $C_1$-$C_4$ alkyl-substituted ester group and a benzoyl group having a $C_1$-$C_4$ alkyl-substituted benzene ring; and each of RM and RS is selected from a group consisting of a hydrogen, a hydroxyl group, a phenyl group, a pyridinyl group, a carboxylic acid group, a $C_1$-$C_4$ alkoxyl substituted ester group, and a benzoyl group having a hydroxyl-substituted, a halogen-substituted, a $C_1$-$C_4$ alkoxyl-substituted or a $C_1$-$C_4$ alkyl-substituted benzene ring.

6 Claims, 20 Drawing Sheets

FPR1 ANTAGONIST DERIVATIVES AND USE THEREOF

PRIORITY

This application claims the benefit of Taiwan Patent Application No. 102136641, filed on Oct. 9, 2013, at the Taiwan Intellectual Property Office, the disclosures of which are incorporated herein in their entirety by reference.

FIELD OF THE INVENTION

The present invention relates to the use of dipeptide derivatives, such as N—(N-aroyl-L-tryptophanyl)-D-phenylalanine methyl esters and their applications in diseases or symptoms associated with formyl peptide receptor 1 (FPR1) activities.

BACKGROUND OF THE INVENTION

Formyl peptide receptor (FPR) belongs to the family of G-protein coupled receptors (GPCRs). The FPR family can be divided into three classes, FPR1, FPR2 and FPR3. FPR2 and FPR3 are classified into FPR-like receptors, wherein FPR2 is also known as FPR-like receptor 1 (FPRL-1) and FPR3 is also known as FPR-like receptor 2 (FPRL-2). FPR1 is found in monocytes, polymorphonuclear leukocytes and immature dendritic cells, and FPR2 is found in liver cells, lung cells, spleen cells, T lymphocytes, monocytes and polymorphonuclear leukocytes. FRP1 and FPR2 are two members of the FPRs, which are found in human neutrophils. Formyl-L-methionyl-L-leucyl-L-phenylalanine (fMLP or fMLF) is a N-formyl peptide, which is a chemoattractant bound to FPR1 and further to trigger a cell activating response to release toxic substances or proteases. The affinities of fMLF toward the three FPR receptors are different, and the affinity is higher for FPR1. The activation of FPR1 elicits multiple signaling pathways, such as calcium, phospholipase C, phosphatidylinositol 3-kinase (PI3K), mitogen-activated protein kinases (MAPKs), and protein tyrosine kinases (PTKs), which cause neutrophils activation for migration, respiratory burst, and degranulation. Thus some literature reported that inhibition of activation of neutrophils could be as target for treatment of inflammation induced by neutrophils, such as asthma, rheumatoid arthritis, psoriasis, sepsis, myocardial ischemia/reperfusion injury, acute respiratory distress syndrome, chronic obstructive pulmonary disease, etc. Recent studies indicated that FPR1 is not only involved in infection and the inflammatory process, but also playing a role in promoting tumor progression. In particular, FPR1 is able to interact with endogenous annexin AI, and then transactivate EGFR in glioblastoma cells to mediate cell migration and growth. Therefore, FPR1 also is a therapeutic target for treating human glioblastoma.

In 2010, Movitz and his co-workers showed that a peptide with a Trp-Phe fragment in the C-terminal was able to selectively bind to the FPR1 receptor; however, this dipeptide alone was unable to inhibit the neutrophil respiratory burst induced by FMLP, and the associated generation of superoxide anion ($O_2^-$) or radicals.

Additionally, a search Orbit and Google patent databases, EP 2490021 A1 and WO 2012112048 A1 recited a series of dipeptide derivatives containing chemical formulas such as H—$X_1$—$X_2$—OH, which can be used as pattern recognition receptors and the signal transduction pathway for G-protein coupled receptors, wherein configurations of two amino acids are both S (or R) configurations.

US 20130109866 A1 and WO 2013062947 A1 disclose that a series of derivatives of N-terminal amino acids containing urea groups can regulate a FPRL-1 receptor, which is an alias for an FPR2 receptor.

WO 2012074785 A1, WO 2013070600 A1, U.S. Pat. No. 8,440,684 B2, WO 2013009543 A1, US 20120238628 A1, US 20110319454 A1 and WO 2012109544 A1 all disclose technical solutions for regulating compounds about FPRL-1 receptors.

Based on the above, FPR1 antagonists can regulate inflammation, cancers and other diseases, but no FPR1 antagonist is used clinically. Therefore, the development of an FPR1 antagonist is currently very important.

SUMMARY OF THE INVENTION

In accordance with an aspect of the present invention, a method for treating neutrophil inflammatory disorders with an antagonist of formyl peptide receptor 1 (FPR1) is provided. The method includes providing a derivative of N—(N-aroyl-L-tryptophanyl)-D-phenylalanine represented by formula (I), wherein: the chiral centers in formula (I) are S and R configurations respectively; each of RK and RT is selected from a group consisting of a hydrogen, a hydroxyl group, a $C_1$-$C_4$ alkyl-hydroxyl substituted ($C_1$-$C_4$ alkyl-OH) group, a $C_1$-$C_4$ alkoxyl group, a carboxylic acid group, a $C_1$-$C_4$ alkyl nitrile-substituted (CONH$C_1$-$C_4$alkyl-CN) group, or $C_1$-$C_4$ alkyl-substituted (CONH$C_1$-$C_4$ alkyl) or $C_1$-$C_4$ alkoxyl-substituted (CONH$C_1$-$C_4$ alkoxyl) amido group, a $C_1$-$C_4$ alkyl-substituted ester (COO$C_1$-$C_4$ alkyl) group and a benzoyl group having a $C_1$-$C_4$ alkyl-substituted benzene ring; and each of RM and RS is selected from a group consisting of a hydrogen, a hydroxyl group, a phenyl group, a pyridinyl group, a carboxylic acid group, a $C_1$-$C_4$ alkoxyl substituted ester group, and a benzoyl group having a hydroxyl-substituted, a halogen-substituted, a $C_1$-$C_4$ alkoxyl-substituted or a $C_1$-$C_4$ alkyl-substituted benzene ring.

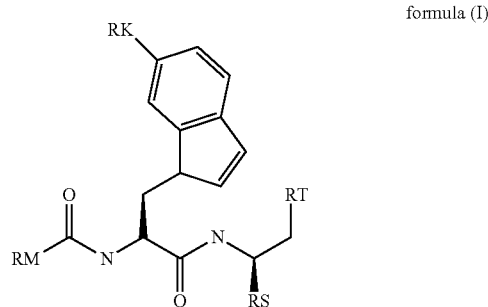

formula (I)

In accordance with another aspect of the present invention, a dipeptide derivative is provided. The dipeptide derivative is represented by formula (I),

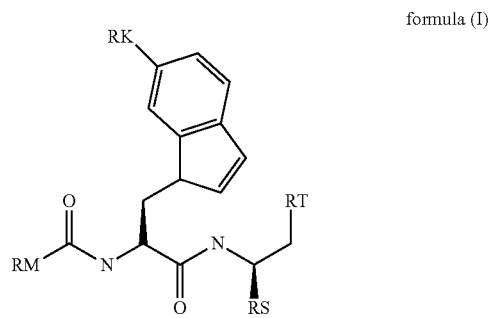

formula (I)

wherein:
the chiral centers in formula (I) are S and R configurations respectively; each of RK and RT is selected from a group consisting of a hydrogen, a hydroxyl group, a $C_1$-$C_4$ alkyl-substituted hydroxyl group, a $C_1$-$C_4$ alkoxyl group, a carboxylic acid group, a $C_1$-$C_4$ alkyl nitrile-substituted, $C_1$-$C_4$ alkyl-substituted or $C_1$-$C_4$ alkoxyl-substituted amido group, a $C_1$-$C_4$ alkyl-substituted ester group and a benzoyl group having a $C_1$-$C_4$ alkyl-substituted benzene ring; and each of RM and RS is selected from a group consisting of a hydrogen, a hydroxyl group, a phenyl group, a pyridinyl group, a carboxylic acid group, a $C_1$-$C_4$ alkoxyl substituted ester group, and a benzoyl group having a hydroxyl-substituted, a halogen-substituted, a $C_1$-$C_4$ alkoxyl-substituted or a $C_1$-$C_4$ alkyl-substituted benzene ring.

In accordance with a further aspect of the present invention, a dipeptide derivative is provided. The dipeptide derivative is represented by formula (I),

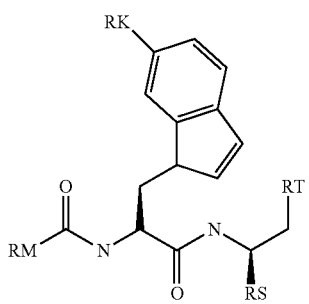

formula (I)

wherein:
the chiral centers in formula (I) are S and R configurations respectively;
RK is selected from a hydrogen; RS is selected from a methylphenyl group;
RM is selected from a phenyl group; and
RT is selected from $C_1$-$C_4$ alkoxyl-substituted ester group.

In accordance with further another aspect of the present invention, a dipeptide derivative is provided. The dipeptide derivative is represented by formula (I),

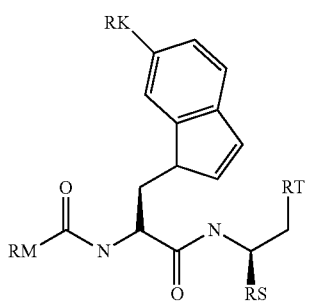

formula (I)

wherein:
the chiral centers in formula (I) are S and R configurations respectively;
RK is selected from a hydrogen;
RS is selected from a methyl-$C_6$-cycloalkyl group;
RM is selected from a phenyl group; and
RT is selected from $C_1$-$C_4$ alkyl-substituted ester group.

In accordance with further another aspect of the present invention, a method for treating a neutrophil inflammatory disorders with an antagonist of Formyl Peptide Receptor 1 (FPR1) is provided. The method includes providing a derivative of N—(N-aroyl-L-tryptophanyl)-D-phenylalanine methyl esters represented by formula (II), wherein:

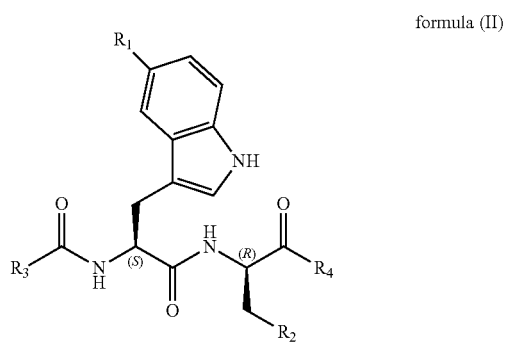

formula (II)

the chiral centers in formula (II) are S and R configurations respectively;
$R_1$ is one selected from a group consisting of a hydrogen, a hydroxyl group and a methoxy group;
$R_2$ is one selected from a group consisting of a non-substituted phenyl group, a mono-substituted phenyl group, a di-substituted phenyl group, or a tri-substituted phenyl group, a pyridinyl group and a $C_4$-$C_6$ cycloalkyl group;
$R_3$ is one selected from a group consisting of a non-substituted benzyl group, a mono-substituted benzyl group, a di-substituted benzyl group and a tri-substituted benzyl group; and
$R_4$ is one selected from a group consisting of a hydroxyl, a C1-C4 alkoxyl and a glycin-nitrile groups.

In accordance with further another aspect of the present invention, a method for treating a neutrophil inflammatory disorder with an antagonist of formyl peptide receptor 1 (FPR1) is provided. The method includes providing a derivative of N—(N-aroyl-L-tryptophanyl)-D-phenylalanine methyl esters represented by formula (II), wherein:

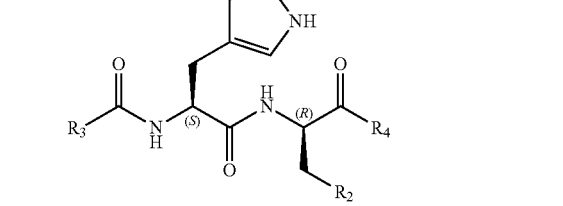

formula (II)

wherein the chiral centers in formula (II) are S and R configurations respectively;
$R_1$ is one selected from a group consisting of a hydrogen, a hydroxyl group and a methoxy group;
$R_2$ is one selected from a group consisting of a non-substituted phenyl group, a mono-substituted phenyl group, a di-substituted phenyl group, or a tri-substituted phenyl, a pyridinyl and a $C_4$-$C_6$ cycloalkyl groups;

$R_3$ is one selected from a group consisting of a non-substituted benzyl group, a mono-substituted benzyl group, a di-substituted benzoyl group and a tri-substituted benzyl group; and $R_4$ is one selected from a group consisting of a hydroxyl group, a C1-C4 alkoxyl group and a glycin-nitrile group.

In accordance with further another aspect of the present invention, a dipeptide derivative is provided. The dipeptide derivative is represented by formula (II),

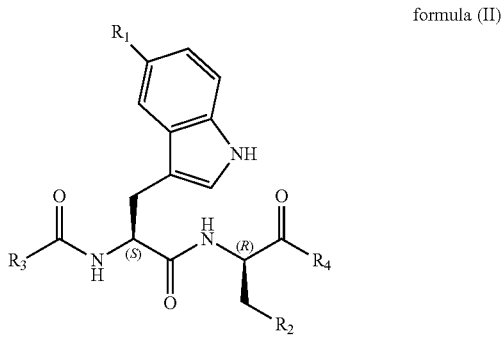

formula (II)

wherein:

the chiral centers in formula (II) are S and R configurations respectively;

$R_1$ is selected from one of a hydrogen and a hydroxyl group;

$R_2$ is one selected from a group consisting of non-substituted phenyl group, mono-substituted phenyl group, di-substituted phenyl group, or tri-substituted phenyl group and pyridinyl group;

$R_3$ is one selected from a group consisting of a non-substituted benzyl group, a mono-substituted benzyl group, a di-substituted benzyl group and a tri-substituted benzyl group; and $R_4$ is selected from one of C1-C4 alkoxyl group and a glycin-nitrile group.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

Figure 1A:
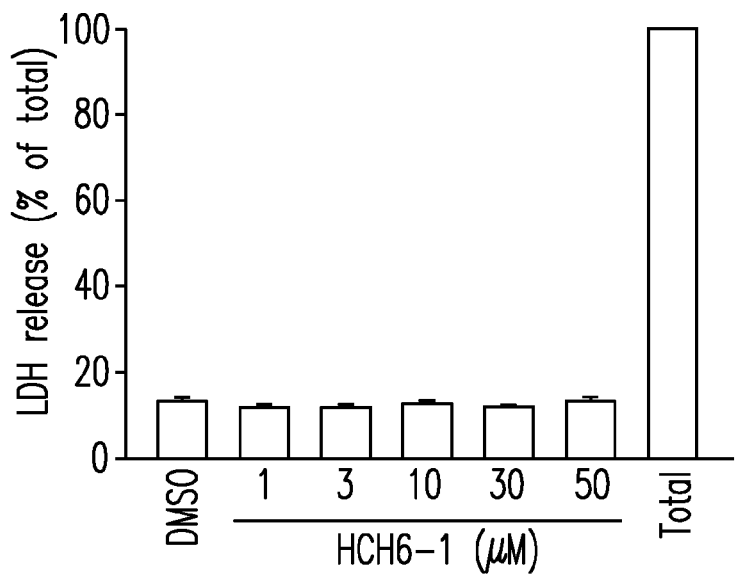
FIGS. 1(a)-1(b) show the influences of HCH6-1 on releasing lactate dehydrogenase from human neutrophils.

The present invention will now be described more specifically with reference to the following embodiments. It is to be noted that the following embodiments of this invention are presented herein for the purposes of illustration and description only; they are not intended to be exhaustive or to be limited to the precise form disclosed.

The excipient in the present invention also refers to a pharmaceutically acceptable carrier or excipient, or a bio-available carrier or excipient, including a solvent, dispersant, coat, antibacterial or antifungal agent, preservative or slow absorber, which is a proper compound used to prepare a formulation in the prior art. Usually such a carrier or excipient does not have any activity for treatments itself. And the compound disclosed in the present invention cooperating with a pharmaceutically acceptable carrier or excipient is prepared as various formulations, and will not result in adverse drug reactions, allergies or other inappropriate responses after being administered to animals or humans. Thus the compound in the present invention, cooperating with a pharmaceutically acceptable carrier or excipient, is for use in clinics and human. "Effective dose" means a dose which is enough to improve or prevent medical symptoms or biological manifestation. Effective dose maybe also stated as casting dose for use in diagnosis. Unless there is other description in the specification, "active compound" and "pharmaceutically active compound" are substitutes for each other and refer to a pharmaceutical, pharmacological or therapeutic substance as well as other effective material.

A dipeptide derivative containing a formula (I) is disclosed in the present invention. The chiral centers in formula (I) are S and R configurations respectively. RK and RT are respectively selected from one of the combination of hydrogen atom, hydroxyl group, $C_1$-$C_4$ alkyl group substitute on hydroxyl group, $C_1$-$C_4$ alkoxyl group, carboxylic acid group, $C_1$-$C_4$ alkyl nitrile substitute, $C_1$-$C_4$ alkyl substitute or $C_1$-$C_4$ alkoxyl substitute on amide group, $C_1$-$C_4$ alkyl substitute on the ester group or $C_1$-$C_4$ alkyl group substitute on the aromatic ring of benzoyl group. RM and RS are respectively selected from hydrogen atom, hydroxyl group, phenyl group, pyridinyl, carboxylic acid group, or $C_1$-$C_4$ alkoxyl substitute on the ester group, or a hydroxyl group, halogen group, $C_1$-$C_4$ alkoxyl group, $C_1$-$C_4$ alkyl group substitute on the aromatic ring of benzoyl group.

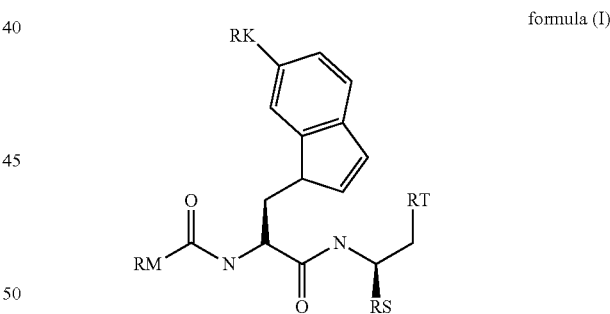

formula (I)

The dipeptide derivatives are synthesized via one of the following Schemes 1-4. Compounds 2-13, 16-24, 25-27 and 14-15 are synthesized by Schemes 1-4 respectively. Each compound may be further classified into major or minor products and noted as 'a' or 'b' respectively. $R_1$-$R_4$ are represented as substitutions. A pharmaceutically acceptable salt, solvate or combination thereof may be adopted for the dipeptide derivatives.

Scheme 1 is for the preparation of N—(N-aroyl-L-tryptophanyl)-D-phenylalanine methyl esters and their analogs, with which compounds 2-13 are synthesized.

Reagents and conditions: (a) 2.0 N NaOH, aroyl chlorides, 20 h; (b) D-phenylalanine methyl ester, HBTU, DIEA, DCM, 6 h; (c) 2.0 N NaOH, benzoyl chloride, 20 h; and (d) D-phenylalaninol, HBTU, DIEA, DCM, 6 h.

Scheme 1

Scheme 1-A

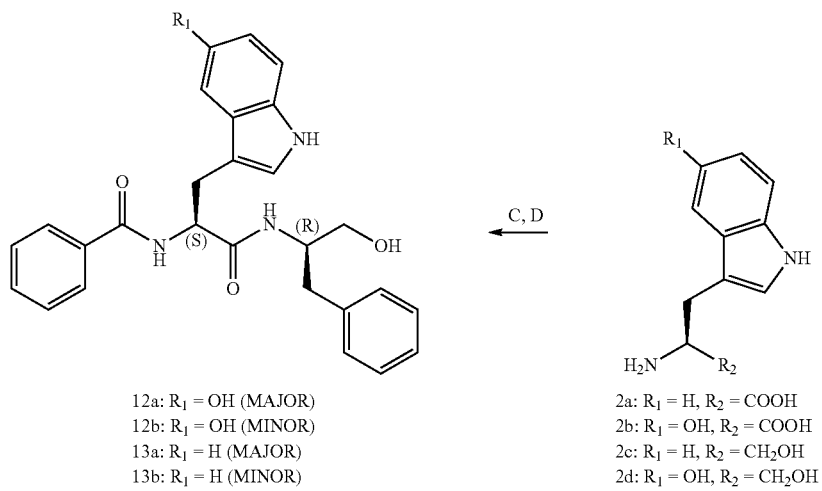

12a: R₁ = OH (MAJOR)
12b: R₁ = OH (MINOR)
13a: R₁ = H (MAJOR)
13b: R₁ = H (MINOR)

2a: R₁ = H, R₂ = COOH
2b: R₁ = OH, R₂ = COOH
2c: R₁ = H, R₂ = CH₂OH
2d: R₁ = OH, R₂ = CH₂OH

Scheme 1-B

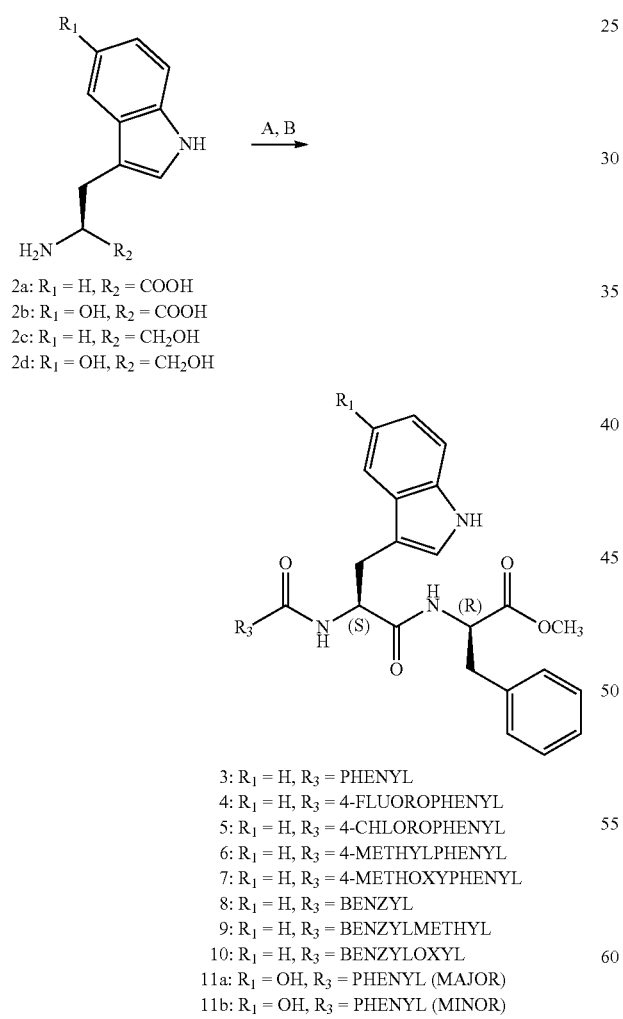

2a: R₁ = H, R₂ = COOH
2b: R₁ = OH, R₂ = COOH
2c: R₁ = H, R₂ = CH₂OH
2d: R₁ = OH, R₂ = CH₂OH

3: R₁ = H, R₃ = PHENYL
4: R₁ = H, R₃ = 4-FLUOROPHENYL
5: R₁ = H, R₃ = 4-CHLOROPHENYL
6: R₁ = H, R₃ = 4-METHYLPHENYL
7: R₁ = H, R₃ = 4-METHOXYPHENYL
8: R₁ = H, R₃ = BENZYL
9: R₁ = H, R₃ = BENZYLMETHYL
10: R₁ = H, R₃ = BENZYLOXYL
11a: R₁ = OH, R₃ = PHENYL (MAJOR)
11b: R₁ = OH, R₃ = PHENYL (MINOR)

Reagents and conditions: (a) nicotinoyl chloride, pyridine, 20 h; (b) 1.0 M LiOH, THF, 1 h; and (c) D-phenylalanine methyl ester, HBTU, DIEA, DCM, 6 h.

Scheme 2

Scheme 2-A

16a: R₃ = 4-nitrobenzyl
16b: R₃ = 4-methylbenzyl
16c: R₃ = 4-fluorobenzyl
16d: R₃ = 4-chlorobenzyl
16e: R₃ = 4-bromobenzyl
16f: R₃ = 4-trifluoromethylbenzyl
16g: R₃ = cyclohexylmethyl 17a: R₃ = 4-nitrobenzyl
17b: R₃ = 4-methylbenzyl
17c: R₃ = 4-fluorobenzyl
17d: R₃ = 4-chlorobenzyl
17e: R₃ = 4-bromobenzyl
17f: R₃ = 4-trifluoromethylbenzyl
17g: R₃ = cyclohexylmethyl Scheme 2 is for the preparation of N—(N-nictotinoyl-L-tryptophanyl)-D-phenylalanine methyl esters, with which compounds 16-24 are synthesized.

Scheme 2-B

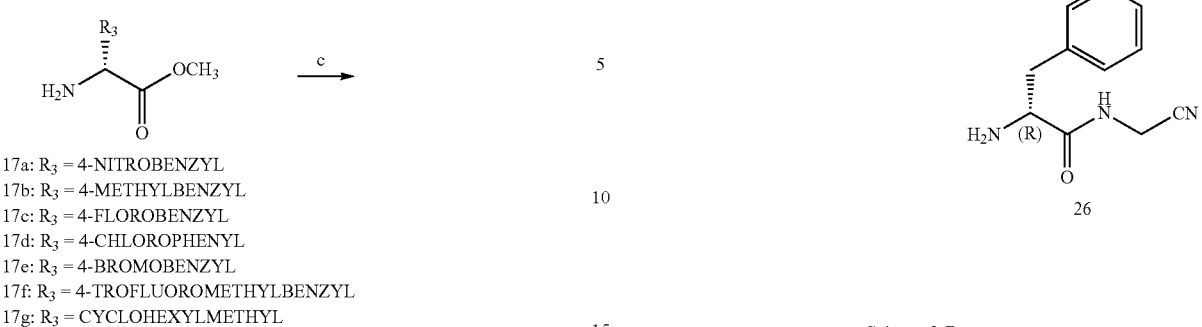

17a: R₃ = 4-NITROBENZYL
17b: R₃ = 4-METHYLBENZYL
17c: R₃ = 4-FLOROBENZYL
17d: R₃ = 4-CHLOROPHENYL
17e: R₃ = 4-BROMOBENZYL
17f: R₃ = 4-TROFLUOROMETHYLBENZYL
17g: R₃ = CYCLOHEXYLMETHYL

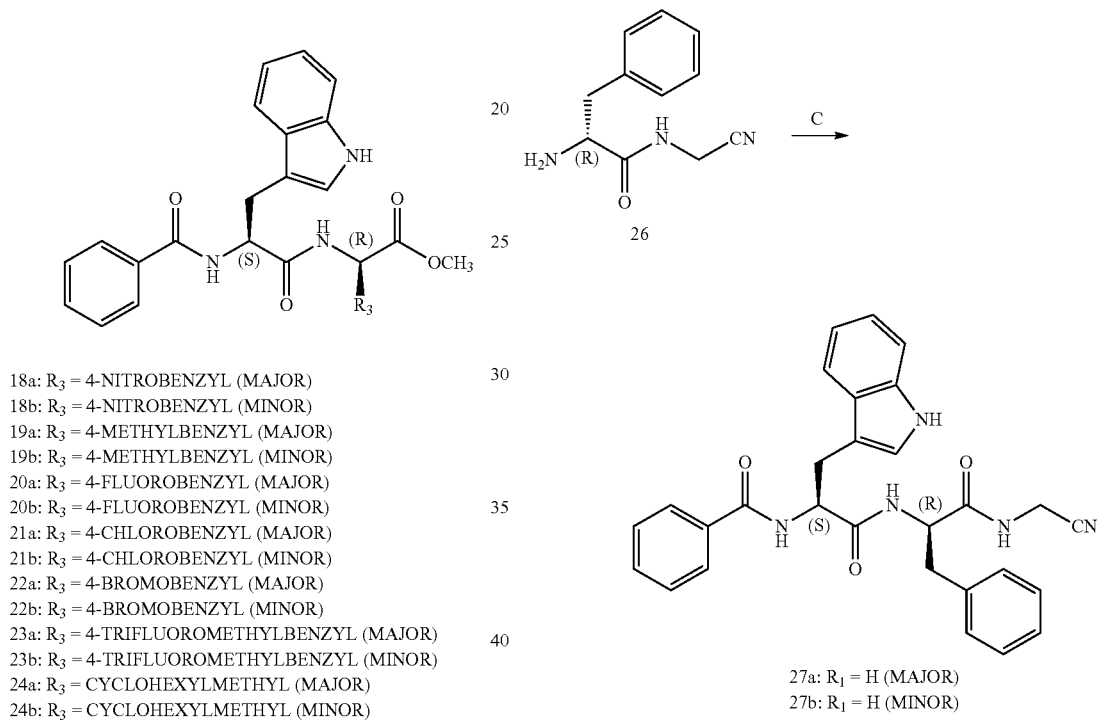

18a: R₃ = 4-NITROBENZYL (MAJOR)
18b: R₃ = 4-NITROBENZYL (MINOR)
19a: R₃ = 4-METHYLBENZYL (MAJOR)
19b: R₃ = 4-METHYLBENZYL (MINOR)
20a: R₃ = 4-FLUOROBENZYL (MAJOR)
20b: R₃ = 4-FLUOROBENZYL (MINOR)
21a: R₃ = 4-CHLOROBENZYL (MAJOR)
21b: R₃ = 4-CHLOROBENZYL (MINOR)
22a: R₃ = 4-BROMOBENZYL (MAJOR)
22b: R₃ = 4-BROMOBENZYL (MINOR)
23a: R₃ = 4-TRIFLUOROMETHYLBENZYL (MAJOR)
23b: R₃ = 4-TRIFLUOROMETHYLBENZYL (MINOR)
24a: R₃ = CYCLOHEXYLMETHYL (MAJOR)
24b: R₃ = CYCLOHEXYLMETHYL (MINOR)

Scheme 3 is for the synthesis of N—(N-benzoyl-L-tryptophanyl)-para-substituted-D-phenylalanine methyl esters and N—(N-benzoyl-L-tryptophanyl)-3-cyclohexyl-D-alanine methyl esters, with which compounds 25-27 are synthesized.

Reagents and conditions: (a) 20% TFA (TFA-DCM=1:4), 30 min; (b) MeOH-c-H2SO4, reflux, 2 h; and (c) N-benzoyl-L-tryptophan, HBTU, DIEA, DCM, 6 h.

Scheme 3-A

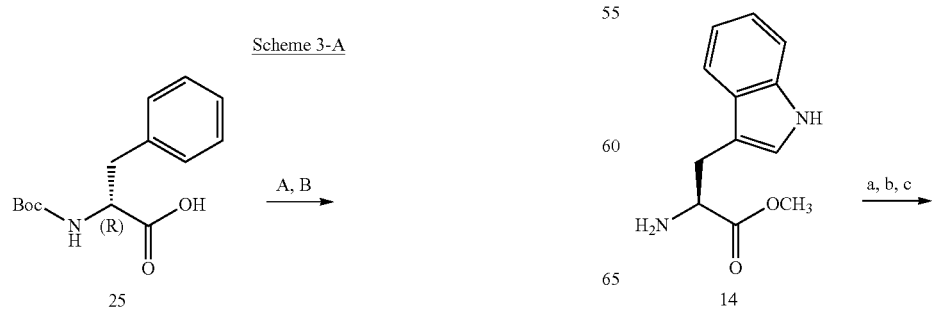

Scheme 4 is for the preparation of N—(N-benzoyl-L-tryptophanyl)-D-phenylalanine-glycine-nitriles, with which compounds 14-15 are synthesized.

Reagents and conditions: (a) aminoacetonitrile, HBTU, DIEA, DCM, 6 h; (b) 20% TFA (TFA-DCM=1:4), 30 min; and (c) N-benzoyl-L-t tophan, HBTU, DIEA, DCM, 6 h.

Scheme 4

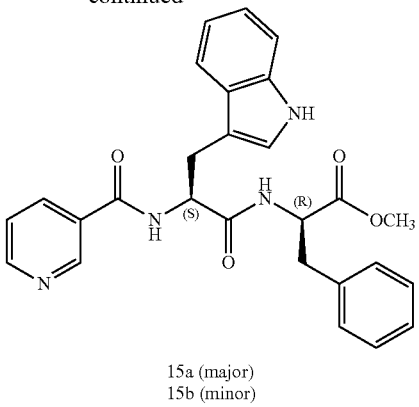

15a (major)
15b (minor)

Measurement of Elastase Release

Degranulation of azurophilic granules was determined by elastase release as described above. Experiments were performed using MeO-Suc-Ala-Ala-Pro-Val-p-nitroanilide as the elastase substrate. Briefly, after supplementation with MeO-Suc-Ala-Ala-Pro-Val-p-nitroanilide (100 μM), neutrophils ($6 \times 10^5$ ml$^{-1}$) were equilibrated at 37° C. for 2 min and incubated with drugs for 5 min. Cells were activated by 30 nM fMLP or 1.5 nM WKYMVm for 10 min with the pre-process of 0.5 μg ml$^{-1}$ CB for 3 min, and changes in absorbance at 405 nm were continuously monitored to evaluate elastase release. Results are expressed as the percentage of elastase release in the drug-free control group, DMSO.

Tables 1-6 demonstrate the inhibitory effects of dipeptide derivatives in the present invention on superoxide anion generation and elastase release by human neutrophils in response to specific activators of FPR1 or FPR2.

Table 1 demonstrates the inhibitory effects of N—(N-aroyl-L-tryptophanyl)-D-phenylalanine methyl esters and their analogs on $O_2^{\cdot-}$ generation and elastase release by human neutrophils in response to fMLP/CB.

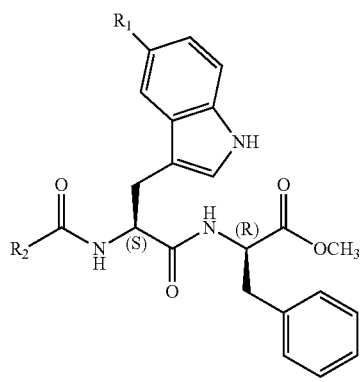

TABLE 1

| | | | Anti-inflammation[a] (μM) | |
|---|---|---|---|---|
| | $R_1$ | $R_2$ | $O_2^{\cdot-}$ generation | NE release |
| EFB-1[b] | | | 0.16 ± 0.01 | |
| Sivelestat[b] | | | | 0.046 ± 0.020 |
| 1 | | | >20[c] | 1.70 ± 0.60[c] |
| 3 (HCH6-1) | H | Phenyl | 0.23 ± 0.02 | 0.60 ± 0.07 |

TABLE 1-continued

| | | | Anti-inflammation[a] (μM) | |
|---|---|---|---|---|
| | $R_1$ | $R_2$ | $O_2^{\cdot-}$ generation | NE release |
| 4 | H | 4-fluorophenyl | >30 | >30 |
| 5 | H | 4-chlorophenyl | >30 | 10.40 ± 4.61 |
| 6 | H | 4-methylphenyl | 1.88 ± 0.29 | 2.47 ± 0.25 |
| 7 | H | 4-methoxyphenyl | >30 | >30 |
| 8 | H | Benzyl | 10.17 ± 4.53 | 5.71 ± 0.39 |
| 9 | H | Benzylmethyl | 10.10 ± 3.05 | 12.54 ± 4.87 |
| 10 | H | Benzyloxyl | 17.43 ± 1.85 | 8.92 ± 4.84 |
| 11a | OH | Phenyl | 8.81 ± 1.22 | 9.11 ± 0.76 |
| 11b | OH | Phenyl | 18.67 ± 4.02 | 22.11 ± 4.96 |
| 15a | H | Pyridinyl | 13.11 ± 0.50 | >30 |
| 15b | H | Pyridinyl | >30 | >30 |

(note)
[a]The IC$_{50}$ values are presented as mean ± SEM. (n = 3).
[b]Sivelestat and EFB-1 were used as positive controls in the present invention.
[c]The biological data were from the literature directly.

Table 2 demonstrates the inhibitory effects of N—(N-benzoyl-L-tryptophanyl)-para-substituted-D-phenylalanine methyl esters and N—(N-benzoyl-L-tryptophanyl)-3-cyclohexyl-Dalanine methyl esters on $O_2^{\cdot-}$ generation and elastase release by human neutrophils in response to fMLP/CB.

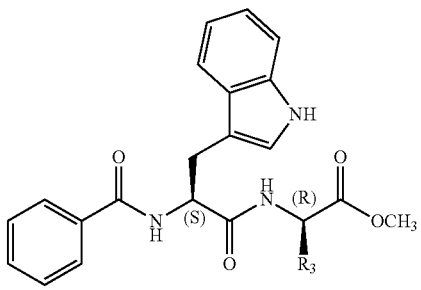

TABLE 2

| | | Anti-inflammation[a] (μM) | |
|---|---|---|---|
| | $R_3$ | $O_2^{\cdot-}$ generation | NE release |
| EFB-1[b] | | 0.16 ± 0.01 | |
| Sivelestat[b] | | | 0.046 ± 0.020 |
| 3(HCH6-1) | benzyl | 0.23 ± 0.02 | 0.60 ± 0.07 |
| 18a | 4-nitrobenzyl | 18.99 ± 2.70 | 11.17 ± 0.46 |
| 18b | | 13.08 ± 0.40 | 15.39 ± 0.54 |
| 19a | 4-methylbenzyl | 1.87 ± 0.22 | 3.60 ± 0.05 |
| 19b | | 18.83 ± 5.80 | 23.99 ± 2.02 |
| 20a | 4-fluorobenzyl | 5.40 ± 1.50 | 11.49 ± 2.20 |
| 20b | | 14.01 ± 1.21 | 19.37 ± 0.71 |
| 21a | 4-chlorobenzyl | 4.41 ± 0.27 | 4.31 ± 0.52 |
| 21b | | 5.26 ± 0.84 | 12.41 ± 3.53 |
| 22a | 4-bromobenzyl | 6.82 ± 3.09 | 2.41 ± 1.60 |
| 22b | | 15.97 ± 0.83 | 7.20 ± 3.36 |
| 23a | 4-trifluoro- | 17.25 ± 1.94 | 21.05 ± 2.92 |
| 23b | methylbenzyl | 3.16 ± 0.52 | 8.76 ± 2.33 |
| 24a | cyclohexylmethyl | 0.12 ± 0.02 | 0.37 ± 0.04 |
| 24b | | 1.32 ± 0.14 | 1.03 ± 0.02 |

(note)
[a]The IC$_{50}$ values are presented as mean ± SEM (n = 3).
[b]Sivelestat and EFB-1 were used as positive controls in the present invention.

Table 3 demonstrates the inhibitory effects of N—(N-benzoyl-L-tryptophanyl)-D-phenylalanine analogs/derivatives on $O_2.^-$ generation and elastase release by human neutrophils in response to fMLP/CB.

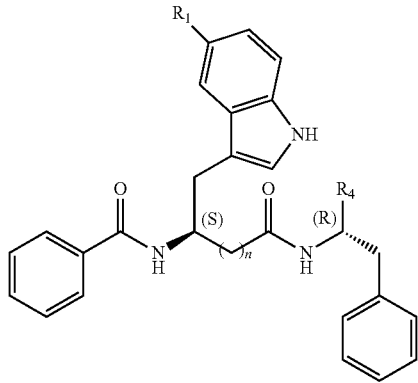

TABLE 3

| | $R_1$ | $R_4$ | Anti-inflammation[a] (µM) | |
|---|---|---|---|---|
| | | | $O_2^{\cdot-}$ generation | NE release |
| EFB-1[b] | | | 0.16 ± 0.01 | |
| Sivelestat[b] | | | | 0.046 ± 0.020 |
| 3(HCH6-1) | H | COOCH$_3$ | 0.23 ± 0.02 | 0.60 ± 0.07 |
| 27a | H | CONHCH$_2$CN | 4.23 ± 2.44 | 4.69 ± 0.80 |
| 27b | H | CONHCH$_2$CN | 10.51 ± 4.23 | 14.51 ± 2.87 |
| 12a | OH | CH$_2$OH | >30 | >30 |
| 12b | OH | CH$_2$OH | >30 | >30 |
| 13a | H | CH$_2$OH | >30 | >30 |
| 13b | H | CH$_2$OH | >30 | >30 |

(note)
[a] The IC$_{50}$ values are presented as mean ± SEM (n = 3).
[b] Sivelestat and EFB-1 were used as positive controls in the present invention.

Table 4 demonstrates respectively inhibitory the effects of compounds 3, 6, 24a, and 24b on $O_2.^-$ generation and elastase release by human neutrophils in response to fMLP/CB and WKYMVm/CB.

TABLE 4

| | fMLF/CB (µM)[a] | | WKYMVm/CB (µM)[a] | |
|---|---|---|---|---|
| compounds | $O_2^{\cdot-}$ generation | NE release | $O_2^{\cdot-}$ generation | NE release |
| CycH[b] | 0.04 ± 0.01 | 0.04 ± 0.01 | 2.02 ± 0.18 | 0.17 ± 0.01 |
| WRW4[b] | 2.26 ± 0.48 | 1.14 ± 0.27 | 0.38 ± 0.01 | 0.59 ± 0.09 |
| 3(HCH6-1) | 0.23 ± 0.02 | 0.60 ± 0.07 | 4.83 ± 0.66 | 4.61 ± 0.72 |
| 6 | 1.88 ± 0.29 | 2.47 ± 0.25 | 6.55 ± 0.59 | 1.96 ± 0.11 |
| 24a | 0.12 ± 0.02 | 0.37 ± 0.04 | 1.58 ± 0.04 | 1.62 ± 0.04 |
| 24b | 1.32 ± 0.14 | 1.03 ± 0.02 | 4.27 ± 0.31 | 1.06 ± 0.05 |

(note)
[a] The IC$_{50}$ values are presented as mean ± SEM (n = 3).
[b] Cyclosporin H (CycH) and WRW4 were used as positive controls.

Tables 5 and 6 explore whether there is an anti-inflammatory effect in the dipeptide derivatives. Because ferricytochrome c cannot penetrate cell membranes, it reacts with superoxide anion extracellularly. Also, there are absorptive reactions at 550 nm, and differences among the absorptive reactions can be used to evaluate the influence on the release of superoxide anion. The elastase is released by degranulation as the neutrophil is activated. Tables 5 and 6 use the substrate, MeO-Suc-Ala-Ala-Pro-Val-p-nitroanilide, with the specificity for reacting with the elastase so as to evaluate the influence of the candidate compound on the elastase release.

Table 5 demonstrates the comparison for each of compound 3 (HCH6-1), compound 6 (HCH30-2), compound 19a (HCH108-4), compound 19b (HCH108-3), compound 22a (HCH113-4), compound 22b (HCH113-3), compound 24a (HCH99-2), compound 24b (HCH99-1), compound 27a (HCH90-2-2) and compound 27b (HCH90-2-1) inhibiting superoxide anion generation of human neutrophils induced by specific activator of FPR1, fMLP and specific activator of FPR2, WKYMVm. The IC$_{50}$ values in Tables 5-6 are presented as mean±SEM (n=4 or 8), ***p<0.001 (compared to the control), and Inh % is the inhibitory percentage under 10 µM.

TABLE 5

| | Superoxide anion | | | |
|---|---|---|---|---|
| | fMLF | | WKYMVm | |
| Compound | IC$_{50}$ (µM)[a] | Inh % | IC$_{50}$ (µM)[a] | Inh % |
| HCH 30-2 | 1.88 ± 0.29 | — | 6.55 ± 0.59 | — |
| HCH 90-2-1 | — | 34.61 ± 4.1 *** | — | 18.66 ± 0.7 *** |
| HCH 90-2-2 | 6.23 ± 1.05 | — | — | 28.79 ± 2.6 *** |
| HCH 99-1 | 1.32 ± 0.14 | — | 4.27 ± 0.31 | — |
| HCH 99-2 | 0.19 ± 0.07 | — | 1.58 ± 0.04 | — |
| HCH 108-3 | 1.87 ± 0.22 | — | — | 31.00 ± 2.7 *** |
| HCH 108-4 | 4.88 ± 0.18 | — | 4.06 ± 0.77 | — |
| HCH 113-3 | 1.41 ± 0.26 | — | 5.39 ± 0.45 | — |
| HCH 113-4 | 0.83 ± 0.05 | — | 2.14 ± 0.36 | — |
| HCH 6-1 | 0.32 ± 0.03 | — | 4.98 ± 0.27 | — |

Table 6 demonstrates the comparison for each of compound 3 (HCH6-1), compound 6 (HCH30-2), compound 19a (HCH108-4), compound 19b (HCH108-3), compound 22a (HCH113-4), compound 22b (HCH113-3), compound 24a (HCH99-2), compound 24b (HCH99-1), compound 27a (HCH90-2-2) and compound 27b (HCH90-2-1) inhibiting elastase release of human neutrophils induced by specific activator of FPR1, fMLP and specific activator of FPR2, WKYMVm. The $IC_{50}$ values in Tables 5-6 are presented as mean±SEM (n=4 or 8), ***p<0.001 (compared to the control), and Inh % is the inhibitory percentage under 10 μM.

TABLE 6

| | Elastase release | | | |
| --- | --- | --- | --- | --- |
| | fMLF | | WKYMVm | |
| Compound | $IC_{50}$ (μM)$^a$ | Inh % | $IC_{50}$ (μM)$^a$ | Inh % |
| HCH 30-2 | 2.47 ± 0.25 | — | 1.96 ± 0.11 | — |
| HCH 90-2-1 | — | 18.66 ± 0.7 *** | 6.65 ± 0.23 | — |
| HCH 90-2-2 | — | 28.79 ± 2.6 *** | — | 35.9 ± 0.8 *** |
| HCH 99-1 | 1.03 ± 0.02 | — | 1.06 ± 0.05 | — |
| HCH 99-2 | 0.37 ± 0.04 | — | 1.62 ± 0.04 | — |
| HCH 108-3 | 3.60 ± 0.05 | 31.00 ± 2.7 *** | 2.07 ± 0.21 | — |
| HCH 108-4 | 1.24 ± 0.04 | — | 6.04 ± 0.47 | — |
| HCH 113-3 | 1.87 ± 0.03 | — | 7.31 ± 0.63 | — |
| HCH 113-4 | 0.89 ± 0.06 | — | 3.15 ± 0.32 | — |
| HCH 6-1 | 0.57 ± 0.07 | — | 5.22 ± 0.70 | — |

Please refer to Tables 5-6. By fMLF (FPR1 activator) triggering neutrophils, it can be seen that a series of dipeptide derivatives is capable of inhibiting superoxide anion and elastase, which are released by human neutrophils. WKYMVm (FPR1/2 activator) is utilized to stimulate the cells, and then the inhibitory effect becomes weak. It is found that these dipeptide derivatives selectively inhibit activated neutrophils induced by fMLP. From tables 5 and 6, it can be found that HCH99-2 (compound 24a) and HCH6-1 (compound 3) expressed excellent inhibitory effect with $IC_{50}$ being 0.19±0.07 μM and 0.32±0.03 μM respectively. For the selectivity for FPR1/2 and FPR1, the differences became 8 fold for compound 24a and 15 fold for compound 3.

Embodiments 1-5 are preparing methods for the dipeptide derivatives in the present invention.

[Embodiment 1] General procedure for the synthesis of N—(N-aroyl-L-tryptophanyl)-D-phenylalanine methyl esters (compounds 3-7) and their analogs (compounds 8-10, 11a and 11b)

To a mixture solution of L-tryptophan (2a, 1.0 equiv.) or 5-hydroxy-L-tryptophan (2b, 1.0 equiv.) in 2 N NaOH aqueous solution was added suitable acyl chlorides (1.1 equiv.), respectively. The reaction mixture was stirred at room temperature for 3.0 h, and then 1 N HCl solution was added and the pH values were adjusted to 1-2. The mixture solution was further partitioned by chloroform, and the organic layer was evaporated at reduced pressure to yield intermediates. The intermediates and D-phenylalanine methyl ester (1.0 mmole) were dissolved in DCM, and then HBTU (2.0 equiv.) and DIEA (1.5 equiv.) were added. The reaction mixture was stirred for 6 hours at room temperature, concentrated, and purified by silica gel column chromatography using a mixture of n-hexane-ethyl acetate (6:4) or n-hexane-acetone (7:3), respectively, to afford products (compounds 3-10, 11a and 11b).

Compound 3, Also Known as HCH6-1

N—(N-Benzoyl-L-tryptophanyl)-D-phenylalanine methyl ester

52% yield. White powder, mp 174-176° C. CD (c 0.11 mM, MeOH) nm (mdeg) 261 (−0.43), 253 (−0.40), 239 (−0.01), 223 (0.46) nm. $^1$H NMR ($C_5D_5N$) δ 11.79 (1H, s, NH), 9.41 (1H, d, J=8.0 Hz, CONH), 9.06 (1H, d, J=8.0 Hz, NH), 8.06 (2H, d, J=7.2 Hz), 7.88 (1H, d, J=8.0 Hz), 7.54 (1H, d, J=8.0 Hz), 7.36-7.12 (11H, m), 5.67 (1H, ddd, J=14.4, 7.2, 7.2 Hz), 5.23 (1H, ddd, J=14.0, 7.2, 7.2 Hz), 3.77 (1H, dd, J=14.6, 7.2 Hz), 3.63 (1H, dd, J=14.4, 6.8 Hz), 3.50 (3H, s), 3.20 (1H, dd, J=13.6, 7.2 Hz), 3.09 (1H, dd, J=13.6, 7.2 Hz). 13C NMR (C5D5N) δ 172.9 (s), 172.5 (s), 168.0 (s), 137.7 (3×C, s), 131.6 (d), 130.0 (2×C, d), 129.0 (2×C, d), 128.9 (s), 128.7 (2×C, d), 128.2 (2×C, d), 127.3 (d), 124.6 (d), 122.0 (d), 119.5 (2×C, d), 112.2 (d), 111.4 (s), 55.5 (d), 54.6 (d), 52.0 (q), 38.2 (t), 29.20 (t). ESI-MS (m/z, %): 492 [M+Na]$^-$ (100), 470 [M+1]$^+$ (44). HR-ESI-MS m/z 492.1901 [M+Na]$^+$ (calcd for $C_{28}H_{27}N_3O_4Na$ 492.1899).

Compound 4

N—(N-4-Fluorobenzoyl-L-tryptophanyl)-D-phenylalanine methyl ester

31% yield. White powder, mp 191-193° C. $^1$H NMR ($C_5D_5N$) δ 11.81 (1H, s), 9.48 (1H, d, J=8.0 Hz), 9.11 (1H, d, J=8.0 Hz), 8.04 (2H, dd, J=8.0 Hz), 7.87 (1H, d, J=7.6 Hz), 7.52 (1H, d J=8.0 Hz, H–7), 7.32 (1H, s), 7.26-7.13 (7H, m), 7.02 (2H, t, J=8.6 Hz), 5.66 (1H, ddd, J=14.6, 7.2, 7.2 Hz), 5.24 (1H, ddd, J=14.2, 7.2, 7.2 Hz), 3.75 (1H, dd, J=14.4, 6.8 Hz), 3.61 (1H, dd, J=14.4, 6.8 Hz), 3.51 (3H, s), 3.20 (1H, dd, J=14.2, 7.2 Hz), 3.09 (1H, dd, J=14.2, 7.2 Hz). $^{13}$C NMR ($C_5D_5N$) δ 174.4 (s), 174.0 (s), 168.4 (s), 166.4 (s, $J_{C-F}$=248.0 Hz), 139.2 (2×C, s), 133.5 (s), 132.2 (2×C, d, $J_{C-F}$=9.0 Hz), 131.5 (2×C, d), 130.5 (2×C, d), 130.4 (s), 128.8 (d), 126.1 (d), 123.5 (d), 121.0 (2×C, d), 117.0 (2×C, d, $J_{C-F}$=22.0 Hz), 113.7 (d), 112.9 (s), 57.1 (d), 56.1 (d), 53.6 (q), 39.7 (t), 30.7 (t). ESI-MS (m/z, %): 510 [M+Na]$^+$ (100), 488 [M+1]$^+$ (37). HRESI-MS m/z 510.1802 [M+Na]$^+$ (calcd for $C_{28}H_{26}FN_3O_4Na$ 510.1805).

Compound 5

N—(N-4-Chlorobenzoyl-L-tryptophanyl)-D-phenylalanine methyl ester

23% yield. White powder, mp 191-193° C. $^1$H NMR ($C_5D_5N$) δ 11.82 (1H, s), 9.48 (1H, d, J=7.6 Hz), 9.18 (1H, d, J=8.0 Hz), 7.96 (2H, d, J=8.4), 7.85 (1H, d, J=8.0 Hz), 7.51 (1H, d, J=8.0 Hz), 7.28 (1H, s), 7.26-7.12 (9H, m), 5.65 (1H, ddd, J=14.6, 6.8, 6.8 Hz), 5.24 (1H, ddd, J=14.0, 7.6, 7.6 Hz), 3.74 (1H, dd, J=14.4, 6.8 Hz), 3.59 (1H, dd, J=14.2, 7.2 Hz), 3.50 (3H, s), 3.20 (1H, dd, J=13.8, 7.6 Hz), 3.08 (1H, dd, J=13.6, 7.6 Hz). $^{13}$C NMR (C$_5$D$_5$N) δ 172.8 (s), 172.5 (s), 166.9 (s), 137.7 (s), 137.3 (s), 135.7 (s), 134.2 (s), 130.0 (2×C, d), 129.9 (2×C, d), 129.0 (2×C, d), 128.9 (s), 128.8 (2×C, d), 127.3 (d), 124.5 (d), 122.0 (d), 119.5 (2×C, d), 112.2 (d), 111.3 (s), 55.6 (d), 54.6 (d), 52.0 (q), 38.2 (t), 29.1 (t). ESI-MS (m/z, %): 526 [M+Na]$^+$ (100), 504 [M+1]$^+$ (33). HR-ESI-MS m/z 526.1506 [M+Na] (calcd for C$_{28}$H$_{26}$ClN$_3$O$_4$Na 526.1509).

Compound 6

N—(N-4-Methylbenzoyl-L-tryptophanyl)-D-phenylalanine methyl ester

39% yield. White powder, mp 169-171° C. $^1$H NMR (C$_5$D$_5$N) δ 11.77 (1H, s), 9.41 (1H, d, J=8.0 Hz), 8.98 (1H, d, J=8.0 Hz), 8.00 (2H, d, J=8.0 Hz), 7.89 (1H, d, J=7.6 Hz), 7.54 (1H, d, J=8.4 Hz), 7.33 (1H, s), 7.30-7.14 (7H, m), 7.05 (2H, d, J=7.6 Hz), 5.69 (1H, ddd, J=14.4, 6.8, 6.8 Hz), 5.23 (1H, ddd, J=14.0, 7.2, 7.2 Hz), 3.79 (1H, dd, J=14.6, 6.8 Hz), 3.65 (1H, dd, J=14.4, 6.8 Hz), 3.51 (3H, s), 3.21 (1H, dd, J=13.8, 6.8 Hz), 3.09 (1H, dd, J=13.6, 7.2 Hz), 2.13 (3H, s). $^{13}$C NMR (C$_5$D$_5$N) δ 174.5 (s), 174.0 (s), 169.5 (s), 143.4 (s), 139.2 (2×C, s), 134.3 (s), 131.5 (2×C, d), 130.9 (2×C, d), 130.5 (2×C, d), 130.4 (s), 129.8 (2×C, d), 128.8 (d), 126.1 (d), 123.5 (d), 121.0 (2×C, d), 113.7 (d), 112.9 (s), 57.0 (d), 56.2 (d), 53.6 (q), 39.7 (t), 30.7 (t), 22.9 (q). ESI-MS (m/z, %): 506 [M+Na]$^+$ (99), 484 [M+1]$^+$ (100). HR-ESI-MS m/z 506.2059 [M+Na]$^+$ (calcd for C$_{29}$H$_{29}$N$_3$O$_4$Na 506.2056).

Compound 7

N—(N-4-Methoxylbenzoyl-L-tryptophanyl)-D-phenylalanine methyl ester

47% yield. White powder, mp 151-153° C. $^1$H NMR (C$_5$D$_5$N) δ 11.80 (1H, s), 9.39 (1H, d, J=8.0 Hz), 8.92 (1H, d, J=8.0 Hz), 8.09 (2H, d, J=8.4 Hz), 7.99 (1H, d, J=8.0 Hz), 7.53 (1H, d, J=8.0 Hz), 7.33 (1H, s), 7.33-7.13 (7H, m), 6.88 (2H, d, J=8.4 Hz), 5.69 (1H, ddd, J=14.4, 6.8, 6.8 Hz), 5.23 (1H, ddd, J=14.0, 7.2, 7.2 Hz), 3.78 (1H, dd, J=14.2, 6.8 Hz), 3.64 (1H, dd, J=14.6, 6.8 Hz), 3.59 (3H, s), 3.50 (3H, s), 3.20 (1H, dd, J=13.6, 7.2 Hz), 3.09 (1H, dd, J=13.6, 7.6 Hz). $^{13}$C NMR (C$_5$D$_5$N) δ 174.6 (s), 174.0 (s), 169.0 (s), 164.1 (s), 139.2 (2×C, s), 131.6 (2×C, d), 131.5 (2×C, d), 130.5 (2×C, d), 130.4 (s), 129.4 (s), 128.8 (d), 126.1 (d), 123.5 (d), 121.0 (2×C, d), 115.6 (2×C, d), 113.7 (d), 113.0 (s), 57.0 (q), 56.9 (d), 56.1 (d), 53.6 (q), 39.03 (t), 30.7 (t). ESI-MS (m/z, %): 522 [M+Na] (100), 500 [M+1]$^+$ (38). HR-ESI-MS m/z 522.2007 [M+Na]$^+$ (calcd for C$_{29}$H$_{29}$N$_3$O$_5$Na 522.2005).

Compound 8

N—(N-Phenylacetyl-L-tryptophanyl)-D-phenylalanine methyl ester

43% yield. White powder, mp 182-184° C. $^1$HNMR (C$_5$D$_5$N) δ 11.76 (1H, s), 9.34 (1H, d, J=8.0 Hz), 8.98 (1H, d, J=8.4 Hz), 7.81 (1H, d, J=8.0 Hz), 7.53 (1H, d, J=8.4 Hz), 7.33 (2H, d, J=7.2 Hz), 7.27-7.13 (11H, m), 5.50 (1H, ddd, J=14.6, 6.8, 6.8 Hz), 5.19 (1H, ddd, J=14.0, 7.2, 7.2 Hz), 3.75-3.46 (4H, m), 3.49 (3H, s), 3.17 (1H, dd, J=13.6, 6.8 Hz), 3.05 (1H, dd, J=13.8, 6.8 Hz). $^{13}$C NMR (C$_5$D$_5$N) δ 172.8 (s), 172.5 (s), 171.1 (s), 137.7 (s), 137.6 (s), 136.9 (s), 130.0 (2×C, d), 129.9 (2×C, d), 129.0 (2×C, d), 128.9 (s), 128.9 (2×C, d), 127.3 (d), 127.0 (d), 124.5 (d), 121.9 (d), 119.5 (d), 119.4 (d), 112.1 (d), 111.2 (s), 54.9 (d), 54.6 (d), 52.0 (q), 43.5 (t), 38.2 (t), 29.3 (t). ESI-MS (m/z, %): 506 [M+Na]$^+$ (100), 484 [M+1]$^+$ (87). HR-ESI-MS m/z 506.2060 [M+Na]$^+$ (calcd for C$_{29}$H$_{29}$N$_3$O$_4$Na 506.2056).

Compound 9

N—(N-Phenylpropanoyl-L-tryptophanyl)-D-phenylalanine methyl ester

24% yield. White powder, mp 159-161° C. $^1$H NMR (C$_5$D$_5$N) δ 11.78 (1H, s), 9.27 (1H, d, J=8.0 Hz), 8.88 (1H, d, J=8.4 Hz), 7.85 (1H, d, J=7.6 Hz), 7.55 (1H, d, J=7.6 Hz), 7.27-7.12 (13H, m), 5.52 (1H, ddd, J=14.8, 7.2, 7.2 Hz), 5.21 (1H, ddd, J=14.0, 7.2, 7.2 Hz), 3.65 (1H, dd, J=14.4, 6.8 Hz), 3.50 (3H, s), 3.50-3.45 (1H, m), 3.17 (1H, J=13.6, 6.8 Hz), 3.09-2.97 (3H, m), 2.67-2.61 (2H, m). $^{13}$C NMR (C$_5$D$_5$N) δ 174.4 (s), 174.0 (s), 173.9 (s), 143.7 (s), 139.2 (2×C, s), 131.5 (2×C, d), 130.5 (2×C, d), 130.4 (d), 130.4 (d), 130.3 (2×C, d), 128.8 (s), 128.0 (d), 126.0 (d), 123.4 (d), 121.0 (d), 120.9 (d), 113.6 (d), 112.9 (s), 56.4 (d), 56.0 (d), 53.5 (q), 39.7 (2×C, t), 33.7 (t), 30.8 (t). ESI-MS (m/z, %): 520 [M+Na]$^+$ (100), 498 [M+1]$^+$ (39). HR-ESI-MS m/z 520.2215 [M+Na]$^+$ (calcd for C$_{29}$H$_{29}$N$_3$O$_4$Na 520.2212).

Compound 10

N—(N-Benzyloxycarbonyl-L-tophanyl)-D-phenylalanine methyl ester

67% yield. White powder, mp 147-149° C. $^1$H NMR (C$_5$D$_5$N) S 11.76 (1H, s), 9.32 (1H, d, J=7.6 Hz), 8.63 (1H, d, J=8.4 Hz), 7.88 (1H, d, J=7.6 Hz), 7.54 (1H, d, J=8.4 Hz), 7.32-7.14 (13H, m), 5.25-5.13 (4H, m), 3.72 (1H, dd, J=14.4, 7.2 Hz), 3.55 (1H, dd, J=14.8, 7.2 Hz), 3.49 (3H, s), 3.17 (1H, dd, J=13.6, 7.2 Hz), 3.07 (1H, dd, J=13.8, 7.2 Hz). 13C NMR (C5D5N) δ δ 172.9 (s), 172.5 (s), 157.2 (s), 137.9 (s), 137.7 (2×C, s), 130.0 (2×C, d), 129.0 (2×C, d), 129.0 (d), 128.9 (2×C, d), 128.9 (s), 128.3 (2×C, d), 127.3 (s), 124.6 (d), 122.0 (d), 119.5 (2×C, d), 112.2 (d), 111.3 (s), 66.6 (t), 57.0 (d), 54.5 (d), 52.0 (q), 38.2 (t), 29.7 (t). ESI-MS (m/z, %): 522 [M+Na]$^+$ (100), 500 [M+1]$^+$ (30). HR-ESI-MS m/z 522.2008 [M+Na]$^+$ (calcd for C$_{29}$H$_{29}$N$_3$O$_5$Na 522.2005).

N—(N-Benzoyl-5-hydroxy-L-tryptophanyl)-D-phenylalanine methyl esters (compounds 11a and 11b)

Compound 11a

23% yield. White powder, mp 112-114° C. $^1$H NMR (CDCl$_3$) δ 11.54 (1H, s, NH), 9.39 (1H, d, J=8.0 Hz, NH), 9.04 (1H, d, J=8.0 Hz, NH), 8.06 (2H, d, J=7.2 Hz), 7.74 (1H, d, J=2.0 Hz), 7.47 (1H, d, J=8.8 Hz), 7.35 (1H, t, J=7.2 Hz), 7.29-7.13 (9H, m), 5.65 (1H, dd, J=14.2, 7.2 Hz), 5.23 (1H, dd, J=14.2, 7.2 Hz), 3.72 (1H, dd, J=14.2, 7.2 Hz), 3.59 (1H, dd, J=14.2, 7.2 Hz), 3.47 (3H, s), 3.15 (1H, dd, J=13.6, 7.2 Hz), 3.05 (1H, dd, J=13.6, 7.2 Hz). $^{13}$C NMR (CDCl$_3$) δ 172.7 (s), 172.3 (s), 167.7 (s), 152.4 (s), 137.4 (s), 135.5 (s), 132.2 (s), 131.4 (d), 129.8 (s), 129.8 (2×C, d), 128.8 (2×C, d), 128.5 (2×C, d), 128.0 (2×C, d), 127.1 (d), 125.0 (d), 112.8 (d), 112.6 (d), 110.3 (s), 103.9 (d), 55.5 (d), 54.5 (d), 51.8 (q), 38.0 (t), 29.2 (t). ESI-MS (m/z, %): 508 [M+Na]+ (100). HR-ESI-MS m/z 508.1850 [M+Na]+ (calcd for $C_{28}H_{27}N_3O_5Na$ 508.1848).

Compound 11b

17% yield. White powder, mp 110-112° C. $^1$H NMR (CDCl$_3$) δ 11.53 (1H, s, NH), 9.41 (1H, d, J=8.0 Hz, NH), 9.11 (1H, d, J=8.0 Hz, NH), 8.10 (2H, d, J=8.0 Hz), 7.64 (1H, d, J=1.6 Hz), 7.43 (1H, d, J=8.0 Hz), 7.37 (1H, t, J=7.6 Hz), 7.30 (2H, t, J=7.6 Hz), 7.26 (2H, t, J=7.6 Hz), 7.19-7.13 (4H, m), 7.08 (1H, t, J=8.0 Hz), 5.65 (1H, dd, J=14.4, 7.2 Hz), 5.21 (1H, dd, J=14.2, 7.2 Hz), 3.74 (1H, dd, J=14.4, 7.2 Hz), 3.61 (1H, dd, J=14.4, 7.2 Hz), 3.55 (3H, s), 3.27 (1H, dd, J=13.6, 7.2 Hz), 3.15 (1H, dd, J=13.6, 7.2 Hz). $^{13}$C NMR (CDCl$_3$) δ 172.6 (s), 172.3 (s), 167.8 (s), 152.3 (s), 137.5 (s), 135.5 (s), 132.2 (s), 131.4 (d), 129.8 (2×C, d), 129.7 (s), 128.7 (2×C, d), 128.6 (2×C, d), 128.1 (2×C, d), 127.0 (d), 125.0 (d), 112.8 (d), 112.5 (d), 110.3 (s), 103.9 (d), 55.2 (d), 54.5 (d), 51.9 (q), 38.2 (t), 28.9 (t). ESI-MS (m/z, %): 508 [M+Na]+ (100). HR-ESI-MS m/z 508.1851 [M+Na]+ (calcd for $C_{28}H_{27}N_3O_5Na$ 508.1848).

[Embodiment 2] General procedure for the synthesis of N—(N-benzoyl-L-tryptophanyl)-D-phenylalaninol derivatives (compounds 12a-13a and 12b-13b)

N-Benzoyl-L-tryptophan and N-benzoyl-5-hydroxy-L-tryptophan were obtained by a similar procedure as described above. Dissolve N-benzoyl-L-tryptophan (1.0 equiv.) or N-benzoyl-5-hydroxy-L-tryptophan (1.0 equiv.) in DCM respectively, and then D-phenylalaninol (1.0 equiv.), HBTU (2.0 equiv.) and DIEA (1.5 equiv.) were added. The reaction mixture was stirred at room temperature for 6.0 h, and purified by silica gel column chromatography using ethyl acetate or MeOH-CHCl3 (1:20) to afford the mixtures 12a/b and 13a/b. The mixture was further purified by HPLC (mobile phase: 35% acetonitrile+0.3% TFA) to afford products.

N—(N-Benzoyl-L-tryptophanyl)-5-hydroxy-D-phenylalaninol (compounds 12a and 12b)

Compound 12a

16% yield. White powder, mp 175-177° C. $^1$H NMR (C$_5$D$_5$N) δ 11.77 (1H, s, NH), 8.97 (1H, d, J=8.0 Hz, NH), 8.88 (1H, d, J=8.0 Hz, NH), 8.05 (2H, d, J=7.2 Hz), 7.89 (1H, d, J=8.0 Hz), 7.51 (1H, d, J=8.0 Hz), 7.36-7.32 (4H, m), 7.28-7.22 (5H, m), 7.19 (1H, m), 7.09 (1H, t, J=7.6 Hz), 5.58 (1H, dd, J=14.4, 6.8 Hz), 5.50 (1H, br.s, OH), 4.75 (1H, m), 3.91 (2H, m), 3.75 (1H, dd, J=14.4, 6.8 Hz), 3.64 (1H, dd, J=14.4, 6.8 Hz), 3.15 (1H, dd, J=13.4, 7.2 Hz), 3.03 (1H, dd, J=13.4, 7.2 Hz). $^{13}$C NMR (C$_5$D$_5$N) δ 172.7 (s), 167.9 (s), 139.8 (s), 137.7 (s), 135.7 (s), 131.5 (d), 130.2 (d), 129.0 (s), 128.9 (2×C, d), 128.7 (2×C, d), 128.2 (2×C, d), 126.7 (d), 124.6 (d), 121.9 (d), 119.5 (d), 119.4 (d), 112.1 (d), 111.5 (s), 63.2 (t), 55.9 (d), 53.8 (d), 37.7 (t), 29.4 (t). ESI-MS (m/z, %): 464 [M+Na]+ (100), 442 [M+1]+ (5). HR-ESI-MS m/z 464.1947 [M+Na]+ (calcd for $C_{27}H_{27}N_3O_3Na$ 464.1950).

Compound 12b

11% yield. White powder, mp 173-175° C. $^1$H NMR (C$_5$D$_5$N) δ 11.78 (1H, s, NH), 9.07 (1H, d, J=7.6 Hz, NH), 8.87 (1H, d, J=8.0 Hz, NH), 8.09 (2H, d, J=7.6 Hz), 7.85 (1H, d, J=8.0 Hz), 7.52 (1H, br.s), 7.48 (1H, d, J=8.0 Hz), 7.29 (2H, t, J=7.6 Hz), 7.27 (2H, t, J=7.6 Hz), 7.22-7.15 (3H, m), 7.09 (2H, t, J=8.6 Hz), 5.62 (1H, dd, J=14.4, 7.2 Hz), 4.71 (1H, m), 3.87 (2H, m), 3.80 (1H, dd, J=14.4, 7.2 Hz), 3.68 (1H, dd, J=14.4, 7.2 Hz), 3.21 (1H, dd, J=13.6, 6.8 Hz), 3.09 (1H, dd, J=13.6, 6.8 Hz). $^{13}$C NMR (C$_5$D$_5$N) δ 172.5 (s), 167.8 (s), 139.6 (s), 137.5 (s), 135.5 (s), 131.4 (d), 129.9 (2×C, d), 128.7 (s), 128.6 (2×C, d), 128.5 (2×C, d), 128.1 (2×C, d), 126.4 (d), 124.4 (d), 121.7 (d), 119.3 (d), 119.2 (d), 111.9 (d), 111.4 (s), 63.1 (t), 55.5 (d), 53.8 (d), 37.6 (t), 28.8 (t). ESI-MS (m/z, %): 464 [M+Na]+ (100), 442 [M+1]+ (37). HR-ESI-MS m/z 464.1947 [M+Na]+ (calcd for $C_{27}H_{27}N_3O_3Na$ 464.1950).

N—(N-Benzoyl-L-tryptophanyl)-D-phenylalaninol (compounds 13a and 13b)

Compound 13a

53% yield. White powder, mp 151-153° C. $^1$H NMR (C$_5$D$_5$N) δ 11.53 (1H, s, NH), 8.96 (1H, d, J=7.6 Hz, NH), 8.82 (1H, d, J=8.0 Hz, NH), 8.07 (2H, d, J=7.6 Hz), 7.76 (1H, s), 7.46 (1H, d, J=8.4 Hz), 7.34-7.13 (10H, m), 5.95 (1H, br.s, OH), 5.56 (1H, dd, J=14.0, 7.2 Hz), 4.73 (1H, m), 3.91 (1H, dd, J=10.8, 5.2 Hz), 3.85 (1H, dd, J=10.8, 5.2 Hz), 3.70 (1H, dd, J=14.0, 7.2 Hz), 3.60 (1H, dd, J=14.0, 7.2 Hz), 3.11 (1H, dd, J=13.6, 7.2 Hz), 3.00 (1H, dd, J=13.6, 7.2 Hz). $^{13}$C NMR (C$_5$D$_5$N) δ 172.5 (s), 167.6 (s), 152.4 (s), 139.5 (s), 135.5 (s), 132.2 (s), 131.4 (d), 130.1 (2×C, d), 129.8 (s), 128.7 (2×C, d), 128.5 (2×C, d), 128.0 (2×C, d), 125.0 (d), 112.8 (d), 112.5 (d), 110.5 (s), 104.0 (d), 62.8 (t), 55.8 (d), 53.6 (d), 37.5 (t), 29.5 (t). ESI-MS (m/z, %): 480 [M+Na]+ (100), 458 [M+1]+ (18). HR-ESI-MS m/z 480.1897 [M+Na]+ (calcd for $C_{27}H_{27}N_3O_4Na$ 480.1899).

Compound 13b

25% yield. White powder, mp 120-122° C. $^1$H NMR (C$_5$D$_5$N) δ 11.53 (1H, s, NH), 9.05 (1H, d, J=8.0 Hz, NH), 8.76 (1H, d, J=8.0 Hz, NH), 8.10 (2H, d, J=7.6 Hz), 7.71 (1H, s), 7.55 (1H, s), 7.46 (1H, d, J=8.0 Hz), 7.38-7.35 (3H, m), 7.30 (2H, t, J=7.6 Hz), 7.18-7.14 (4H, m), 7.08 (1H, d, J=8.0 Hz), 5.90 (1H, br.s, OH), 5.59 (1H, dd, J=14.2, 7.2 Hz), 4.69 (1H, m), 3.88 (1H, dd, J=10.4, 5.2 Hz), 3.82 (1H, dd, J=10.4, 5.2 Hz), 3.74 (1H, dd, J=14.2, 7.2 Hz), 3.64 (1H, dd, J=14.2, 7.2 Hz), 3.20 (1H, dd, J=13.6, 7.2 Hz), 3.07 (1H, dd, J=13.6, 7.2 Hz). $^{13}$C NMR (C$_5$D$_5$N) δ 172.4 (s), 167.7 (s), 152.3 (s), 139.6 (s), 135.5 (s), 132.2 (s), 131.4 (d), 129.9 (2×C, d), 129.8 (s), 128.6 (2×C, d), 128.5 (2×C, d), 128.1 (2×C, d), 126.4 (d), 125.0 (d), 112.8 (d), 112.5 (d), 110.6 (s), 104.0 (d), 63.8 (t), 55.5 (d), 53.7 (d), 37.6 (t), 28.9 (t). ESI-MS (m/z, %): 480 [M+Na]+ (100), 458 [M+1]+ (82). HR-ESI-MS m/z 480.1897 [M+Na]+ (calcd for $C_{27}H_{27}N_3O_4Na$ 480.1899).

[Embodiment 3] Preparation of N—(N-nicotinoyl-L-tryptophanyl)-D-phenylalanine methyl esters (compounds 15a and 15b)

A mixture solution of L-tryptophan methyl ester (1.0 equiv.) in pyridine and nicotinoyl chlorides (1.1 equiv.) was prepared. The reaction mixture was stirred at room temperature for 16.0 h, and then evaporated and purified by silica gel column chromatography using a mixture of MeOH-CHCl$_3$ (1:20) to afford N-nicotinoyl-L-tryptophan methyl ester. N-Nicotinoyl-L-tryptophan methyl ester was further dissolved in 10 mL of 1.0 M LiOH solution, and then added to the mixture for hydrolysis. Upon completion, the reaction mixture was partitioned for three times with ethyl acetate and saturated sodium bicarbonate aqueous solution. The combined aqueous layer was neutralized with 1.0 N HCl solution, followed by extraction with ethyl acetate for three times. The combined organic layer was dried with anhydrous magnesium sulfate and evaporated to yield N-nicotinoyl-L-tryptophan. D-Phenylalanine methyl ester (1.0 mmole) and N-nicotinoyl-L-tryptophan were dissolved in DCM, and then HBTU (2.0 equiv.) and DIEA (1.5 equiv.) were added. The reaction mixture was stirred for 6 hours at room temperature, concentrated and purified by silica gel column chromatography using ethyl acetate to afford the products (compounds 15a and 15b).

Compound 15a

30% yield. White powder, mp 161-163° C. $^1$H NMR ($C_5D_5N$) δ 8.88 (1H, s), 8.66 (1H, d, J=4.4 Hz), 8.21 (1H, s, NH), 7.98 (1H, d, J=8.0 Hz), 7.72 (1H, d, J=7.6 Hz), 7.35 (1H, d, J=7.6 Hz), 7.31 (1H, dd, J=7.8, 2.0 Hz), 7.23-7.12 (5H, m), 7.08 (1H, d, J=7.6 Hz), 6.85 (1H, d, J=6.8 Hz), 6.35 (1H, d, J=8.0 Hz, NH), 4.95 (1H, ddd, J=14.4, 7.6, 7.6 Hz), 4.79 (1H, dd, J=13.6, 6.0 Hz), 3.63 (3H, s), 3.40 (1H, dd, J=14.4, 7.6 Hz), 3.23 (1H, dd, J=14.4, 7.6 Hz), 2.93 (1H, dd, J=13.6, 6.0 Hz), 2.82 (1H, dd, J=13.6, 6.0 Hz). $^{13}$C NMR ($C_5D_5N$) δ 172.0 (s), 171.4 (s), 165.8 (s), 152.7 (d), 148.6 (d), 136.6 (s), 136.0 (d), 135.6 (s), 129.9 (s), 129.5 (2×C, d), 129.0 (2×C, d), 127.9 (s), 127.6 (d), 123.8 (d), 123.6 (d), 122.8 (d), 120.3 (d), 119.1 (d), 111.8 (d), 110.7 (d), 54.8 (d), 53.7 (d), 52.7 (q), 37.9 (t), 28.8 (t). ESI-MS (m/z, %): 471 [M+1]$^+$ (100). HR-ESI-MS m/z 493.1850 [M+Na]$^+$ (calcd for $C_{27}H_{26}N_4O_4Na$ 493.1852).

Compound 15b

6% yield. White powder, mp 130-132° C. $^1$H NMR ($C_5D_5N$) δ 8.88 (1H, s), 8.69 (1H, d, J=4.0 Hz), 8.25 (1H, s, NH), 7.99 (1H, dd, J=6.0, 2.0 Hz), 7.73 (1H, d, J=8.0 Hz), 7.35-7.31 (2H, m), 7.20 (1H, t, J=8.0 Hz), 7.13-7.06 (6H, m), 6.85 (2H, d, J=6.8 Hz), 6.30 (1H, d, J=7.6 Hz, NH), 4.92 (1H, dd, J=14.6, 7.6 Hz), 4.73 (1H, dd, J=13.6, 6.4 Hz), 3.65 (3H, s), 3.45 (1H, dd, J=14.6, 7.6 Hz), 3.21 (1H, dd, J=14.6, 7.6 Hz), 3.01 (1H, dd, J=13.6, 6.4 Hz), 2.92 (1H, dd, J=13.6, 6.4 Hz). $^{13}$C NMR ($C_5D_5N$) δ 171.8 (s), 171.1 (s), 165.7 (s), 152.8 (d), 148.6 (d), 136.7 (s), 135.9 (d), 135.5 (s), 129.9 (s), 129.5 (2×C, d), 128.9 (2×C, d), 127.8 (s), 127.5 (d), 124.0 (d), 123.8 (d), 122.8 (d), 120.4 (d), 119.2 (d), 111.8 (d), 110.7 (d), 54.5 (d), 53.9 (d), 52.7 (q), 38.2 (t), 28.7 (t). ESI-MS (m/z, %): 471 [M+1]$^+$ (100). HR-ESI-MS m/z 493.1849 [M+Na]$^+$ (calcd for $C_{27}H_{26}N_4O_4Na$ 493.1852).

[Embodiment 4] General procedure for the synthesis of N—(N-benzoyl-L-tryptophanyl)-para-substituted-D-phenylalanine methyl esters (compounds 18a-23a and 18b-23b)

Para-Substituted-D-phenylalanine methyl esters (17a-17o were synthesized through deprotecting corresponding N-Boc-D-phenylalanine derivatives (16a-16f), respectively, in 20% trifluroacetic acid (TFA) solution (TFA-DCM=1:4), and then esterified through refluxing methanol (50 ml)-c-$H_2SO_4$ (1.0 ml) for 2 h. The resulting mixtures were subsequently neutralized by ammonium water, partitioned between ice water (100 ml) and chloroform, and concentrated the organic layers. Subsequently, para-substituted-D-phenylalanine methyl esters (17a-17f, 1.0 equiv.) and N-benzoyl-L-tryptophan (1.0 equiv.), which were synthesized by a procedure similar to that described above, were dissolved in DCM, respectively, and then HBTU (2.0 equiv.) and DIEA (1.5 equiv.) were added. The reaction mixture was stirred for 6 hours at room temperature, concentrated and purified by silica gel column chromatography using a mixture of n-hexane-ethyl acetate (6:4) to afford the products (compounds 18a-24a and 18b-24b).

N—(N-Benzoyl-L-tryptophanyl)-para-nitro-D-phenylalanine methyl esters (compounds 18a and 18b)

Compound 18a

42% yield. White powder, mp 240-242° C. $^1$H NMR ($C_5D_5N$) δ 11.91 (1H, s, NH), 9.76 (1H, d, J=8.0 Hz, NH), 9.24 (1H, d, J=8.0 Hz, NH), 8.09 (2H, d, J=8.0 Hz), 7.98 (2H, d, J=8.0 Hz), 7.90 (1H, d, J=8.0 Hz), 7.56 (1H, d, J=8.0 Hz), 7.45 (1H, s), 7.36 (1H, t, J=8.0 Hz), 7.30-7.24 (3H, m), 7.17-7.14 (3H, m), 5.66 (1H, dd, J=14.2, 7.2 Hz), 5.31 (1H, dd, J=13.8, 7.2 Hz), 3.80 (1H, dd, J=14.2, 7.2 Hz), 3.62 (1H, dd, J=14.2, 7.2 Hz), 3.55 (3H, s), 3.22 (1H, dd, J=13.8, 7.2 Hz), 3.15 (1H, dd, J=13.8, 7.2 Hz). $^{13}$C NMR ($C_5D_5N$) δ 172.8 (s), 171.7 (s), 167.9 (s), 147.1 (s), 145.4 (s), 137.5 (s), 135.4 (s), 131.5 (d), 130.7 (2×C, d), 128.6 (s), 128.6 (2×C, d), 128.1 (2×C, d), 124.5 (d), 123.7 (2×C, d), 121.9 (d), 119.4 (d), 119.3 (d), 112.1 (d), 111.2 (s), 55.5 (d), 53.8 (d), 52.1 (q), 37.5 (t), 28.9 (t). ESI-MS (m/z, %): 537 [M+Na]$^+$ (100). HR-ESI-MS m/z 537.1754 [M+Na]$^+$ (calcd for $C_{28}H_{26}N_4O_6Na$ 537.1750).

Compound 18b

8% yield. White powder, mp 182-184° C. $^1$H NMR ($C_5D_5N$) δ 11.81 (1H, s, NH), 9.72 (1H, d, J=8.0 Hz, NH), 9.29 (1H, d, J=8.0 Hz, NH), 8.10 (2H, d, J=8.0 Hz), 7.97 (2H, d, J=8.0 Hz), 7.74 (1H, d, J=8.0 Hz), 7.49 (1H, d, J=8.0 Hz), 7.44 (1H, s), 7.41-7.37 (3H, m), 7.32 (2H, t, J=7.6 Hz), 7.20 (1H, t, J=8.0 Hz), 7.05 (1H, t, J=8.0 Hz), 5.65 (1H, dd, J=14.8, 7.2 Hz), 5.31 (1H, dd, J=13.6, 8.0 Hz), 3.77 (1H, dd, J=14.8, 7.2 Hz), 3.62 (3H, s), 3.61 (1H, dd, J=14.8, 7.2 Hz), 3.39 (1H, dd, J=13.6, 8.0 Hz), 3.21 (1H, dd, J=13.6, 8.0 Hz). $^{13}$C NMR ($C_5D_5N$) δ 173.0 (s), 171.9 (s), 168.0 (s), 147.1 (s), 145.4 (s), 137.5 (s), 135.4 (s), 131.6 (d), 130.9 (2×C, d), 128.6 (2×C, d), 128.5 (s), 128.1 (2×C, d), 124.4 (d), 123.7 (2×C, d), 121.7 (d), 119.2 (d), 119.1 (d), 111.9 (d), 111.1 (s), 55.3 (d), 53.7 (d), 52.2 (q), 37.8 (t), 28.5 (t). ESI-MS (m/z, %): 537 [M+Na]$^+$ (100). HR-ESI-MS m/z 537.1753 [M+Na]$^+$ (calcd for $C_{28}H_{26}N_4O_6Na$ 537.1750).

N—(N-Benzoyl-L-tryptophanyl)-para-methyl-D-phenylalanine methyl esters (compounds 19a and 19b)

Compound 19a

50% yield. White powder, mp 185-187° C. CD (c 0.18 mM, MeOH) nm (mdeg) 232 (−1.30), 224 (−0.28) nm. $^1$H NMR ($C_5D_5N$) δ 11.82 (1H, s, NH), 9.35 (1H, d, J=8.0 Hz, NH), 9.07 (1H, d, J=8.0 Hz, NH), 8.04 (2H, d, J=8.0 Hz), 7.87 (2H, d, J=8.0 Hz), 7.53 (1H, d, J=7.6 Hz), 7.36-7.34 (2H, m), 7.28-7.20 (3H, m), 7.14 (1H, t, J=7.6 Hz), 7.08 (1H, d, J=7.6 Hz), 6.99 (2H, d, J=7.6 Hz), 5.68 (1H, dd, J=14.4, 6.8 Hz), 5.22 (1H, dd, J=13.8, 7.2 Hz), 3.80 (1H, dd, J=14.4, 6.8 Hz), 3.64 (1H, dd, J=14.4, 6.8 Hz), 3.52 (3H, s), 3.16 (1H, dd, J=13.8, 7.2 Hz), 3.07 (1H, dd, J=13.8, 7.2 Hz), 2.11 (3H, s). $^{13}$C NMR ($C_5D_5N$) δ 172.7 (s), 172.4 (s), 167.8 (s), 137.5 (s), 135.4 (s), 134.3 (s), 131.4 (d), 129.7 (2×C, d), 129.5 (2×C, d), 128.7 (s), 128.5 (2×C, d), 128.0 (2×C, d), 124.4 (d), 121.8 (d), 119.3 (2×C, d), 112.0 (d), 111.2 (s), 55.3 (d), 54.5 (d), 51.9 (q), 37.6 (t), 29.0 (t), 20.9 (q). ESI-MS (m/z, %): 506 [M+Na]+ (100). HR-ESI-MS m/z 506.2059 [M+Na]+ (calcd for $C_{29}H_{29}N_3O_4Na$ 506.2056).

Compound 19b

16% yield. White powder, mp 197-199° C. CD (c 0.18 mM, MeOH) nm (mdeg) 233 (1.75), 221 (−1.81), 213 (−0.42) nm. $^1$H NMR ($C_5D_5N$) δ 11.79 (1H, s, NH), 9.52 (1H, d, J=8.0 Hz, NH), 9.16 (1H, d, J=8.0 Hz, NH), 8.09 (2H, d, J=8.0 Hz), 7.78 (2H, d, J=8.0 Hz), 7.48 (1H, d, J=8.0 Hz), 7.46 (1H, d, J=1.6 Hz), 7.38 (1H, t, J=8.0 Hz), 7.30 (2H, t, J=8.0 Hz), 7.22-7.15 (3H, m), 7.07 (1H, d, J=8.0 Hz), 6.92 (2H, d, J=7.6 Hz), 5.70 (1H, dd, J=14.4, 7.2 Hz), 5.24 (1H, dd, J=13.8, 7.2 Hz), 3.80 (1H, dd, J=14.4, 7.2 Hz), 3.65 (1H, dd, J=14.4, 7.2 Hz), 3.58 (3H, s), 3.27 (1H, dd, J=13.8, 7.2 Hz), 3.14 (1H, dd, J=13.8, 7.2 Hz), 2.04 (3H, s). $^{13}$C NMR ($C_5D_5N$) δ 172.7 (s), 172.5 (s), 167.9 (s), 137.5 (s), 136.2 (s), 135.3 (s), 134.3 (s), 131.4 (d), 129.7 (2×C, d), 129.4 (2×C, d), 128.7 (s), 128.5 (2×C, d), 128.1 (2×C, d), 124.4 (d), 121.7 (d), 119.2 (2×C, d), 111.9 (d), 111.2 (s), 55.1 (d), 54.6 (d), 51.9 (q), 37.8 (t), 28.6 (t), 20.9 (q). ESI-MS (m/z, %): 506 [M+Na]+ (100). HR-ESI-MS m/z 506.2060 [M+Na]+ (calcd for $C_{29}H_{29}N_3O_4Na$ 506.2056).

N—(N-Benzoyl-L-tryptophanyl)-para-fluoro-D-phenylalanine methyl esters (compounds 20a and 20b)

Compound 20a

45% yield. White powder, mp 178-180° C. CD (c 0.12 mM, MeOH) nm (mdeg) 232 (−0.76), 223 (0.68) nm. $^1$H NMR ($C_5D_5N$) δ 11.84 (1H, s, NH), 9.40 (1H, d, J=7.6 Hz, NH), 9.15 (1H, d, J=7.6 Hz, NH), 8.07 (2H, d, J=7.6 Hz), 7.90 (2H, d, J=7.6 Hz), 7.54 (1H, d, J=7.6 Hz), 7.40 (1H, s), 7.35 (1H, t, J=7.2 Hz), 7.29-7.25 (3H, m), 7.25-7.20 (3H, m), 7.15 (1H, t, J=7.6 Hz), 7.08 (1H, d, J=6.4 Hz), 6.89 (2H, t, J=8.0 Hz), 5.68 (1H, dd, J=14.2, 6.8 Hz), 5.19 (1H, dd, J=13.6, 6.8 Hz), 3.79 (1H, dd, J=14.2, 6.8 Hz), 3.65 (1H, dd, J=14.2, 6.8 Hz), 3.58 (3H, s), 3.27 (1H, dd, J=13.8, 6.8 Hz), 3.13 (1H, dd, J=13.6, 6.8 Hz). $^{13}$C NMR ($C_5D_5N$) δ 172.7 (s), 172.1 (s), 167.9 (s), 162.1 (s, $J_{C-F}$=242.2 Hz), 137.5 (s), 135.4 (s), 133.4 (s, $J_{C-F}$=3.0 Hz), 131.4 (d), 128.7 (s), 128.5 (2×C, d), 128.1 (2×C, d), 124.4 (d), 121.9 (d), 119.3 (2×C, d), 115.4 (2×C, d, $J_{C-F}$=21.4 Hz), 112.0 (d), 111.2 (s), 55.4 (d), 54.4 (d), 51.9 (q), 37.1 (t), 29.0 (t). ESI-MS (m/z, %): 510 [M+Na]+ (100). HR-ESI-MS m/z 510.1808 [M+Na]+ (calcd for $C_{28}H_{26}FN_3O_4Na$ 510.1805).

Compound 20b

14% yield. White powder, mp 184-186° C. CD (c 0.12 mM, MeOH) nm (mdeg) 233 (0.69), 221 (−0.55) nm. $^1$H NMR ($C_5D_5N$) δ 11.80 (1H, s, NH), 9.60 (1H, d, J=8.0 Hz, NH), 9.22 (1H, d, J=8.0 Hz, NH), 8.11 (2H, d, J=7.6 Hz), 7.77 (2H, d, J=7.6 Hz), 7.49 (1H, d, J=7.6 Hz), 7.46 (1H, s), 7.37 (1H, t, J=7.6 Hz), 7.30 (1H, t, J=7.6 Hz), 7.25-7.20 (3H, m), 7.06 (1H, t, J=7.6 Hz), 6.89 (2H, t, J=8.0 Hz), 5.68 (1H, dd, J=14.6, 7.2 Hz), 5.22 (1H, dd, J=13.8, 7.2 Hz), 3.79 (1H, dd, J=14.6, 7.2 Hz), 3.64 (1H, dd, J=14.6, 7.2 Hz), 3.58 (3H, s), 3.27 (1H, dd, J=13.8, 7.2 Hz), 3.13 (1H, dd, J=13.8, 7.2 Hz). $^{13}$C NMR ($C_5D_5N$) δ 172.8 (s), 172.3 (s), 167.9 (s), 162.1 (s, $J_{C-F}$=242.0 Hz), 137.5 (s), 135.5 (s), 133.4 (s, $J_{C-F}$=3.2 Hz), 131.6 (d, JC-F=8.0 Hz), 131.5 (d), 128.6 (s), 128.5 (2×C, d), 128.1 (2×C, d), 124.4 (d), 121.7 (d), 119.2 (d), 119.1 (d), 115.4 (2×C, d, $J_{C-F}$=21.0 Hz), 111.9 (d), 111.2 (s), 55.2 (d), 54.4 (d), 52.0 (q), 37.3 (t), 28.6 (t). ESI-MS (m/z, %): 510 [M+Na]+ (100). HR-ESI-MS m/z 510.1809 [M+Na]+ (calcd for $C_{28}H_{26}FN_3O_4Na$ 510.1805).

N—(N-Benzoyl-L-tryptophanyl)-para-chloro-D-phenylalanine methyl esters (compounds 21a and 21b)

Compound 21a

37% yield. White powder, mp 190-191° C. $^1$H NMR ($C_5D_5N$) δ 11.86 (1H, s, NH), 9.42 (1H, d, J=8.0 Hz, NH), 9.16 (1H, d, J=8.0 Hz, NH), 8.07 (2H, d, J=8.0 Hz), 7.90 (1H, d, J=8.0 Hz), 7.54 (1H, d, J=7.6 Hz), 7.40 (1H, d, J=1.6 Hz), 7.35 (1H, t, J=7.2 Hz), 7.29-7.23 (3H, m), 7.19-7.14 (3H, m), 7.02 (2H, d, J=8.0 Hz), 5.68 (1H, dd, J=14.2, 7.2 Hz), 5.18 (1H, dd, J=14.0, 7.2 Hz), 3.79 (1H, dd, J=14.2, 7.2 Hz), 3.64 (1H, dd, J=14.2, 7.2 Hz), 3.51 (3H, s), 3.11 (1H, dd, J=14.0, 7.2 Hz), 3.03 (1H, dd, J=14.0, 7.2 Hz). $^{13}$C NMR ($C_5D_5N$) δ 172.7 (s), 172.0 (s), 167.9 (s), 137.5 (s), 136.2 (s), 135.5 (s), 132.6 (s), 131.5 (2×C, d), 131.4 (2×C, d), 128.8 (2×C, d), 128.7 (s), 128.5 (2×C, d), 128.1 (2×C, d), 124.4 (d), 121.9 (d), 119.3 (2×C, d), 112.0 (d), 111.2 (s), 55.4 (d), 54.2 (d), 51.9 (q), 37.2 (t), 29.0 (t). ESI-MS (m/z, %): 526 [M+Na]+ (100). HR-ESI-MS m/z 526.1506 [M+Na]+ (calcd for $C_{28}H_{26}ClN_3O_4Na$ 526.1509).

Compound 21b

9% yield. White powder, mp 174-176° C. $^1$H NMR ($C_5D_5N$) δ 11.80 (1H, s, NH), 9.62 (1H, d, J=8.0 Hz, NH), 9.23 (1H, d, J=8.0 Hz, NH), 8.11 (2H, d, J=8.0 Hz), 7.77 (1H, d, J=8.0 Hz), 7.49 (1H, d, J=8.0 Hz), 7.46 (1H, br.s), 7.38 (1H, t, J=8.0 Hz), 7.31 (2H, t, J=8.0 Hz), 7.22-7.19 (3H, m), 7.14 (2H, t, J=8.0 Hz), 7.06 (1H, d, J=8.0 Hz), 5.68 (1H, dd, J=14.6, 7.2 Hz), 5.22 (1H, dd, J=13.8, 7.6 Hz), 3.79 (1H, dd, J=14.6, 7.2 Hz), 3.64 (1H, dd, J=14.6, 7.2 Hz), 3.58 (3H, s), 3.26 (1H, dd, J=13.8, 7.6 Hz), 3.12 (1H, dd, J=13.8, 7.6 Hz). $^{13}$C NMR ($C_5D_5N$) δ 172.8 (s), 172.2 (s), 168.0 (s), 137.5 (s), 136.3 (s), 135.5 (s), 132.5 (s), 131.5 (d), 131.4 (2×C, d), 128.7 (s), 128.7 (2×C, d), 128.6 (2×C, d), 124.4 (d), 121.7 (d), 119.2 (d), 119.1 (d), 111.9 (d), 111.2 (s), 55.2 (d), 54.2 (d), 52.0 (q), 37.4 (t), 28.6 (t). ESI-MS (m/z, %): 526 [M+Na]+ (100). HR-ESI-MS m/z 526.1511 [M+Na]+ (calcd for $C_{28}H_{26}ClN_3O_4Na$ 526.1509).

N—(N-Benzoyl-L-tryptophanyl)-para-bromo-D-phenylalanine methyl esters (compounds 22a and 22b)

Compound 22a

23% yield. White powder, mp 190-191° C. CD (c 0.15 mM, MeOH) nm (mdeg) 232 (−0.41), 223 (0.15) nm. $^1$H NMR ($C_5D_5N$) δ 11.85 (1H, s, NH), 9.40 (1H, d, J=8.0 Hz, NH), 9.12 (1H, d, J=8.0 Hz, NH), 8.07 (2H, d, J=7.2 Hz), 7.90 (1H, d, J=7.6 Hz), 7.54 (1H, d, J=7.6 Hz), 7.41 (1H, br.s), 7.38-7.32 (3H, m), 7.28 (1H, t, J=7.2 Hz), 7.24 (1H, t, J=7.6 Hz), 7.15 (1H, t, J=8.0 Hz), 6.97 (2H, d, J=8.0 Hz), 5.67 (1H, dd, J=14.4, 7.2 Hz), 5.17 (1H, dd, J=13.8, 7.2 Hz), 3.79 (1H, dd, J=14.4, 7.2 Hz), 3.64 (1H, dd, J=14.4, 7.2 Hz), 3.51 (3H, s), 3.09 (1H, dd, J=13.8, 7.2 Hz), 3.02 (1H, dd, J=13.8, 7.2 Hz). $^{13}$C NMR ($C_5D_5N$) δ 172.7 (s), 172.0 (s), 167.8 (s), 137.5 (s), 136.7 (s), 135.4 (s), 131.8 (2×C, d), 131.7 (2×C, d), 131.5 (d), 128.7 (s), 128.5 (2×C, d), 128.1 (2×C, d), 124.4 (d), 121.9 (d), 120.9 (s), 119.3 (2×C, d), 112.0 (d), 111.2 (s), 55.4 (d), 54.1 (d), 51.9 (q), 37.2 (t), 29.0 (t). ESI-MS (m/z, %): 570 [M+Na]$^+$ (100), 572 [M+2+Na]$^+$ (100). HR-ESI-MS m/z 570.1008 [M+Na]$^+$ (calcd for $C_{28}H_{26}BrN_3O_4Na$ 570.1004).

Compound 22b

8% yield. White powder, mp 174-176° C. CD (c 0.18 mM, MeOH) nm (mdeg) 241 (0.49), 232 (0.24), 220 (−0.75), 214 (−0.28) nm. $^1$H NMR ($C_5D_5N$) δ 11.81 (1H, s, NH), 9.62 (1H, d, J=8.0 Hz, NH), 9.23 (1H, d, J=8.0 Hz, NH), 8.11 (2H, d, J=8.0 Hz), 7.76 (1H, d, J=7.6 Hz), 7.49 (1H, d, J=7.6 Hz), 7.45 (1H, d, J=1.6 Hz), 7.39 (1H, t, J=7.6 Hz), 7.32 (2H, t, J=7.6 Hz), 7.29 (2H, d, J=7.2 Hz), 7.20 (1H, t, J=7.6 Hz), 7.14 (2H, d, J=8.4 Hz), 7.06 (1H, t, J=7.6 Hz), 5.68 (1H, dd, J=14.6, 7.2 Hz), 5.21 (1H, dd, J=13.6, 7.6 Hz), 3.79 (1H, dd, J=14.6, 7.2 Hz), 3.64 (1H, dd, J=14.6, 7.2 Hz), 3.58 (3H, s), 3.24 (1H, dd, J=13.6, 7.6 Hz), 3.10 (1H, dd, J=13.6, 7.6 Hz). $^{13}$C NMR ($C_5D_5N$) δ 172.8 (s), 172.1 (s), 168.0 (s), 137.5 (s), 136.8 (s), 135.5 (s), 131.8 (2×C, d), 131.7 (2×C, d), 131.5 (d), 128.6 (s), 128.6 (s), 128.6 (2×C, d), 128.1 (2×C, d), 124.4 (d), 121.7 (d), 120.9 (s), 119.2 (d), 119.1 (d), 111.9 (d), 111.2 (s), 55.2 (d), 54.2 (d), 52.0 (q), 37.4 (t), 28.6 (t). ESI-MS (m/z, %): 570 [M+Na]$^+$ (100), 572 [M+2+Na]$^+$ (100). HR-ESI-MS m/z 570.1007 [M+Na]$^+$ (calcd for $C_{28}H_{26}BrN_3O_4Na$ 570.1004).

N—(N-Benzoyl-L-tryptophanyl)-para-trifluoromethyl-D-phenylalanine methyl esters (compounds 23a and 23b)

Compound 23a

26% yield. White powder, mp 233-235° C. $^1$H NMR ($C_5D_5N$) δ 11.88 (1H, s, NH), 9.50 (1H, d, J=8.0 Hz, NH), 9.18 (1H, d, J=8.0 Hz, NH), 8.08 (2H, d, J=7.6 Hz), 7.89 (1H, d, J=7.6 Hz), 7.54 (1H, d, J=7.6 Hz), 7.45 (2H, d, J=8.0 Hz), 7.42 (1H, d, J=2.0 Hz), 7.36 (1H, t, J=7.6 Hz), 7.29-7.23 (3H, m), 7.19 (2H, d, J=8.0 Hz), 7.15 (1H, t, J=7.6 Hz), 5.67 (1H, dd, J=14.4, 7.2 Hz), 5.23 (1H, dd, J=14.0, 7.2 Hz), 3.79 (1H, dd, J=14.4, 7.2 Hz), 3.63 (1H, dd, J=14.4, 7.2 Hz), 3.52 (3H, s), 3.20 (1H, dd, J=14.0, 7.2 Hz), 3.14 (1H, dd, J=14.0, 7.2 Hz). $^{13}$C NMR ($C_5D_5N$) δ 172.8 (s), 171.9 (s), 167.6 (s), 142.1 (s), 137.5 (s), 135.4 (s), 131.5 (d), 130.4 (2×C, d), 128.7 (2×C, d), 128.6 (s, $J_{C-F}$=32.2 Hz), 128.1 (2×C, d), 125.5 (2×C, d, $J_{C-F}$=4.0 Hz), 125.0 (s, $J_{C-F}$=270.1 Hz), 124.4 (d), 121.9 (d), 119.3 (2×C, d), 112.0 (d), 111.3 (s), 55.4 (d), 54.0 (d), 52.0 (q), 37.5 (t), 29.0 (t). ESI-MS (m/z, %): 560 [M+Na]$^+$ (100). HR-ESI-MS m/z 560.1776 [M+Na]$^+$ (calcd for $C_{29}H_{26}F_3N_3O_4Na$ 560.1773).

Compound 23b

9% yield. White powder, mp 187-189° C. $^1$H NMR ($C_5D_5N$) δ 11.81 (1H, s, NH), 9.72 (1H, d, J=8.0 Hz, NH), 9.25 (1H, d, J=8.0 Hz, NH), 8.12 (2H, d, J=8.0 Hz), 7.75 (1H, d, J=8.0 Hz), 7.49 (1H, d, J=8.0 Hz), 7.44 (1H, d, J=2.0 Hz), 7.43 (2H, d, J=8.0 Hz), 7.40-7.37 (3H, m), 7.31 (2H, d, J=8.0 Hz), 7.20 (1H, t, J=8.0 Hz), 7.05 (1H, t, J=8.0 Hz), 5.67 (1H, dd, J=14.4, 7.2 Hz), 5.25 (1H, dd, J=14.0, 7.2 Hz), 3.78 (1H, dd, J=14.4, 7.2 Hz), 3.62 (1H, dd, J=14.4, 7.2 Hz), 3.60 (3H, s), 3.36 (1H, dd, J=13.6, 8.0 Hz), 3.21 (1H, dd, J=13.6, 8.0 Hz). $^{13}$C NMR ($C_5D_5N$) δ 172.9 (s), 172.0 (s), 168.0 (s), 142.2 (s), 137.5 (s), 135.4 (s), 131.5 (d), 130.5 (2×C, d), 128.6 (2×C, d), 128.5 (s, $J_{C-F}$=32.0 Hz), 128.1 (2×C, d), 125.5 (2×C, d, $J_{C-F}$=4.0 Hz), 124.9 (s, $J_{C-F}$=270.0 Hz), 124.4 (d), 121.9 (d), 119.2 (d), 119.1 (d), 111.9 (d), 111.1 (s), 55.4 (d), 54.0 (d), 52.0 (q), 37.5 (t), 29.0 (t). ESI-MS (m/z, %): 560 [M+Na]$^+$ (100). HR-ESI-MS m/z 560.1775 [M+Na]$^+$ (calcd for $C_{29}H_{26}F_3N_3O_4Na$ 560.1773).

Preparation of N—(N-benzoyl-L-tryptophanyl)-3-cyclohexyl-D-alanine methyl esters (compounds 24a and 24b)

Compounds 24a and 24b were synthesized in 39% and 14%, respectively, yield from 3-cyclohexyl-D-alanine (16 g) by a similar procedure as described above.

Compound 24a

White powder, mp 170-172° C. $^1$H NMR ($C_5D_5N$) δ 11.88 (1H, s, NH), 9.45 (1H, d, J=8.0 Hz, NH), 9.07 (1H, d, J=8.0 Hz, NH), 8.08 (2H, d, J=8.4 Hz), 7.94 (1H, d, J=7.6 Hz), 7.56 (1H, d, J=7.6 Hz), 7.50 (1H, br.s), 7.35 (1H, dt, J=7.6, 1.2 Hz), 7.29-7.23 (3H, m), 7.14 (1H, t, J=7.6 Hz), 5.72 (1H, dd, J=14.2, 7.2 Hz), 5.00 (1H, m), 3.86 (1H, dd, J=14.2, 7.2 Hz), 3.72 (1H, dd, J=14.2, 7.2 Hz), 3.58 (3H, s), 1.77 (1H, m), 1.66 (2H, m), 1.59-1.48 (4H, m), 1.38 (1H, m), 1.25-0.96 (3H, m), 0.84-0.71 (2H, m). $^{13}$C NMR ($C_5D_5N$) δ 173.7 (s), 172.9 (s), 167.7 (s), 137.5 (s), 135.5 (s), 131.4 (s), 128.7 (s), 128.5 (2×C, d), 128.0 (2×C, d), 124.3 (d), 121.8 (d), 119.3 (d), 119.2 (d), 112.0 (d), 111.2 (d), 55.4 (d), 51.9 (q), 50.9 (d), 39.4 (t), 34.1 (d), 33.6 (t), 32.4 (t), 29.2 (t), 26.6 (t), 26.3 (t), 26.1 (t). ESI-MS (m/z, %): 498 [M+Na]$^+$ (100). HR-ESI-MS m/z 498.2366 [M+Na]$^+$ (calcd for $C_{28}H_{33}N_3O_4Na$ 498.2369).

Compound 24b

White powder, mp 109-111° C. $^1$H NMR ($C_5D_5N$) δ 11.82 (1H, s, NH), 9.67 (1H, d, J=8.0 Hz, NH), 9.27 (1H, d, J=8.0 Hz, NH), 8.12 (2H, d, J=8.0 Hz), 7.78 (1H, d, J=7.6 Hz), 7.55 (1H, br.s), 7.49 (1H, d, J=7.6 Hz), 7.35 (1H, dt, J=1.2, 8.0 Hz), 7.28 (2H, dt, J=1.2, 8.0 Hz), 7.20 (1H, t, J=7.6 Hz), 7.06 (1H, t, J=7.6 Hz), 5.71 (1H, dd, J=14.6, 7.6 Hz), 5.12 (1H, dd, J=14.6, 7.6 Hz), 3.86 (1H, dd, J=14.6, 7.2 Hz), 3.71 (1H, dd, J=14.6, 7.2 Hz), 3.65 (3H, s), 1.73 (2H, m), 1.63 (1H, m), 1.54-1.41 (5H, m), 1.13-0.92 (3H, m), 0.85-0.70 (2H, m). $^{13}$C NMR ($C_5D_5N$) δ 173.9 (s), 173.0 (s), 167.8 (s), 137.5 (s), 135.5 (s), 131.4 (s), 128.7 (s), 128.5 (2×C, d), 128.1 (2×C, d), 124.4 (d), 121.7 (d), 119.2 (2×C, d), 111.9 (d), 111.2 (d), 55.3 (d), 52.0 (q), 50.8 (d), 39.7 (t), 34.2 (d), 33.7 (t), 32.3 (t), 28.6 (t), 26.6 (t), 26.3 (t), 26.1 (t). ESI-MS (m/z, %): 498 [M+Na]$^+$ (100). HR-ESI-MS m/z 498.2367 [M+Na]$^+$ (calcd for $C_{28}H_{33}N_3O_4Na$ 498.2369).

Preparation of N—(N-benzoyl-L-tryptophanyl)-D-phenylalanine-glycine-nitriles (compounds 27a and 27b)

To a mixture solution of Boc-phenylalanine (1.0 equiv.) and aminoacetonitrile (1.0 equiv.) in DCM was added HBTU (2.0 equiv.) and DIEA (1.5 equiv.). The reaction mixture was stirred at room temperature for 6.0 h, and then deprotected and purified by silica gel column chromatography using a mixture of MeOH-CHCl3 (1:10) to afford D-phenylalanine-glycine-nitrile (26). Compound 26 (1.0 equiv.) and N-benzoyl-L-tryptophan (1.0 equiv.) were dissolved in DCM, and then HBTU (2.0 equiv.) and DIEA (1.5 equiv.) were added. The reaction mixture was stirred for 6 hours at room temperature, concentrated and purified by silica gel column chromatography using ethyl acetate-n-hexane (1:1) to afford the mixture of 27a and 27b. The mixture was further purified by HPLC (mobile phase: 65% MeOH+0.03% TFA) to afford products.

Compound 27a

49% yield. White powder, mp 167-169° C. $^1$H NMR ($C_5D_5N$) δ 11.81 (1H, s, NH), 9.73 (1H, t, J=5.6 Hz, NH), 9.63 (1H, d, J=8.4 Hz, NH), 8.39 (1H, d, J=6.4 Hz, NH), 8.07 (2H, d, J=7.6 Hz), 7.77 (1H, d, J=8.0 Hz), 7.56 (1H, d, J=8.0 Hz), 7.35 (1H, t, J=7.6 Hz), 7.29-7.23 (5H, m), 7.20-7.18 (3H, m), 7.15-7.09 (2H, m), 5.35-5.29 (2H, m), 5.00 (1H, m), 4.47 (2H, d, J=5.6 Hz), 3.70 (1H, dd, J=14.2, 7.6 Hz), 3.61 (1H, dd, J=14.2, 7.6 Hz), 3.33 (1H, dd, J=13.6, 8.0 Hz), 3.09 (1H, dd, J=13.6, 8.0 Hz). $^{13}$C NMR ($C_5D_5N$) δ 173.2 (s), 172.7 (s), 166.8 (s), 138.1 (s), 137.5 (s), 135.5 (s), 131.7 (s), 129.7 (2×C, d), 128.8 (2×C, d), 128.5 (s), 128.5 (2×C, d), 128.2 (2×C, d), 126.9 (d), 124.5 (d), 121.9 (d), 119.3 (d), 119.1 (d), 117.6 (s), 112.0 (s), 110.9 (s), 56.6 (d), 55.0 (d), 37.8 (t), 28.4 (t), 28.0 (t). ESI-MS (m/z, %): 516 [M+Na]$^+$ (100). HR-ESI-MS m/z 516.2008 [M+Na]$^+$ (calcd for $C_{29}H_{27}N_5O_3Na$ 516.2011).

Compound 27b

7% yield. White powder, mp 195-197° C. $^1$H NMR ($C_5D_5N$) δ 11.80 (1H, s, NH), 9.76 (1H, d, J=8.0 Hz, NH), 9.63 (1H, t, J=5.2 Hz, NH), 9.10 (1H, d, J=7.6 Hz, NH), 8.07 (2H, d, J=8.0 Hz), 7.74 (1H, d, J=8.0 Hz), 7.49 (1H, d, J=8.0 Hz), 7.44 (1H, br.s), 7.37 (1H, t, J=7.2 Hz), 7.31-7.25 (4H, m), 7.18-7.14 (3H, m), 7.10-7.04 (2H, m), 5.59 (1H, dd, J=14.2, 7.2 Hz), 5.18 (1H, dd, J=14.2, 7.2 Hz), 4.43 (1H, dd, J=17.2, 5.6 Hz), 4.32 (1H, dd, J=17.2, 5.6 Hz), 3.74 (1H, dd, J=14.2, 7.6 Hz), 3.62 (1H, dd, J=14.2, 7.6 Hz), 3.41 (1H, dd, J=13.6, 8.0 Hz), 3.18 (1H, dd, J=13.6, 8.0 Hz). $^{13}$C NMR ($C_5D_5N$) δ 172.7 (s), 172.5 (s), 168.0 (s), 137.9 (s), 137.4 (s), 135.5 (s), 131.5 (s), 129.8 (2×C, d), 128.8 (2×C, d), 128.6 (s), 128.5 (2×C, d), 128.1 (2×C, d), 126.9 (d), 124.5 (d), 121.7 (d), 119.2 (d), 119.1 (d), 117.5 (s), 112.0 (s), 111.0 (s), 55.4 (d), 55.3 (d), 38.4 (t), 28.5 (t), 27.8 (t). ESI-MS (m/z, %): 516 [M+Na]$^+$ (100). HR-ESI-MS m/z 516.2008 [M+Na]$^+$ (calcd for $C_{29}H_{27}N_5O_3Na$ 516.2011).

Embodiments 6-12 are applications of various activity tests for each dipeptide derivative, such as the evaluation of the inhibition of elastase release and superoxide anion generation induced by specific activators of FPR1, fMLP and specific activators of FPR2, formyl peptide receptor-like 1 agonist (WKYMVm), as well as other related studies on the pharmacological mechanism. The methods and procedures for activity tests and the results are as follows.

[Embodiment 6] Cytotoxic Test

Figure 1B:
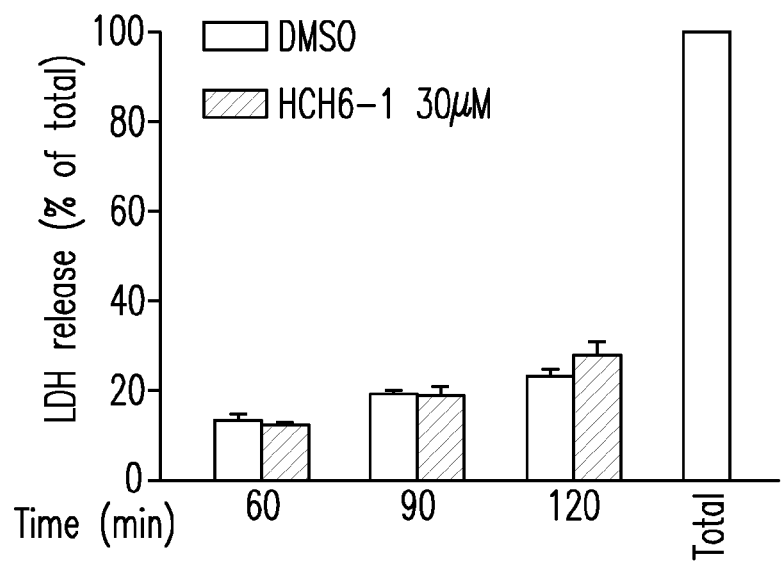

FIGS. 1(a)-1(b) show the influences of HCH6-1 on releasing lactate dehydrogenase (LDH) from human neutrophils under the following experimental conditions. The suspension of neutrophils was reacted with different concentrations of candidate compounds for 15 min, or fixed concentrations of candidate compounds for various times. Also, 0.1% Triton X-100 was added to react for 30 min as a release amount of total lactate dehydrogenase (Total LDH), wherein the supernatant was subjected to centrifugation for 8 min, at 200 g and at 4° C., and then a lactate dehydrogenase reagent was added and kept in the dark and at room temperature for 30 min, and an absorbance at 492 nm was monitored. Results are measured based on Total LDH as 100%.

FIG. 1(a) shows that HCH6-1's inhibitory effects on fMLP-induced superoxide anion generation and elastase release of neutrophils were not the results of toxicity to the neutrophils.

FIG. 1(b) shows that there was no significant toxicity for HCH6-1 (30 µM) treatment of the cells during a long period, such as 120 min, so as to demonstrate that high concentrations of HCH6-1 reacting with the cells for 120 min was non-toxic for the cells.

[Embodiment 7] Evaluation of Inhibitory Effects on fMLP-Induced Superoxide Anion Generation and Elastase Release of Human Neutrophils Preparation of Human Neutrophils Blood was taken from healthy human donors (20-32 years old) by venipuncture, following a protocol approved by the Institutional Review Board at Chang Gung Memorial Hospital. Neutrophils were isolated by a standard method of dextran sedimentation prior to centrifugation in a Ficoll Hypaque gradient and the hypotonic lysis of erythrocytes. Purified neutrophils that contained >98% viable cells, as determined by the trypan blue exclusion method, were resuspended in $Ca^{2+}$-free HBSS buffer at pH 7.4 and maintained at 4° C. before use.

Measurement of $O_2.^-$ Generation

The evaluation of $O_2.^-$ generation was based on the SOD-inhibitable reduction of ferricytochrome c. In brief, after supplementation with 0.5 mg ml$^{-1}$ ferricytochrome c and 1 mM $Ca^{2+}$, neutrophils were equilibrated at 37° C. for 2 min and incubated with drugs for min. Cells were activated with formyl-L-methionyl-L-leucyl-L-phenylalanine (FMLP, 30 nM) or Trp-Lys-Tyr-Met-Val-DMet (WKYMVm, 1.5 nM) for 10 min in the pre-process of cytochalasin B (CB, 1 µg ml$^{-1}$) for 3 min. Changes in absorbance with the reduction of ferricytochrome c at 550 nm were continuously monitored in a double-beam, six-cell positioner spectrophotometer with constant stirring (Hitachi U-3010, Tokyo, Japan). Calculations were based on the differences in the reactions with and without SOD (100 U ml$^{-1}$) divided by the extinction coefficient for the reduction of ferricytochrome c (c=21.1 mM$^{-1}$/10 mm).

[Embodiment 8] Measurement of Elastase Release

The degranulation of azurophilic granules was determined by elastase release as described above. Experiments were performed using MeO-Suc-Ala-Ala-Pro-Val-p-nitroanilide as the elastase substrate. Briefly, after supplementation with MeO-Suc-Ala-Ala-Pro-Val-p-nitroanilide (100 neutrophils (6×10$^5$ ml$^{-1}$) were equilibrated at 37° C. for 2 min and incubated with drugs for 5 min. Cells were activated by 30 nM fMLF or 1.5 nM WKYMVm for 10 min in the pre-process of 0.5 µg ml$^{-1}$ CB for 3 min, and changes in absorbance at 405 nm were continuously monitored to assay the elastase release. The results are expressed as the percentage of elastase release in the drug-free control group.

[Embodiment 9] Expression of CD11b on the Cell's Surface

Figure 2A:
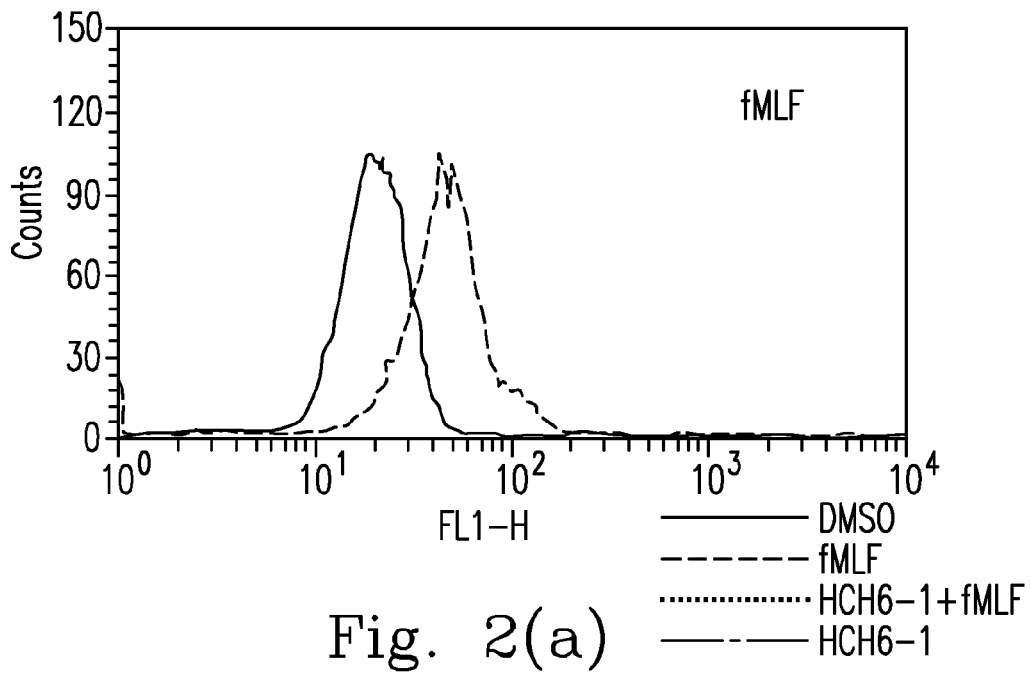
FIGS. 2(a)-2(u) show selective inhibition of HCH6-1 for fMLF-induced CD11b expression in human neutrophils.
Figure 2B:
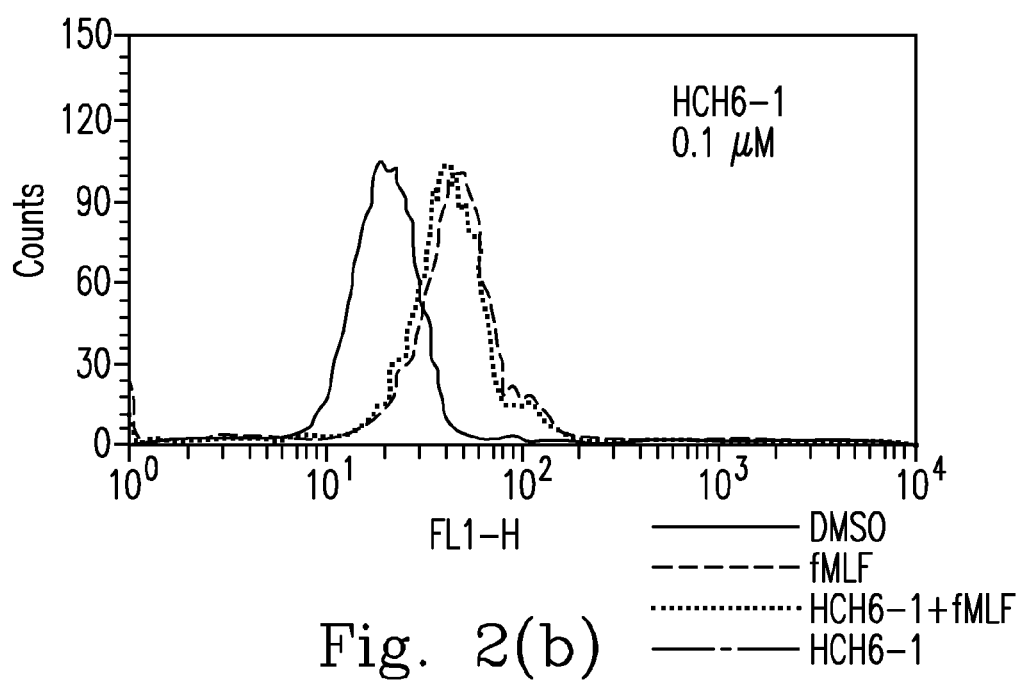
Figure 2C:
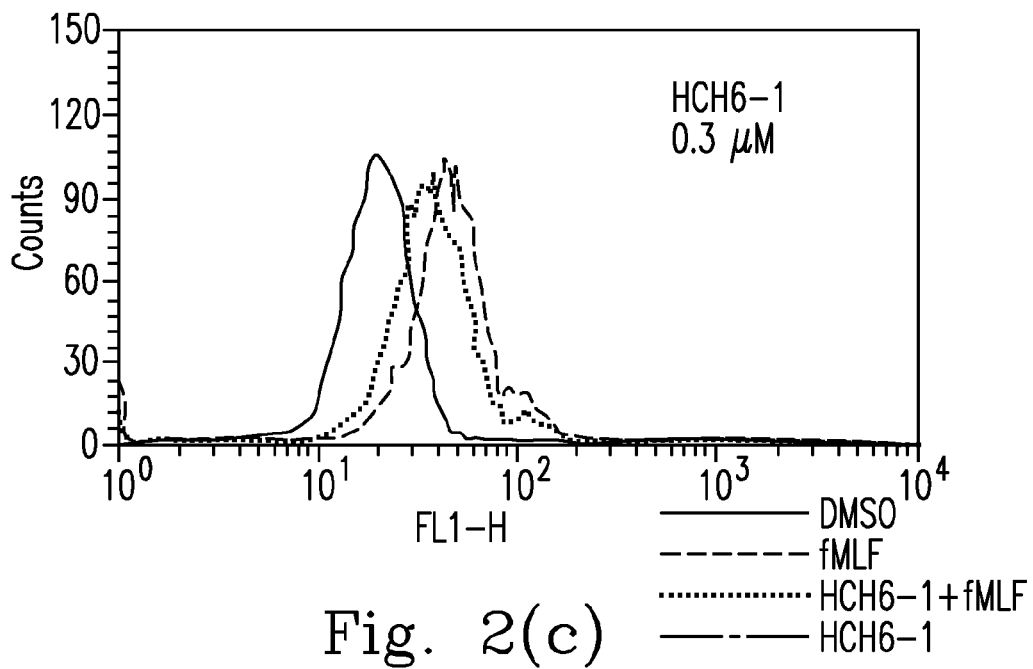
Figure 2D:
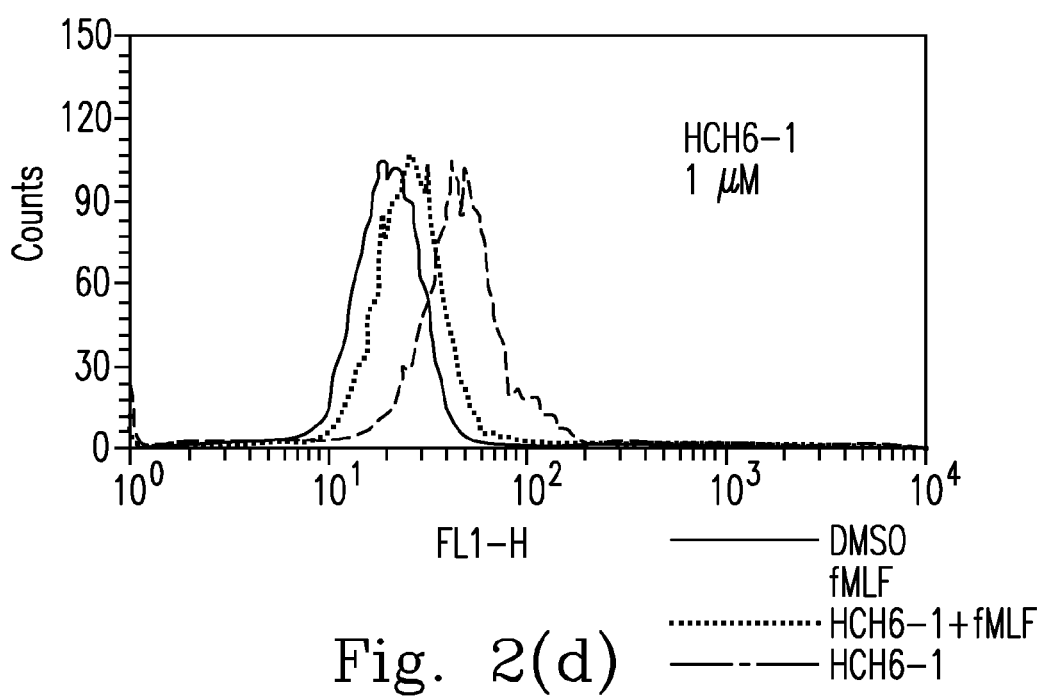
Figure 2E:
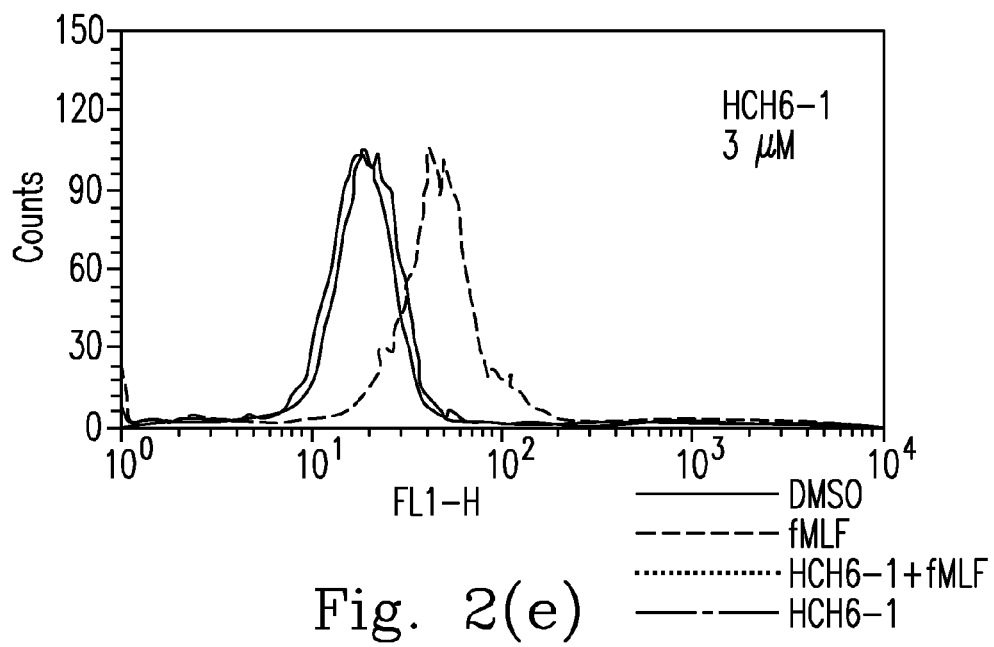
Figure 2F:
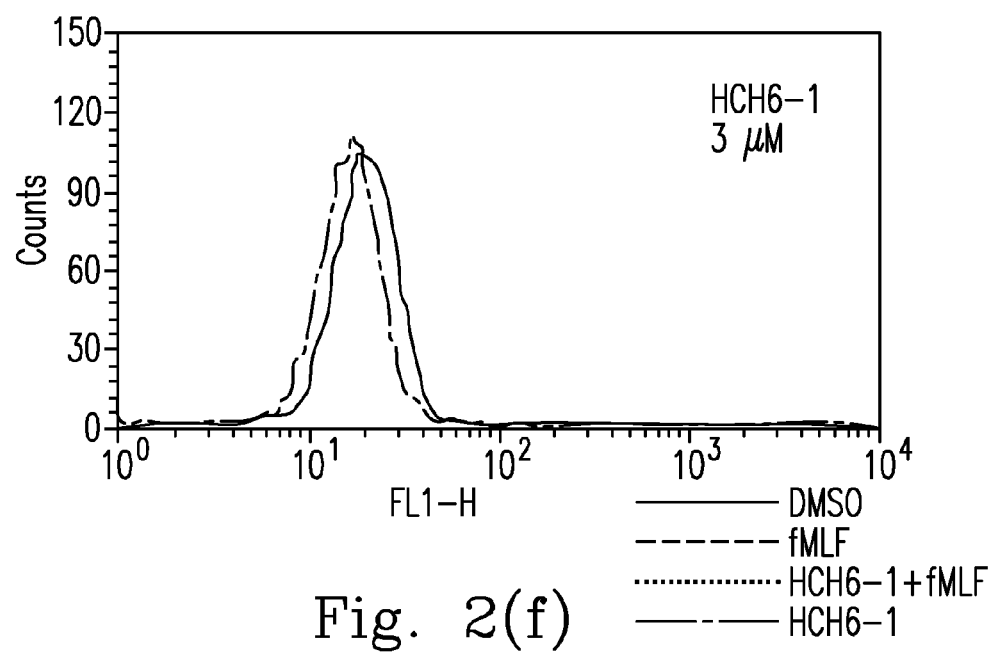
Figure 2G:
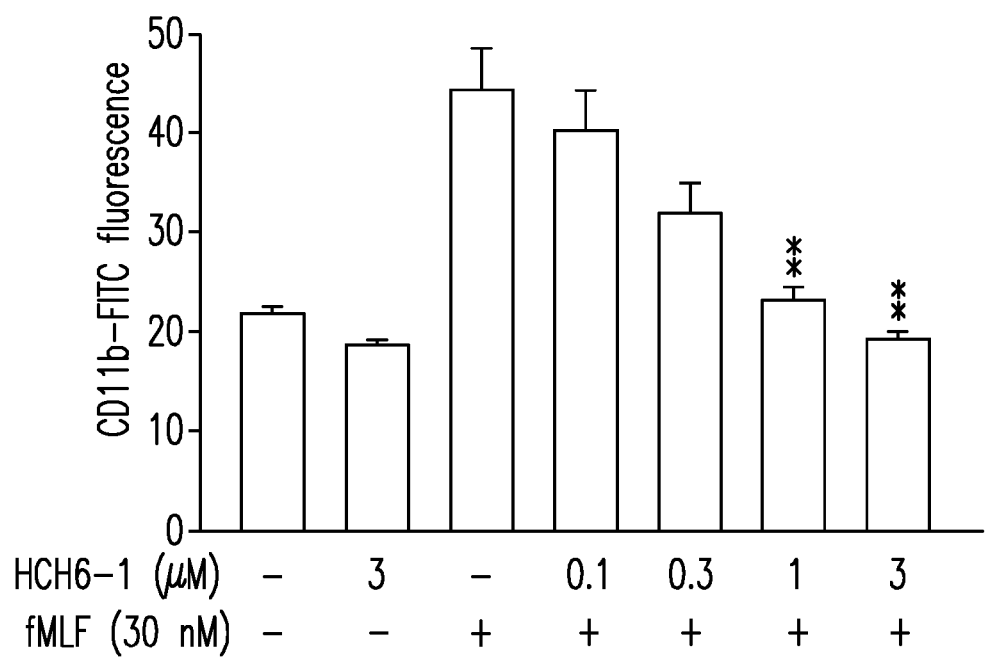
Figure 2H:
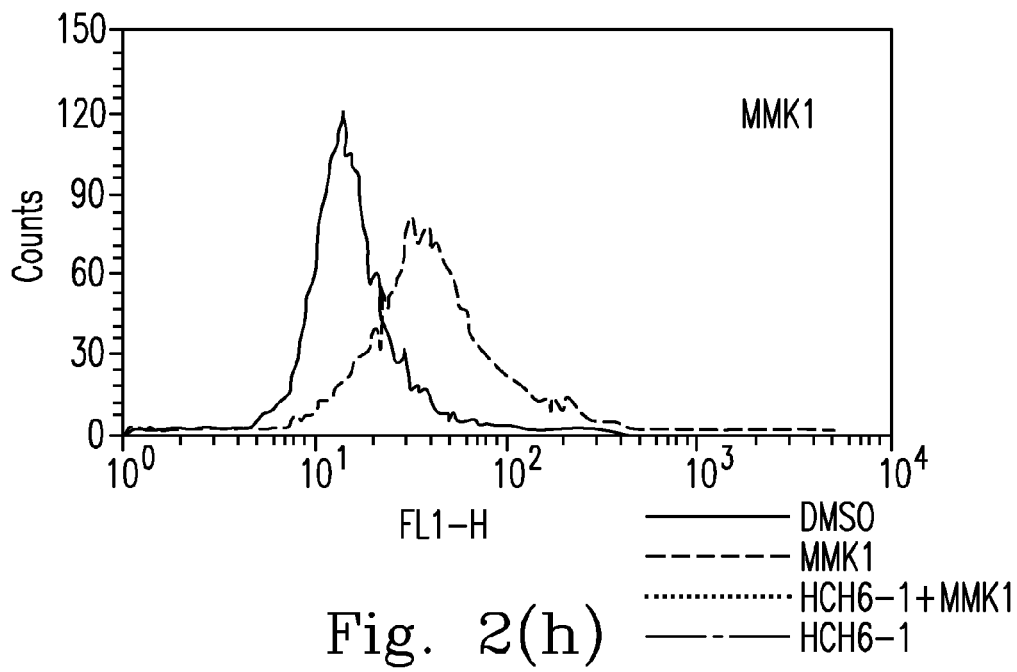
Figure 2I:
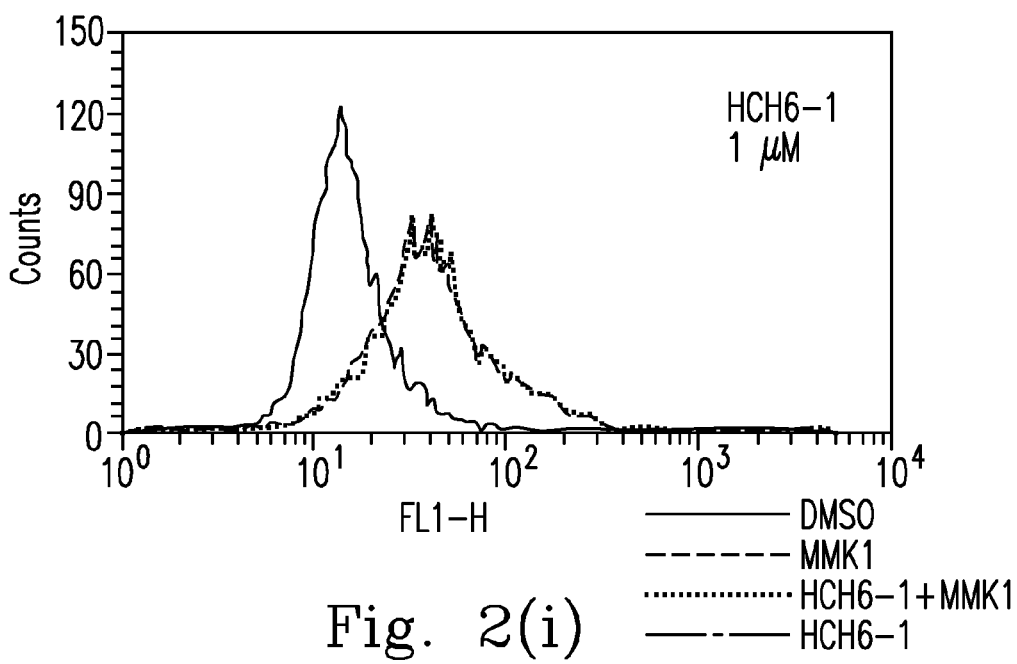
Figure 2J:
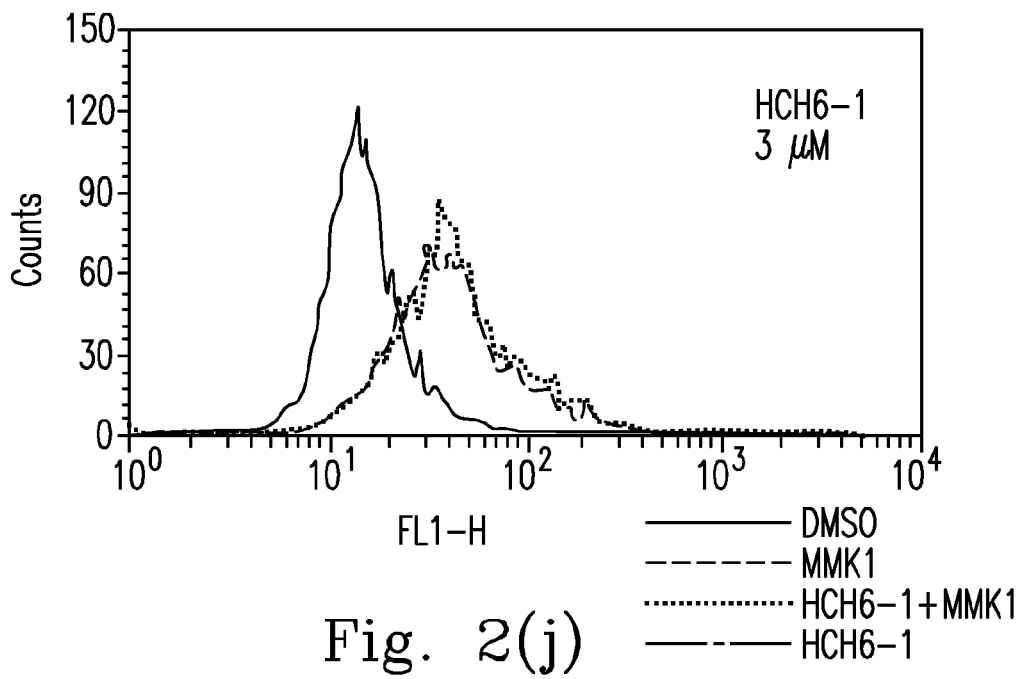
Figure 2K:
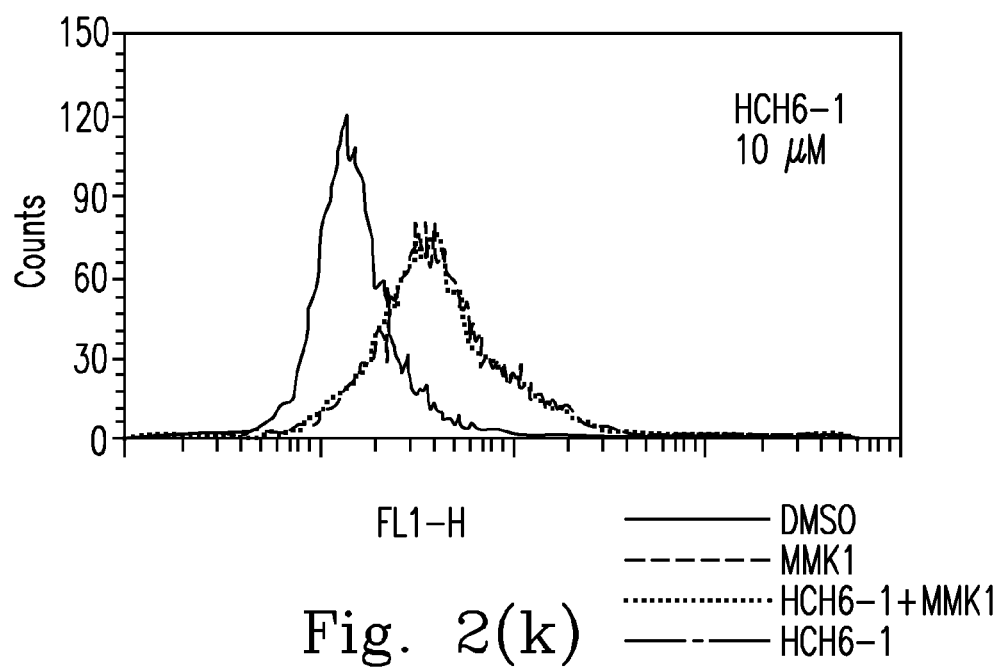
Figure 2L:
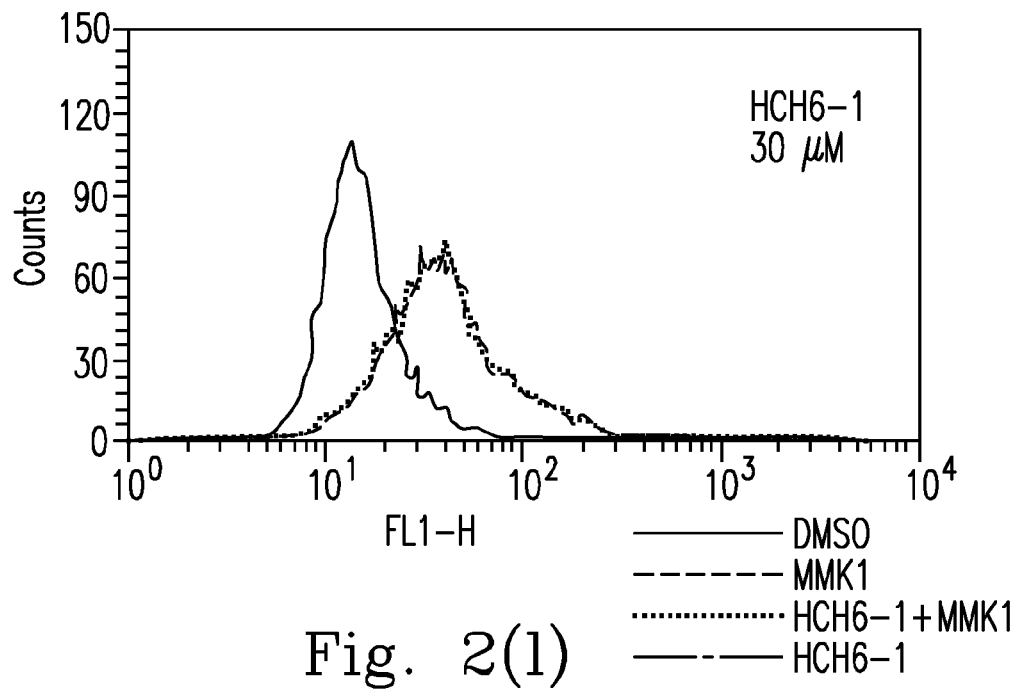
Figure 2M:
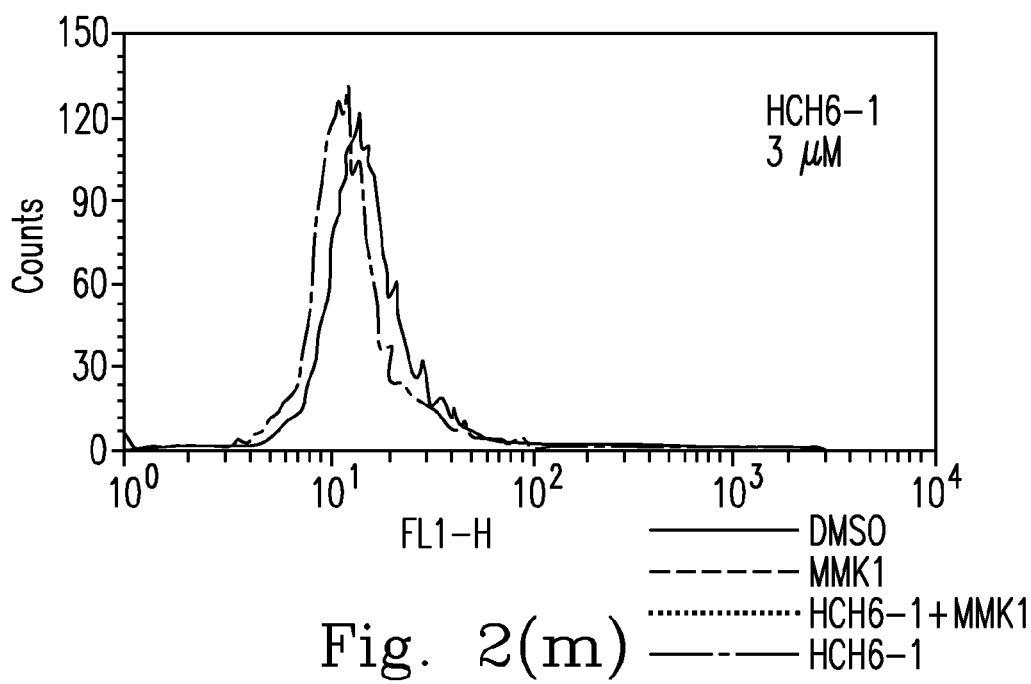
Figure 2N:
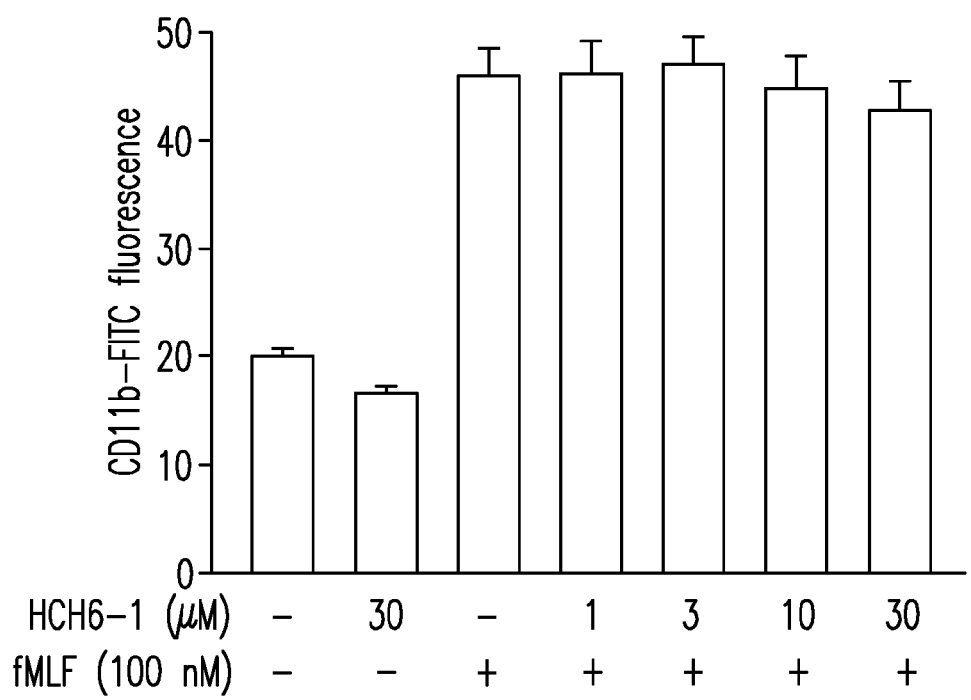
Figure 2O:
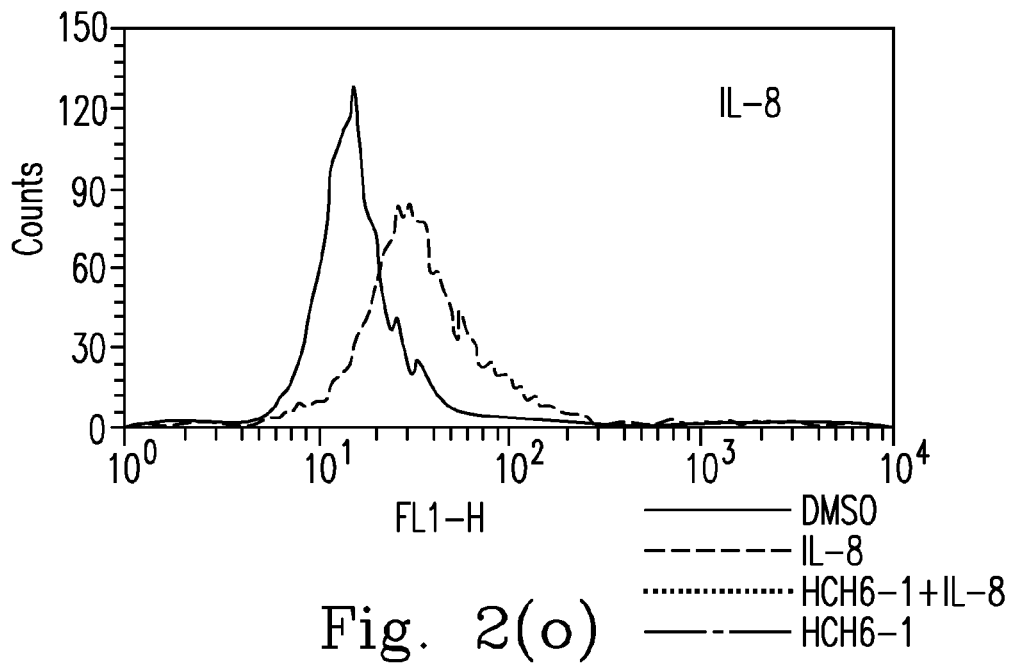
Figure 2P:
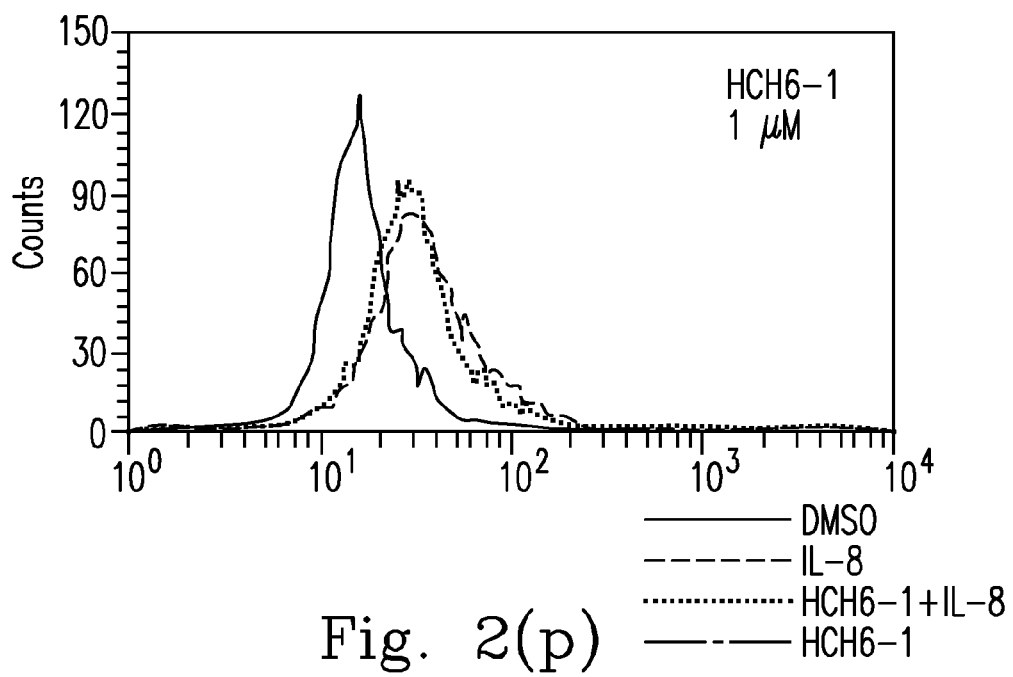
Figure 2Q:
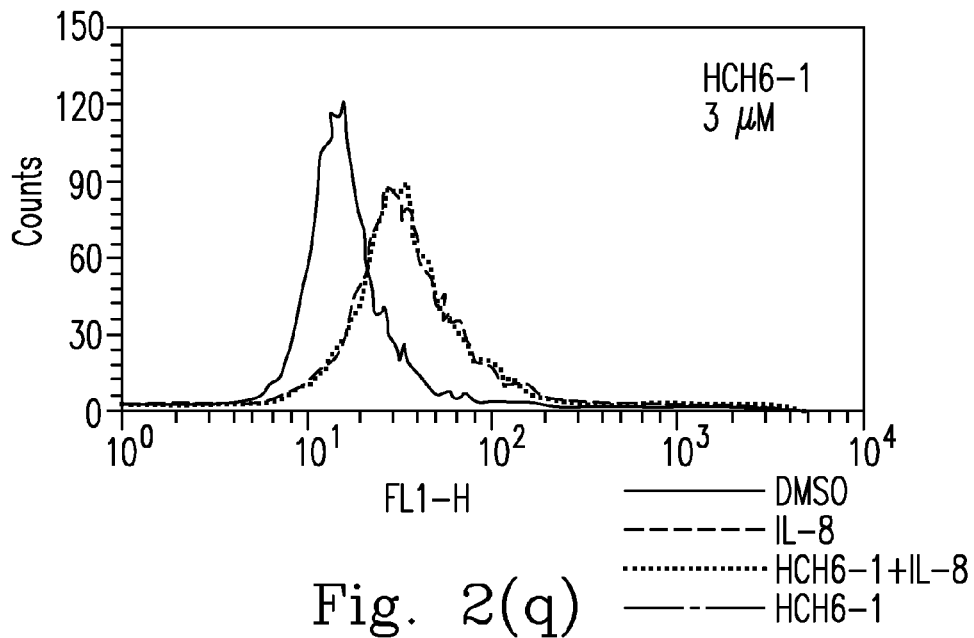
Figure 2R:
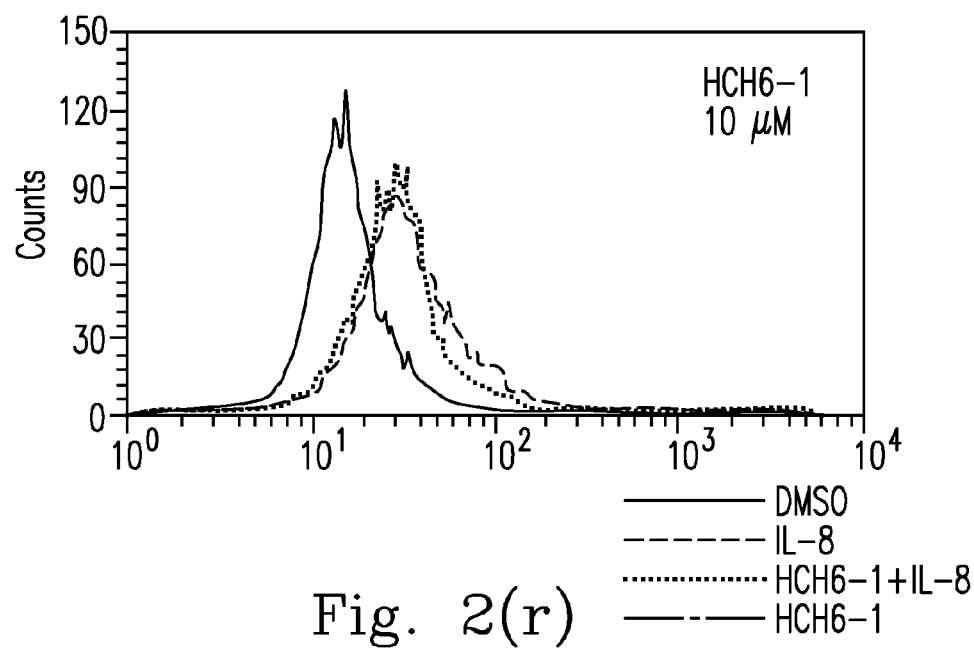
Figure 2S:
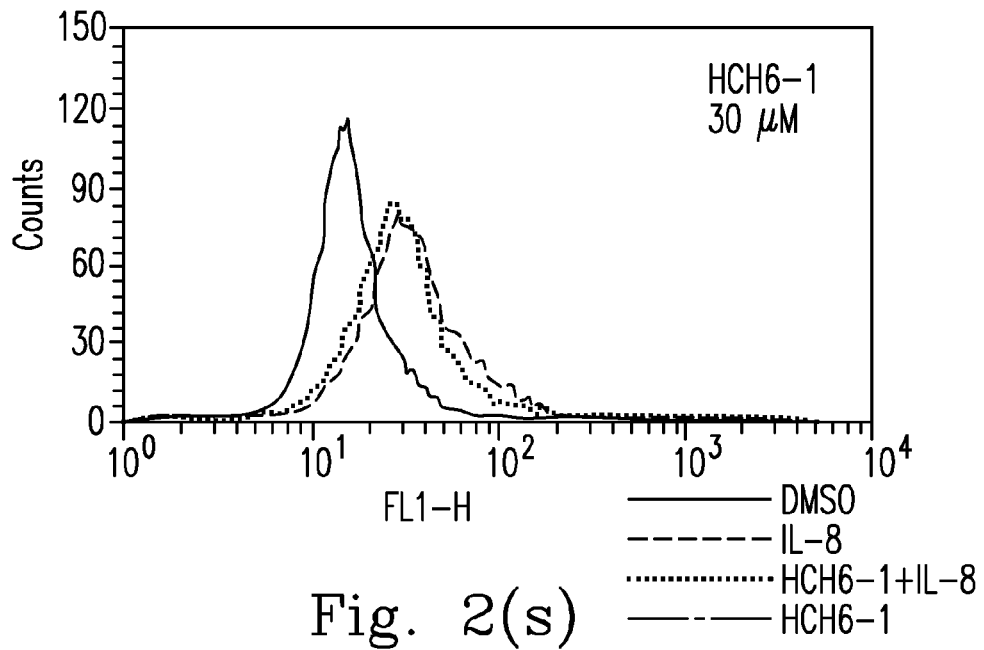
Figure 2T:
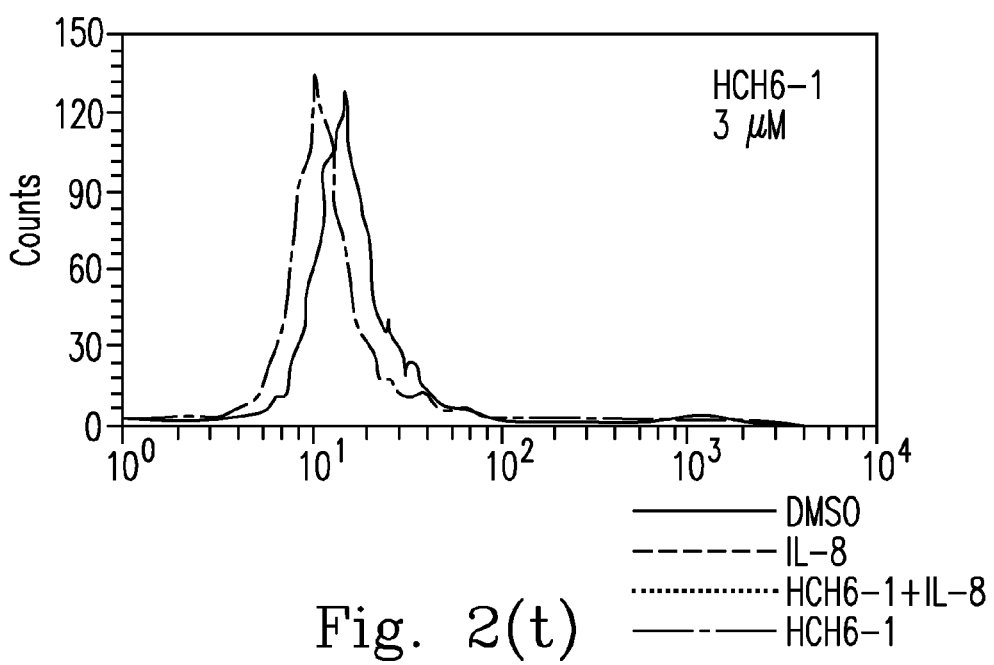
Figure 2U:
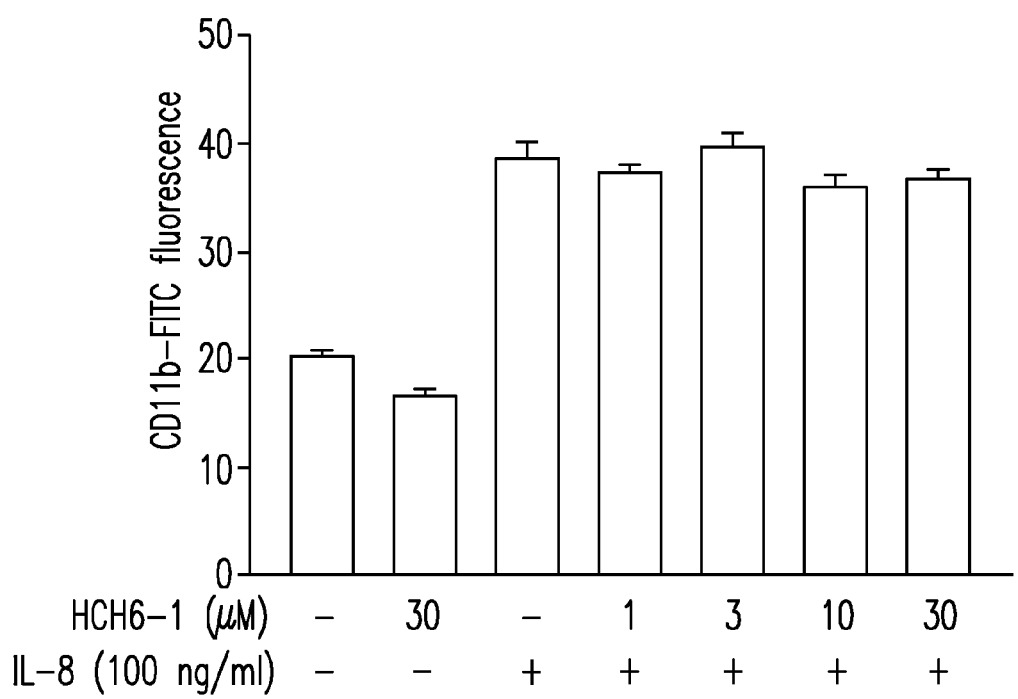
Figure 3A:
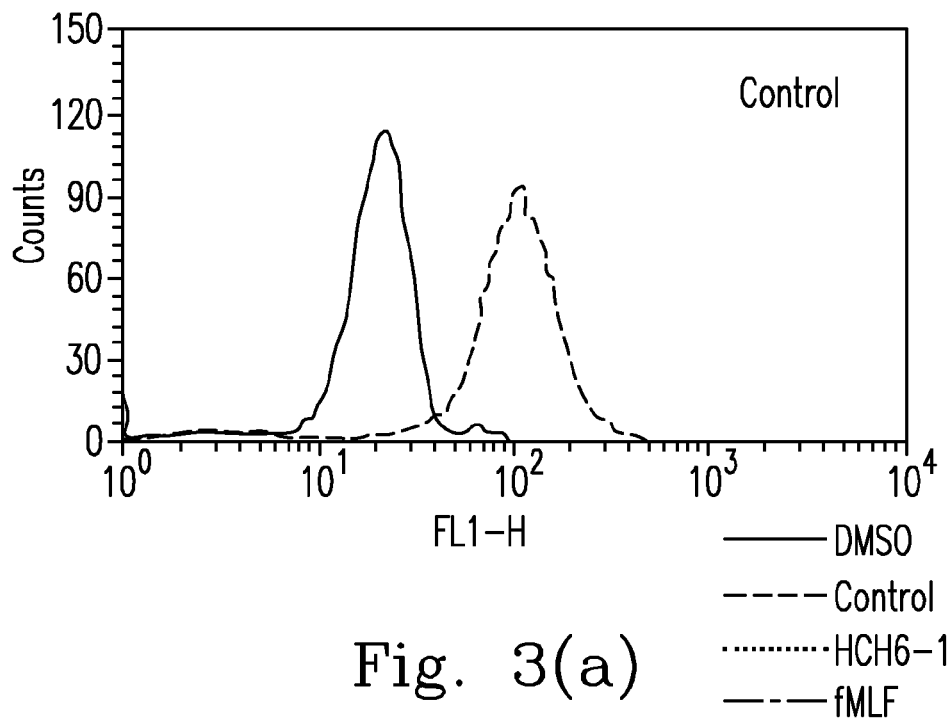
FIGS. 3(a)-3(h) show inhibition of HCH6-1 for the effect on FNLFNYK combined with FPR1 on the membranes of human neutrophils.
Figure 3B:
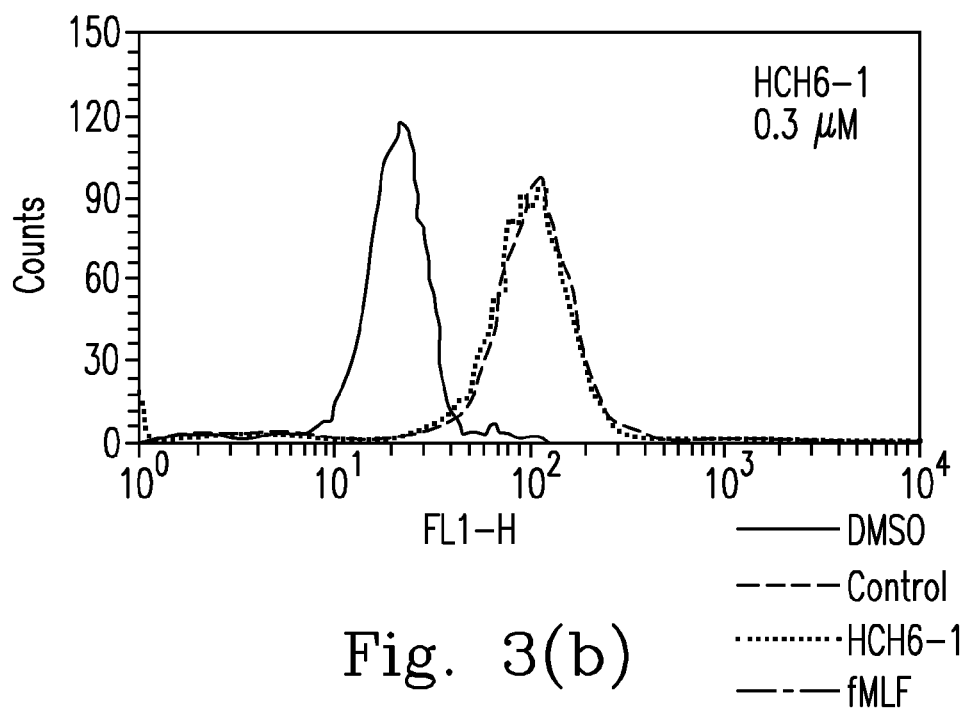
Figure 3C:
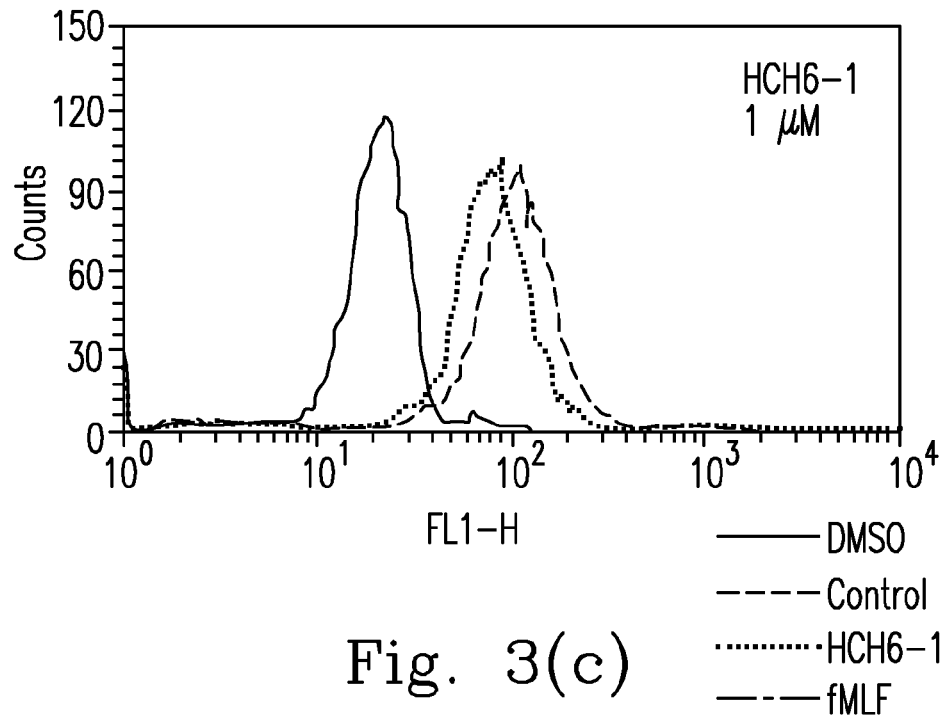
Figure 3D:
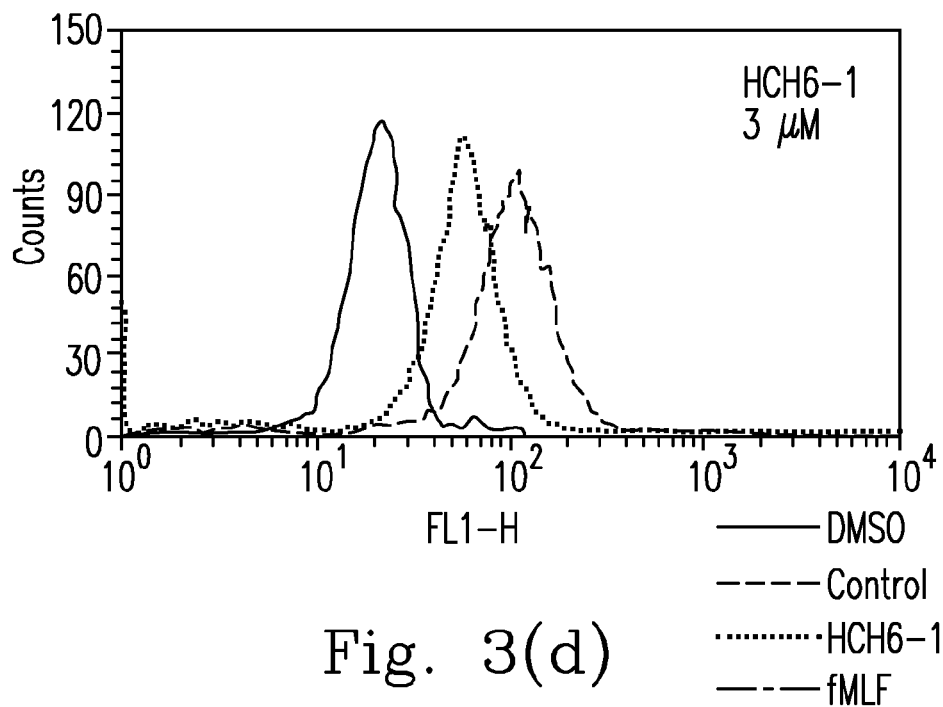
Figure 3E:
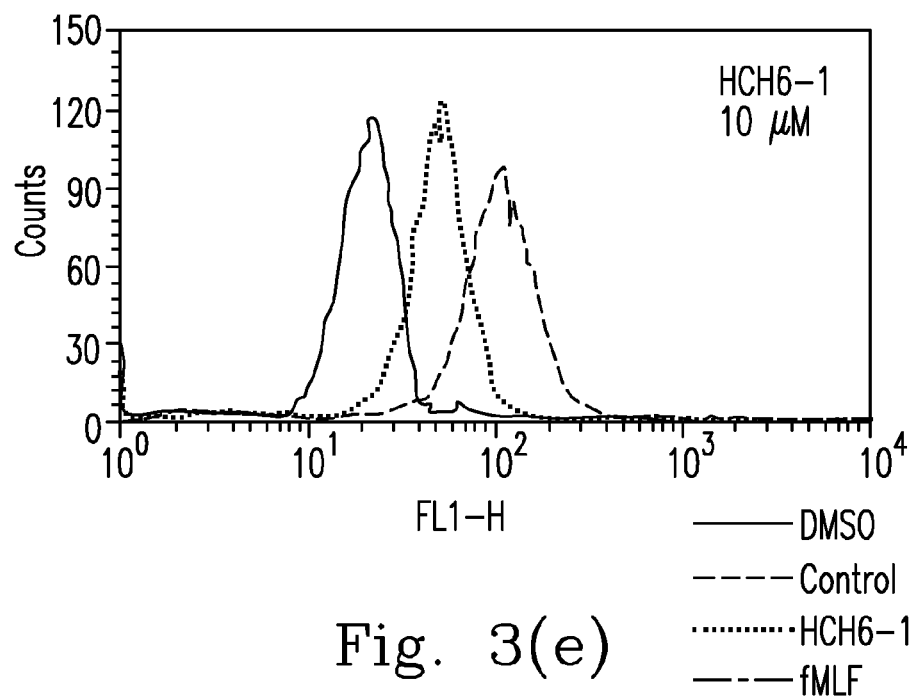
Figure 3F:
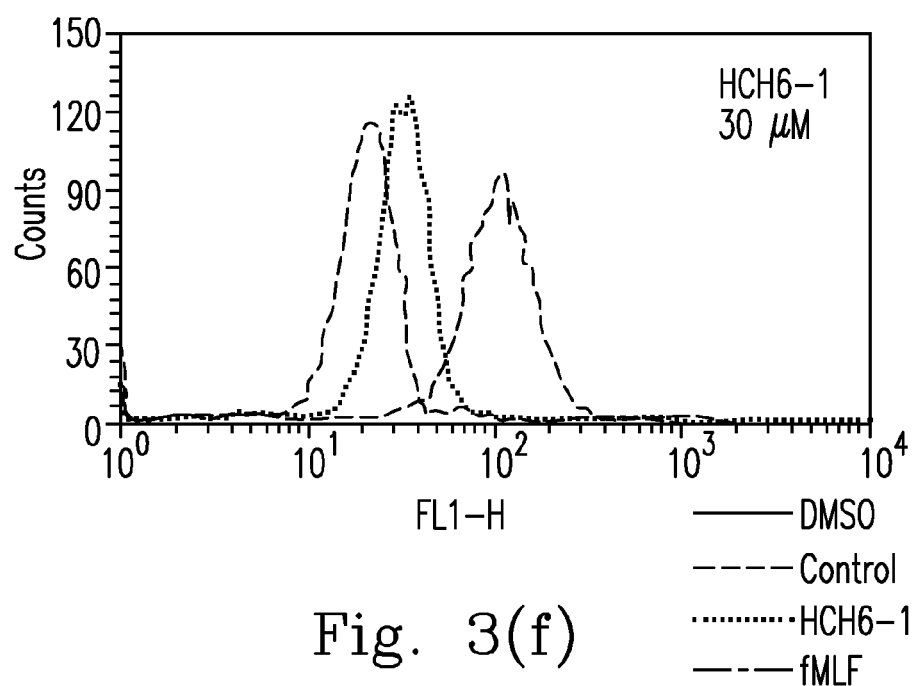
Figure 3G:
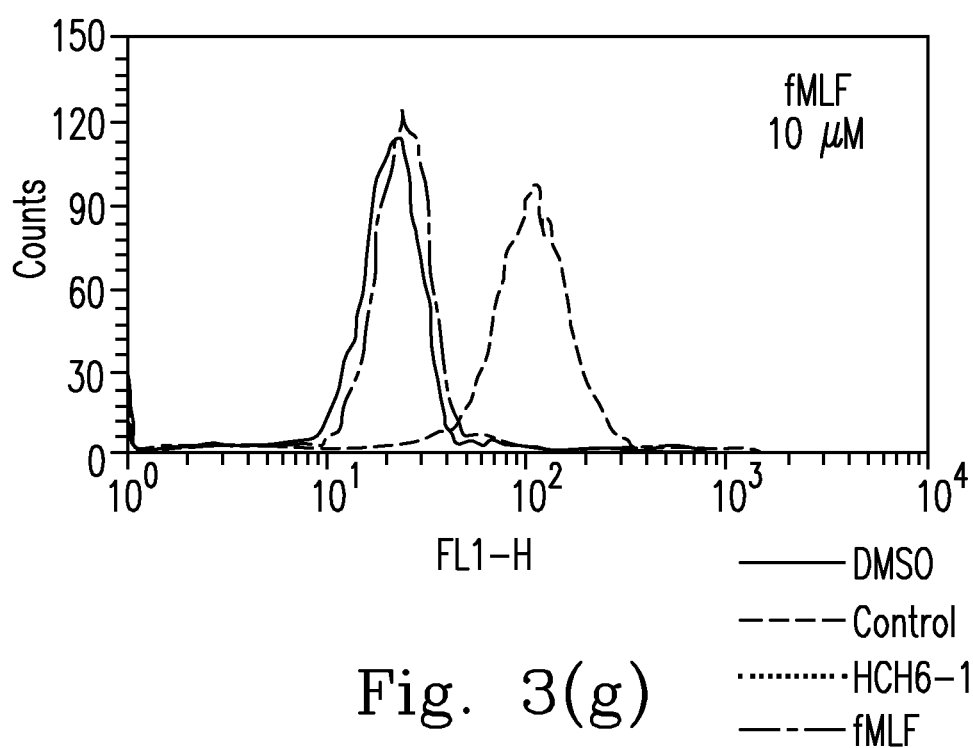
Figure 3H:
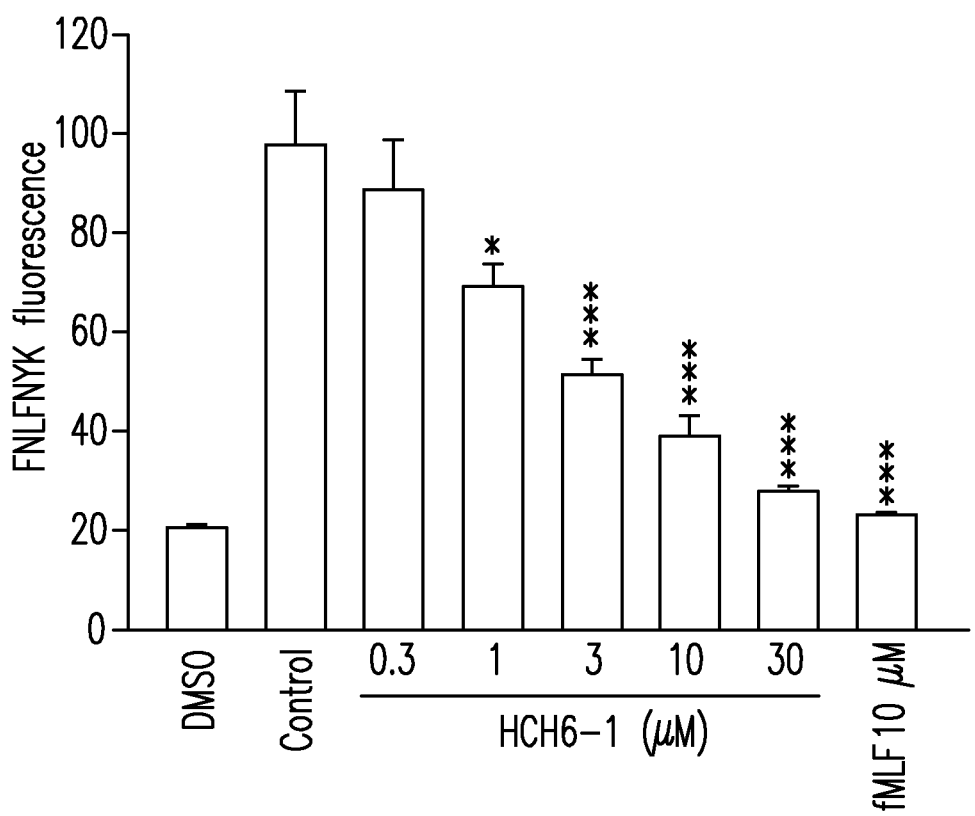
Figure 4A:
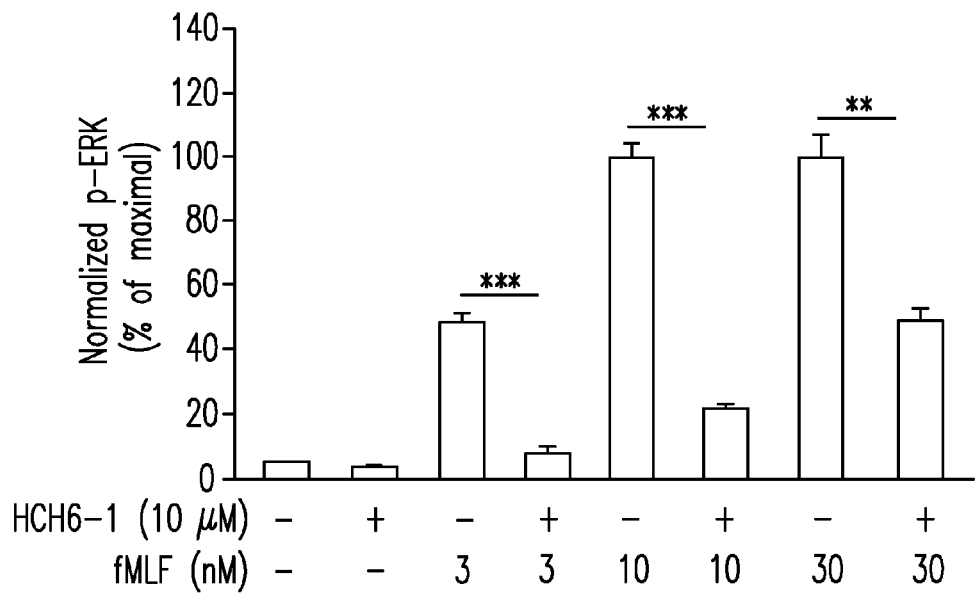
FIGS. 4(a)-4(d) show the significant capability of HCH6-1 to suppress phosphorylation for MAPKs (ERK, p38 and JNK), as well as Akt.
Figure 4B:
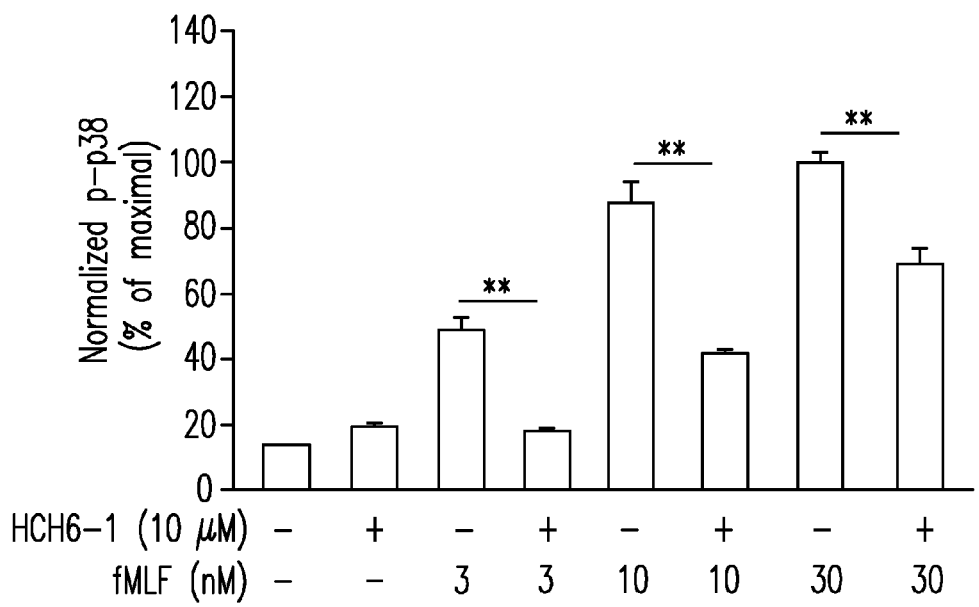
Figure 4C:
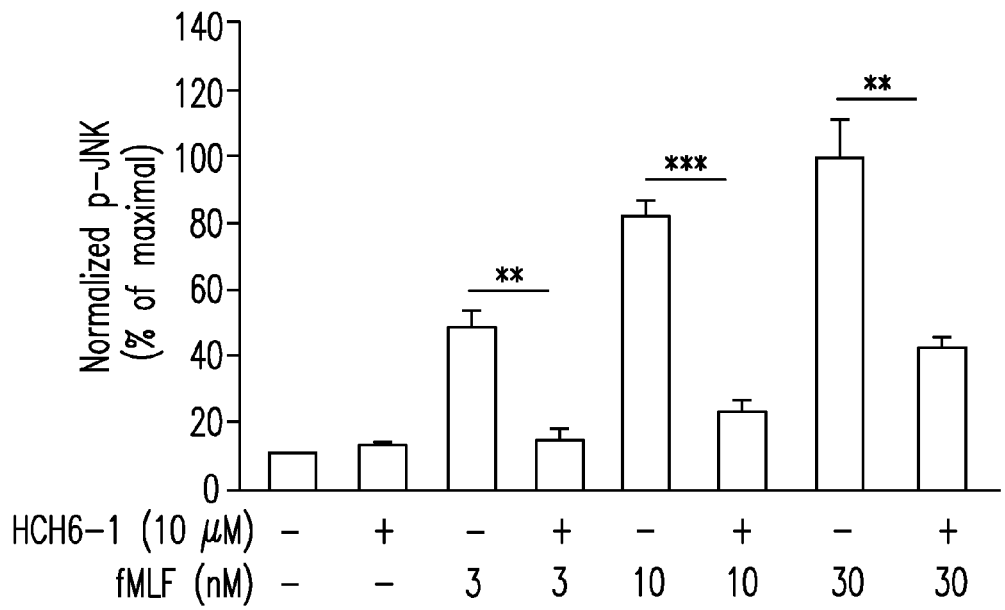
Figure 4D:
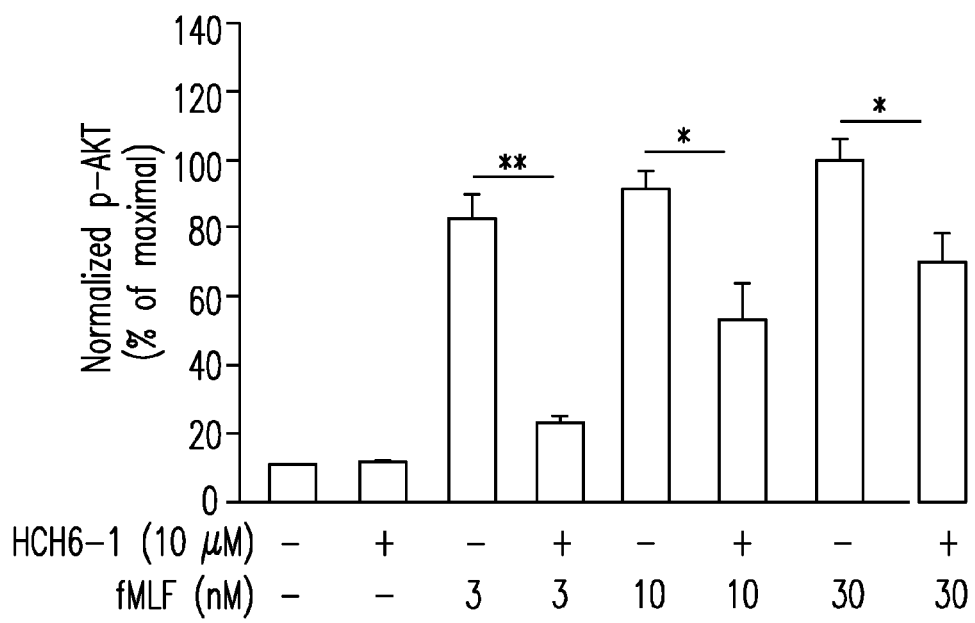

The suspension of neutrophils was mixed at 37° C. and pre-heated for 5 min, and then compounds with different concentrations for measurements were added. After that, CB with 1 μg ml$^{-1}$ was added to react for 3 min, and subsequently fMLF with 30 nM is added to react for 10 min. And the reaction termination is done by on-ice setting. The supernatant was removed after centrifugation, and make the cells suspension again in the balanced salt solution containing bovine serum albumin (BSA). Anti-CD11b with fluorescein isothiocyanate (FITC) labeling was added, and kept on ice and in the dark. Finally, a balanced salt solution was added to terminate the reaction. By means of the flow cytometer for detecting the anti-CD11b with fluorescein isothiocyanate (FITC) labeling, it is possible to further evaluate whether the candidate compounds had influence on CD11b expression on the cell membranes of activated neutrophils according to changes in fluorescence. The experimental results showed that the HCH6-1 concentration is correlated to the inhibition of CD11b expression on cell membranes under the stimulus of fMLF, while IC$_{50}$ was 0.26±0.05 μM, as shown in FIGS. 2(a) and 2(b). However, there was no inhibitory effects for HCH6-1 under the stimuli of Leu-Glu-Ser-Ile-Phe-Arg-Ser-Leu-Leu-Phe-Arg-Val-Met (MMK1) and IL-8 (100 nM), as shown in FIGS. 2(h) and 2(n).

[Embodiment 10] Receptor Test

Membranes of human neutrophils contain fMLF receptor, formyl peptide receptor 1 (FPR1), with which formyl-Nle-Leu-Phe-Nle-Tyr-Lys (FNLFNYK) carrying the fluorescence property was combined with FPR1 and competed with the candidate compound for receptor binding. Therefore, by binding with the receptor, it was possible to further clarify whether the compound interacts with the receptor. FIGS. 3(a)-3(h) showed the inhibition of HCH6-1 regarding the effect of FNLFNYK combined with FPR1 on the membranes of human neutrophils. The experimental results showed that the HCH6-1 concentration was correlated to the inhibition of FNLFNYK bound to FPR1, while IC$_{50}$ was 2.02±0.34 μM.

[Embodiment 11] Western Blot

Mitogen-activated protein kinases (MAPKs) and the expression of Akt phosphorylation are closely related to the regulation of cell inflammatory response. By specific binding of antibodies, each compound's influence on protein expression activated by different signals was observed. As to neutrophils, MAPKs (ERIK, p38, and JNK) and Akt signal transduction pathways are involved in the regulation of superoxide anion generation and elastase release. It is can be seen from the above-mentioned experiments that HCH6-1 is capable of competitively inhibiting superoxide anion generation and elastase release. Whether downstream MAPKs and Akt signal transduction pathways of FPR1 were involved in the regulation of superoxide anion generation and elastase release is explored below.

FIGS. 4(a)-4(d) showed the capability of HCH6-1 to significantly inhibit phosphorylation for MAPKs (ERK, p38 and JNK) and Akt. The experimental conditions were as follows. HCH6-1 (10 μM) was pre-processed for 5 min, followed by stimulus of fMLF (3-30 nM) for 30 sec. The experimental results showed that HCH6-1 inhibited signal transduction of MAPKs and Akt in cells. With a low concentration stimulus of fMLF (3 nM), HCH6-1 significantly suppressed phosphorylation for MAPKs and Akt, and thus an indirect proof for the competitive capability is provided, as shown in FIGS. 4(a)-4(d).

[Embodiment 12] Statistical Analysis

Results are expressed as the mean±SEM. Data were analyzed using GraphPad Prism software (GraphPad Software, San Diego, Calif.). Statistical analysis was performed using a Student's t-test or one-way analysis of variance (ANOVA), followed by a Tukey range test. A value of p<0.05 was considered statistically significant.

In conclusion, the present invention utilizes simple synthesizing methods to genrate a series of dipeptide derivatives, in which two amino acids need to be L (S) and D (R) configurations respectively, and the N-terminal and C-terminal are substituted. It was found that this series of compounds excellently suppresses superoxide anion generation and elastase release of human neutrophils in the experimental mode which were induced by specific activators of FPR1, fMLF. Although superoxide anion generation and elastase release of human neutrophils induced by specific activators of FPR2, WKYMVm were also suppressed, there was a significant decrement by 3-20 fold compared to the inhibition induced by specific activators of FPR1. It is shown that this novel series of peptide derivatives selectively antagonizes against FPR1.

More specifically, compound 3 (HCH6-1) has only slight influence whenever it is triggered by non-FPR1 activation. Interestingly, compound 3 (HCH6-1) competitively inhibited the downstream signal transduction pathways of FPR1, including calcium, MAPKs and Akt. By integrating the experimental results, it can be deduced that compound 3 (HCH6-1) selectively and competitively inhibits FPR1 to activate human neutrophils. Under this hypothesis, HCH6-1 is capable of inhibiting the combination of N-formyl-Nle-Leu-Phe-Nle-Tyr-Lys-fluorescein, one kind of FPR-like fluorescein derivative, with FPR1. In Human neutrophils, compound 3 (HCH6-1) is capable of competitively inhibiting FPR1.

In addition, during the synthesizing process of dipeptide derivatives, two isomers containing (E)-N-benzoyl or (Z)—N-benzoyl substitutes in N-terminals can be obtained. Analytical results of the Circular Dichroism Spectrum regarding the compounds shows that the value of Cotton Effect at wavelength 220 nm is negative for dipeptide derivatives containing (E)-N-benzoyl, while the corresponding value at wavelength 220 nm is positive for dipeptide derivatives containing (Z)—N-benzoyl. In activity evaluation, dipeptide derivatives containing the (Z)—N-benzoyl group are superior to those containing the (E)-N-benzoyl group.

The results show that compounds 1 and 24a selectively and competitively inhibits the FPR1-induced human neutrophil activation. Consistent with the hypothesis, compound 1 inhibited the binding of N-formyl-Nle-Leu-Phe-Nle-Tyr-Lys-fluorescein, a fluorescent analogue of fMLP, to FPR. Considering the importance of N-formyl peptides in flammatory processes, our data indicate that these dipeptides may have therapeutic potential to attenuate neutrophil-mediated inflammatory diseases by blocking FPR1.

EMBODIMENTS

1. A method for treating a neutrophil inflammatory disorder with an antagonist of formyl peptide receptor 1 (FPR1), comprising:

providing a derivative of N—(N-aroyl-L-t tophanyl)-D-phenylalanine represented by formula (I), wherein:

the chiral centers in formula (I) are S and R configurations respectively; each of RK and RT is selected from a group consisting of a hydrogen, a hydroxyl group, a $C_1$-$C_4$ alkyl-hydroxyl substituted ($C_1$-$C_4$ alkyl-OH) group, a $C_1$-$C_4$ alkoxyl group, a carboxylic acid group, a $C_1$-$C_4$ alkyl nitrile-substituted (CONH$C_1$-$C_4$alkyl-CN) group, or $C_1$-$C_4$ alkyl-substituted (CONH$C_1$-$C_4$ alkyl) or $C_1$-$C_4$ alkoxyl-substituted (CONH$C_1$-$C_4$ alkoxyl) amido group, a $C_1$-$C_4$ alkyl-substituted ester (COO$C_1$-$C_4$ alkyl) group and a benzoyl group having a $C_1$-$C_4$ alkyl-substituted benzene ring; and each of RM and RS is selected from a group consisting of a hydrogen, a hydroxyl group, a phenyl group, a pyridinyl group, a carboxylic acid group, a $C_1$-$C_4$ alkoxyl substituted ester group, and a benzoyl group having a hydroxyl-substituted, a halogen-substituted, a $C_1$-$C_4$ alkoxyl-substituted or a $C_1$-$C_4$ alkyl-substituted benzene ring.

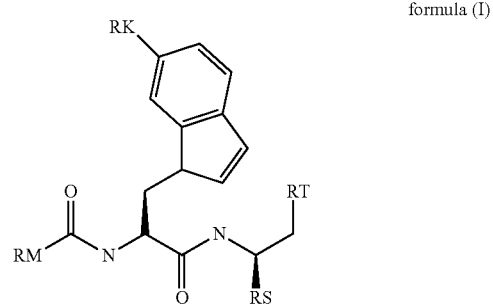

formula (I)

2. The method of Embodiment 1, further comprising providing one selected from a group consisting of a pharmaceutically acceptable salt, solvate and combination thereof for formula (I).

3. The method of any one of Embodiments 1-2, wherein the neutrophil inflammatory disorder is selected from a group consisting of lung injury, chronic obstructive pulmonary disease, acute respiratory distress syndrome, asthma, ischemic reperfusing injury, arthritis and septicemia.

4. A dipeptide derivative represented by formula (I),

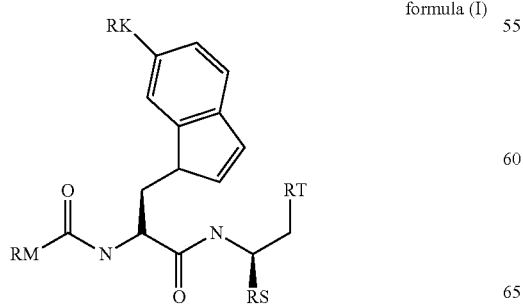

formula (I)

wherein:

the chiral centers in formula (I) are S and R configurations respectively; each of RK and RT is selected from a group consisting of a hydrogen, a hydroxyl group, a $C_1$-$C_4$ alkyl-substituted hydroxyl group, a $C_1$-$C_4$ alkoxyl group, a carboxylic acid group, a $C_1$-$C_4$ alkyl nitrile-substituted, $C_1$-$C_4$ alkyl-substituted or $C_1$-$C_4$ alkoxyl-substituted amido group, a $C_1$-$C_4$ alkyl-substituted ester group and a benzoyl group having a $C_1$-$C_4$ alkyl-substituted benzene ring; and each of RM and RS is selected from a group consisting of a hydrogen, a hydroxyl group, a phenyl group, a pyridinyl group, a carboxylic acid group, a $C_1$-$C_4$ alkoxyl substituted ester group, and a benzoyl group having a hydroxyl-substituted, a halogen-substituted, a $C_1$-$C_4$ alkoxyl-substituted or a $C_1$-$C_4$ alkyl-substituted benzene ring.

5. The dipeptide derivative of Embodiment 4, wherein the halogen is one selected from a group consisting of fluorine (F), chlorine (CO, bromine (Br) and iodine (I).

6. The dipeptide derivative of any one of Embodiments 4-5 inhibits and antagonizes a formyl peptide receptor 1.

7. A dipeptide derivative represented by formula (I),

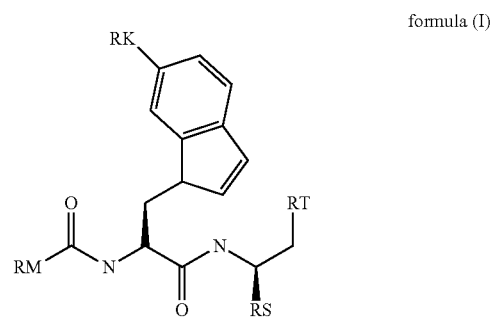

formula (I)

wherein:

the chiral centers in formula (I) are S and R configurations respectively;

RK is selected from a hydrogen; RS is selected from a methylphenyl group;

RM is selected from a phenyl group; and

RT is selected from $C_1$-$C_4$ alkoxyl-substituted ester group.

8. The dipeptide derivative of Embodiment 7 inhibits and antagonizes a formyl peptide receptor 1.

9. A dipeptide derivative represented by formula (I),

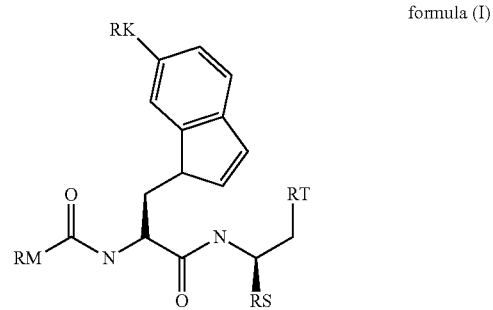

formula (I)

wherein:
the chiral centers in formula (I) are S and R configurations respectively;
RK is selected from a hydrogen;
RS is selected from a methyl-$C_6$-cycloalkyl group;
RM is selected from a phenyl group; and
RT is selected from $C_1$-$C_4$ alkyl-substituted ester group.

10. The dipeptide derivative of Embodiment 9, further comprising a pharmaceutically acceptable salt, solvate or combination thereof.

11. A method for treating a neutrophil inflammatory disorder with an antagonist of formyl peptide receptor 1 (FPR1), comprising:
providing a derivative of N—(N-aroyl-L-t tophanyl)-D-phenylalanine methyl esters represented by formula (II), wherein:

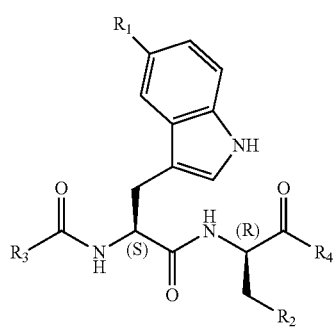

formula (II)

the chiral centers in formula (II) are S and R configurations respectively;
$R_1$ is one selected from a group consisting of a hydrogen, a hydroxyl group and a methoxy group;
$R_2$ is one selected from a group consisting of a non-substituted phenyl group, a mono-substituted phenyl group, a di-substituted phenyl group, or a tri-substituted phenyl group, a pyridinyl group and a $C_4$-$C_6$ cycloalkyl group;
$R_3$ is one selected from a group consisting of a non-substituted benzoyl group, a mono-substituted benzoyl group, a di-substituted benzoyl group and a tri-substituted benzoyl group; and
$R_4$ is one selected from a group consisting of a hydroxyl, a C1-C4 alkoxyl and a glycin-nitrile groups.

12. A method for treating a neutrophil inflammatory disorder with an antagonist of FPR1, comprising:
provide a derivative of N—(N-aroyl-L-tryptophanyl)-D-phenylalanine methyl esters represented by formula (II), wherein:

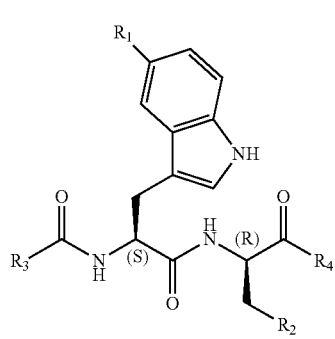

formula (II)

wherein the chiral centers in formula (II) are S and R configurations respectively;
$R_1$ is one selected from a group consisting of a hydrogen, a hydroxyl group and a methoxy group;
$R_2$ is one selected from a group consisting of a non-substituted phenyl group, a mono-substituted phenyl group, a di-substituted phenyl group, or a tri-substituted phenyl, a pyridinyl and a $C_4$-$C_6$ cycloalkyl groups;
$R_3$ is one selected from a group consisting of a non-substituted benzoyl group, a mono-substituted benzoyl group, a di-substituted benzoyl group and a tri-substituted benzoyl group; and
$R_4$ is one selected from a group consisting of a hydroxyl group, a C1-C4 alkoxyl group and a glycin-nitrile group.

13. The method of Embodiment 12, further comprising providing one selected from a group consisting of a pharmaceutically acceptable salt, solvate and combination thereof for formula (II).

14. The method of any one of Embodiments 12-13, wherein the neutrophil inflammatory disorder is selected from a group consisting of lung injury, chronic obstructive pulmonary disease, acute respiratory distress syndrome, asthma, ischemic reperfusing injury, arthritis and septicemia.

15. A dipeptide derivative represented by formula (II),

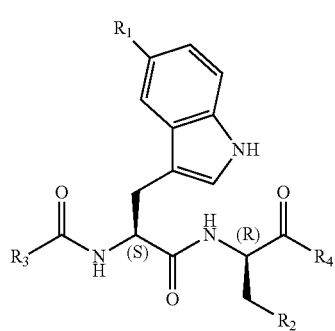

formula (II)

wherein:
the chiral centers in formula (II) are S and R configurations respectively;

$R_1$ is selected from one of a hydrogen and a hydroxyl group;

$R_2$ is one selected from a group consisting of non-substituted phenyl group, mono-substituted phenyl group, di-substituted phenyl group, or tri-substituted phenyl group and pyridinyl group;

$R_3$ is one selected from a group consisting of a non-substituted benzoyl group, a mono-substituted benzoyl group, a di-substituted benzoyl group and a tri-substituted benzoyl group; and $R_4$ is selected from one of C1-C4 alkoxyl group and a glycin-nitrile group.

16. The dipeptide derivative of Embodiment 15 inhibits and antagonizes a FPR1.

17. The dipeptide derivative of any one of Embodiments 15-16 inhibits a fMLP's derivative N-Formyl-Nle-Leu-Phe-Nle-Tyr-Lys-fluorescein FNLFNYK binding to the FPR1.

18. The dipeptide derivative of any one of Embodiments 15-17 inhibits at least one selected from a group consisting of FPR1 downstream, calcium, MAPKs and Akt.

19. The dipeptide derivative of any one of Embodiments 15-18, wherein the dipeptide derivative competitively inhibits superoxide anion generation and neutrophil elastase release induced by a FPR1 activator.

20. The dipeptide derivative of any one of Embodiments 15-19, wherein the FPR1 activator is derived from a neutrophil inflammatory disorder and the neutrophil inflammatory disorder is selected from a group consisting of following diseases or symptoms: lung injury, chronic obstructive pulmonary disease, acute respiratory distress syndrome, asthma, ischemic reperfusing injury, arthritis and septicemia.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A dipeptide derivative represented by formula (II),

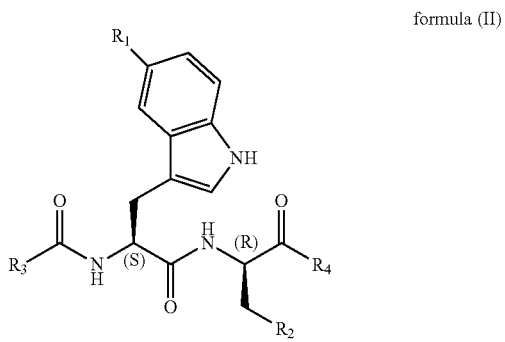

formula (II)

wherein:
the chiral centers in formula (II) are S and R configurations respectively;

$R_1$ is a hydrogen or a hydroxyl group;

$R_2$ is selected from the group consisting of, a non-substituted phenyl group, a mono-substituted phenyl group, a di-substituted phenyl group, a tri-substituted phenyl group and a pyridinyl group;

$R_3$ is selected from the group consisting of, a non-substituted benzyl group, a mono-substituted benzyl group, a di-substituted benzyl group, and a tri-substituted benzyl group; and $R_4$ is a C1-C4 alkoxyl group or a glycin-nitrile group.

2. The dipeptide derivative of claim 1, wherein the dipeptide derivative inhibits and antagonizes a formyl peptide receptor 1.

3. The dipeptide derivative of claim 2, wherein the dipeptide derivative inhibits at least one FPR1 downstream signal that is selected from the group consisting of calcium, mitogen-activated protein kinases and protein kinase B.

4. The dipeptide derivative as claimed in claim 2, wherein the dipeptide derivative competitively inhibits superoxide anion generation and neutrophil elastase release induced by a FPR1 activator.

5. The dipeptide derivative of claim 4, wherein the FPR1 activator is derived from a neutrophil inflammatory disorder, which is selected from the group consisting of lung injury, chronic obstructive pulmonary disease, acute respiratory distress syndrome, asthma, ischemic reperfusing injury, arthritis and septicemia.

6. The dipeptide derivative of claim 1, wherein $R_1$ is hydrogen; $R_2$ is a non-substituted phenyl group; $R_3$ is a non-substituted benzyl group; and $R_4$ is a methoxy group.

* * * * *